United States Patent [19]
Baker et al.

[11] Patent Number: 5,571,706
[45] Date of Patent: Nov. 5, 1996

[54] PLANT VIRUS RESISTANCE GENE AND METHODS

[75] Inventors: Barbara J. Baker, Richmond; Steven A. Whitham, Albany, both of Calif.

[73] Assignees: The United States of America as represented by the Secretary of Agriculture, Washington, D.C.; The Regents of the University of California, Oakland, Calif.

[21] Appl. No.: 261,663

[22] Filed: Jun. 17, 1994

[51] Int. Cl.$^6$ ............................. C12N 15/00; C12N 5/14; A01H 1/04; C07H 17/00
[52] U.S. Cl. .................. 435/172.3; 435/69.1; 435/240.4; 800/205; 800/DIG. 40; 800/DIG. 43; 800/DIG. 44; 536/23.6
[58] Field of Search ........................... 800/205, DIG. 40, 800/DIG. 43, DIG. 44; 536/23.6; 435/69.1, 172.3, 240.4, 320.1

[56] References Cited

U.S. PATENT DOCUMENTS 4,732,856  3/1988  Federoff ............................... 435/172.3

OTHER PUBLICATIONS

Lewin (1987) Science 237:70.
Nejidat et al (1990) Physiologia Plantarium 80:662–668.
Abel et al (1986) Science 232:738–743.
B. Baker, S. Whitham, D. Choi, R. Hehl, and C. Corr, "Transposon Tagging of the TMV Resistance Gene N Using the Maize Controlling Element," (Abstract), Keystone Symposium on Crop Improvement, Keystone, Colorado, Jan. 10 (1994).
N. T. Keen, A. Bent, and B. Staskawicz, "Plant Disease Resistance Genes: Interactions with Pathogens and Their Improved Utilization to Control Plant Diseases," *Biotechnology in Plant Disease Control*, Wiley–Liss, Inc., pp. 65–88 (1993).
H. H. Flor, "Inheritance of Reaction to Rust in Flax," *Journal of Agricultural Research* 74:241–262 (1947).
N. T. Keen, "Gene–for–Gene Complementarity in Plant Pathogen Interactions," *Annual Review of Genetics* 24:447–463 (1990).
N. T. Keen, "The Molecular Biology of Disease Resistance," *Plant Molecular Biology* 19:109–122 (1992).
G. S. Johal and S. P. Briggs, "Reductase Activity Encoded by the *HM1* Disease Resistance Gene in Maize," *Science* 258:985–987 (1992).
G. B. Martin et al., "Map–Based Cloning of a Protein Kinase Gene Conferring Disease Resistance in Tomato," *Science* 262:1432–1436 (1993).
C. J. Lamb, M. A. Lawton, M. Dron, and R. A. Dixon, "Signals and Transduction Mechanisms for Activation of Plant Defenses against Microbial Attack," *Cell* 56:215–224 (1989).
C. J. Lamb, "Plant Disease Resistance Genes in Signal Perception and Transduction," *Cell* 76:419–422 (1994).
F. O. Holmes, "Inheritance of Resistance to Tobacco–Mosaic Disease in Tobacco," *Phytopathology* 28:553–561 (1938).

B. Baker, J. Schell, H. Lorz, and N. Fedoroff, "Transposition of the Maize Controlling Element 'Activator' in Tobacco," *Proceedings of National Academy of Science, USA* 83:4844–4848 (1986).
H. S. Padgett and R. N. Beachy, "Analysis of a Tobacco Mosaic Virus Strain Capable of Overcoming N Gene–Mediated Resistance," *Plant Cell* 5:577–586 (1993).
N. Suzuki et al., "Leucine–rich Repeats and Carboxyl Terminus Are Required for Interaction of Yeast Adenylate Cyclase with RAS proteins," *Proceedings of the National Academy of Science USA* 87:8711–8715 (1990).
M. Saraste, P. R. Sibbald, and A. Wittinghofer, "The P–loop: a Common Motif in ATP– and GTP–binding Proteins," *Trends in Biochemical Sciences* 15:430–434 (1990).
A. Heguy et al., "Amino Acids Conserved in Interleukin–1 Receptors (IL–1Rs) and the *Drosophila* Toll Protein are Essential for IL–1 Signal Transduction," *Journal of Biological Chemistry* 267:2605–2609 (1992).
F. M. Ausubel et al., Editors, *Current Protocols in Molecular Biology* vol. 1, chapters 1–7, (1989). (Table of Contents enclosed).
R. B. Horsch et al., "A Simple and General Method for Transferring Genes into Plants," *Science* 227:1229–1231 (1985).
R. Hehl and B. Baker, "Induced Transposition of Ds by a Stable Ac in Crosses of Transgenic Tobacco Plants," *Molecular and General Genetics* 217:53–59 (1989).
B. Baker et al., "Phenotypic Assay for Excision of the Maize Controlling Element Ac in Tobacco," *The EMBO Journal* 6:1547–1554 (1987).
R. Hehl and B. Baker, "Properties of the Maize Transposable Element *Activator* in Transgenic Tobacco Plants: A Versatile Inter–Species Genetic Tool," *The Plant Cell* 2:709–721 (1990).
N. V. Federoff, D. B. Furtek, and O. E. Nelson, Jr., "Cloning of the *Bronze* Locus in Maize by a Simple and Generalizable Procedure Using the Transposable Controlling Element *Activator (Ac)*," *Proceedings of the National Academy of Science USA* 81:3825–3829 (1984).
C. Hashimoto K. Hudson, and K. V. Anderson, "The *Toll* gene of Drosophila, Required for Dorsal–ventral Embryonic Polarity, Appears to Encode a Transmembrane Protein," *Cell* 52:269–279 (1988).
T. W. Traut, "The Functions and Consensus Motifs of Nine Types of Peptide Segments that Form Different Types of Nucleotide–Bindg Sites," *European Journal of Biochemistry* 222:9–19 (1994).

*Primary Examiner*—David T. Fox
*Assistant Examiner*—Elizabeth F. McElwain
*Attorney, Agent, or Firm*—M. Howard Silverstein; John D. Fado; Margaret A. Connor

[57] ABSTRACT

Genomic and cDNA sequences encoding plant virus resistance proteins are provided herein. Specifically exemplified are sequences encoding the N protein derived from tobacco mosaic virus resistant *Nicotiana glutinosa*. TMV-sensitive tobacco plants genetically engineered to contain and express an N protein coding sequence from a TMV-resistant line acquire the TMV-resistant phenotype.

32 Claims, 8 Drawing Sheets

Nt1 probe 1 2 3 4 5 6 7 8

—10.2kb—

—7.9kb—

N5 probe

Ac probe

FIG. 3C

PLANT VIRUS RESISTANCE GENE AND METHODS

FIELD OF THE INVENTION

The present invention relates to methods and materials for improved control of plant pathogens. More particularly, the present invention relates to nucleic acid sequences which encode an N gene protein, recombinant polynucleotide molecules containing the sequences, and uses thereof, particularly the use to transform a plant of the family Solanaceae to make it resistant to tobacco mosaic virus.

BACKGROUND OF THE INVENTION

Major losses of crop yields and quality can result from infection of crops by plant disease pathogens including viruses, bacteria, and fungi. The tobacco mosaic virus (TMV) infects plants of commercial importance including tobacco and related plants such as tomato and pepper. While not lethal, TMV affects the growth and productivity of these plants. The virus pathogen spreads throughout the plant in two stages. First, virus infection occurs at the site where the virus is introduced into the cells of the host plant. Second, virus replication occurs wherein the virus multiplies within the cells of the plant.

Plants have numerous mechanisms which provide natural resistance to attack by pathogens. These include preformed structural and chemical barriers and active resistance mechanisms. Plant disease resistance to numerous pathogens is controlled by single complementary genes in the plant and the pathogen. The genes of the plant are termed resistance genes, and those of the pathogen are termed avirulence genes. Plants bearing a resistance gene are effectively protected from disease caused by a pathogen bearing the corresponding avirulence gene.

The dominant N locus of tobacco confers resistance to TMV and mediates a localized hypersensitive response (HR) at the site of viral infection and the induction of the systemic acquired resistance (SAR) response in cells neighboring the infection site and throughout the plant. Tobacco plants heterozygous or homozygous for the N locus are resistant to disease caused by TMV. The HR is a complex, active resistance response that is induced in the plant in response to pathogen attack after preformed resistance mechanisms fail (Keen et al., Biotechnology in Plant Disease Control, Wiley-Liss, Inc., pages 65–88 (1993)). HR is characterized by cell death (necrosis) at the site of pathogen ingress. Although necrosis per se may not be responsible for resistance to an invading pathogen, the concomitant syntheses of antimicrobial compounds, pathogenesis-related proteins that characterize the SAR response, and establishment of structural barriers are thought to play a central role in halting pathogen spread. Plant-pathogen interactions in which the outcome is resistance are termed incompatible, whereas those resulting in disease are compatible.

Studies have been carried out on the mechanisms by which plants carrying disease resistance genes discern the presence of an invading pathogen and invoke the HR and SAR. In many instances, the HR is governed by gene-for-gene interactions between incompatible plant and pathogen combinations. The gene model as proposed by Flor (*Journal of Agricultural Research* 74:241–262 (1947)) predicts that disease resistance and pathogen avirulence (the production of an elicitor) are dominant traits. Therefore, resistance will occur only in cases where the plant possesses the specific resistance gene (R gene) and the pathogen possesses the corresponding avirulence gene (Avr gene). Several Avr genes have been cloned from bacteria, fungi, and viruses [see Gabriel and Rolfe, *Annual Rev. Phytopathology* 28:365–391 (1990) and Keen, *Annual Rev. Genet.* 24:447–463 (1990)], and in some instances the nature of the elicitor molecule has been defined (see Keen, *Plant Molecular Biology* 19:109–122 (1992)). The fungal resistance gene, HM1, of maize (Johal and Briggs, *Science* 258:985–987 (1992)) and a bacterial resistance gene, Pro, of tomato (G. Martin et al., *Science* 262:1432–1436 (1993)) have been reported. No natural plant virus resistance gene has been isolated or cloned heretofore.

The simple genetic relationship between R genes and their corresponding Avr genes has led to speculation on the mode of action of R gene products. One model predicts that R genes lie in signaling pathways capable of recognizing pathogens and initiating subsequent signal transduction cascades leading to resistance (Lamb, *Cell* 76:419–422 (1994)). The second model predicts that R gene products are transmembrane ion channels that mediate cell death independent of other events in the cell. The recent cloning of Pto from tomato, conferring resistance to the bacterial pathogen *Pseudomonas syringae* pathovar tomato (Martin et al., *Science* 262:1432–1436 (1993)) suggests that at least the first model may be operating in plant cells. Sequence analysis of Pto indicates that it encodes a serine/threonine kinase. It is theorized that this serine/threonine kinase interacts directly or indirectly with the elicitor molecule and then phosphorylates a subsequent modulator of the resistance response, thereby initiating a signal transduction cascade.

Similarities have been noted between the hypersensitive resistance reponses of plants and the "innate" immune responses of animals. The unifying theme is the rapid production of reactive oxygen species (ROS), known as the oxidative burst. Examples of ROS are the superoxide anion ($O_2$) and hydrogen peroxide ($H_2O_2$). These molecules may have direct antimicrobial effects and other protective effects such as the crosslinking of structural proteins in the plant cell wall. Importantly, ROS can activate expression of defense-related genes in animals and plants (Schreck and Bauerle, *Trends in Cell Biology* 1:39–42 (1991), Chen et al., *Science* 262:1883–1886 (1993)). In mammals, ROS are strongly implicated as second messengers for cytokines such as tumor necrosis factor (TNF) and Interleukin-1(Il-1) in a pathway where the transcription factor NF-kB regulates the expression of immunoglobulins, interleukins and other proteins. A Drosophila transcription factor (Dif) homologous to NF-kB also activates transcription of antibacterial proteins including cecropins, attacins, defensins, and lysozymes (Levine and Hultmark, *Trends in Genetics* 9:178–183 (1993)). The parallel in plants is the induction of Pathogenesis Related Proteins and synthesis of antimicrobial compounds such as phytoalexins, which can be induced by exogenous application of $H_2O_2$.

An important model system for the study of plant resistance responses has been that of the resistance gene N. The N locus is composed of a single dominant gene which mediates induction of a necrotic-type response and the SAR in response to infection by TMV (Holmes, *Phytopathology* 28:553–561 (1938)). It was originally identified in *Nicotiana glutinosa*, and has been introgressed into *N. tabacum*. The N gene mediates a hypersensitive response that is characterized by the formation of local lesions to which tobacco mosaic virus is localized. This is shown in FIG. 1A. Tobacco cultivars without the N gene allow tobacco mosaic virus to spread systemically and develop "mosaic" symptoms characterized by intermittant areas of light and dark green leaf tissue (FIG. 1B).

Recombinant DNA technology offers potential for obtaining plants transformed with a pathogen resistance gene to impart resistance. This approach has been impeded by lack of cloned natural plant resistance genes and by lack of knowledge of the mechanistic basis of resistance. Until recently, however, cloned resistance genes have been unavailable due to the lack of techniques in plants to isolate genes for which no information regarding the nature of the gene or its product is available. Two techniques have recently been developed for plants and do not depend on knowledge of gene or biochemical knowledge of protein have permitted isolation of genes these techniques are positional cloning and transposon tagging (Baker, Schell, Fedoroff, *Proceedings of National Academy of Science, USA* 83:4844–4848 (1986)).

SUMMARY OF THE INVENTION

The present invention comprises DNA sequences in isolated and purified form which encode an N gene protein, which protein has the function of mediating resistance to TMV in a plant synthesizing N gene protein. Genomic and cDNA sequences encoding a particular N gene protein are specifically exemplified herein. Included within the scope of this invention are DNA sequences encoding an N gene protein of the exemplified amino acid sequence. DNA sequences which hybridize specifically to an N gene coding sequence or its complement under standard conditions and which encode N gene proteins which function to mediate resistance to TMV are also encompassed by the present invention.

A further aspect of the invention is the provision of recombinant nucleic acid molecules containing the sequence encoding an N gene protein. Such molecules include, for example, recombinant vectors, such as cloning, expression or transformation vectors, which contain a DNA sequence encoding an N gene protein.

Another aspect of the invention is the provision of cells which are transformed by the above vectors or DNA sequences.

A particular use of the invention is the provision of plants or plant cells transformed with an N gene coding sequence to provide plants having resistance to TMV.

A further aspect of the invention is the provision of oligonucleotide probes capable of detecting an N gene or functional equivalents thereof in plants of the family Solanaceae and the use of the probes to isolate DNA sequences encoding an N gene or a functional equivalent thereof. The DNA sequences which specifically hybridize to the probes and which encode a functional N gene protein are encompassed by the present invention.

Using the sequence of the N gene facilitates the isolation of homologous genes from related and unrelated hosts to obtain genes which protect host plants against related viral pathogens and unrelated pathogens.

In accordance with this discovery, it is an object of the invention to provide gene constructs comprising a DNA sequence which encodes an N gene protein which has the function of mediating resistance to TMV in a plant synthesizing N gene protein.

It is also an object of the invention to provide transformation vectors comprising the N gene construct, which vectors are effective for stably introducing the N gene construct into a plant.

It is another object of the invention to provide transgenic plants having resistance to TMV, wherein the resistance is a result of expression of the N gene construct.

Other objects and advantages of this invention will become readily apparent from the ensuing description.

BRIEF DESCRIPTION OF THE DRAWINGS

FIG. 1A shows a leaf from a plant bearing a functional N gene. FIG. 1B shows a leaf from a TMV susceptible plant. FIG. 1C shows a leaf from a plant displaying areas of necrosis on a TMV susceptible background (the sectored phenotype). FIG. 1D shows a leaf from TMV susceptible SR1 tobacco transformed with the pTG38 T-DNA construct.

FIG. 2A shows the results of hybridization of the Nt-1 probe to genomic DNA isolated from the Nicotiana species *glutinosa, tomentosiformis,* and *sylvestris,* and tobacco cultivars Samsun NN and SR1. FIG. 2B shows the results of Nt-1 hybridization to genomic DNA backcross progeny segregating the Nt1(G) N-linked RFLP marker. FIG. 2C shows hybridization of a 5' Ac probe to the same DNA shown in FIG. 2B.

FIG. 3A–3C shows restriction enzyme maps of a portion of the wild-type N gene and Ac insertionally mutagenized N gene, show Southern blot hybridization analyses of DNA isolated from parental Nicotiana species and from Ac mutagenized plants, sectored plants and mutants bearing the Ac insertion in the wild-type (WT) N gene, and germinal revertants. FIG. 3B shows hybridization of N gene probe N-5 to selected plant DNA. FIG. 3C shows Ac hybridization to selected plant DNA.

FIG. 4A illustrates the organization of the N gene with respect to relative positions of introns and exons, and FIG. 4B provides restriction maps of three genomic clones each containing the full length N gene. These maps were derived from sequence analysis of the cDNA clones C7, C16, and C18 and the G38 genomic clone and restriction digestion analysis of the three genomic clones. cDNA C7, not illustrated, was identical to C18 except that C7 contains intron II and is thought to be a partially processed message. C18 lacks 753 bp at the 5' end. Taken together, C7 and C18 predict a 3432 base pair open reading frame encoding an 1144 amino acid polypeptide. C16 codes for a 652 amino acid protein due to inclusion of a 70 bp alternative exon that changes the reading frame. All three cDNA clones are identical at their 3' ends, but only C7 and C16 are identical at the 5' terminus. FIG. 4B: genomic clones were digested with Eco RI(E), Bam HI(B), and Xho I(X). X* indicates that this Xho I site was provided by the polylinker of the λ Gem 11 cloning vector.

DETAILED DESCRIPTION OF THE INVENTION

Figure 1A:
FIG. 1A–1D shows phenotypes of tobacco leaves following TMV inoculation.
Figure 1B:
Figure 1C:
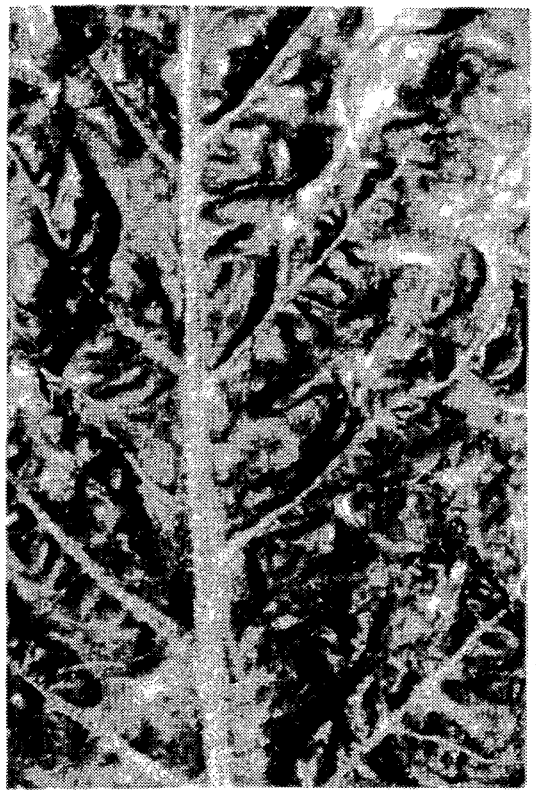
Figure 1D:
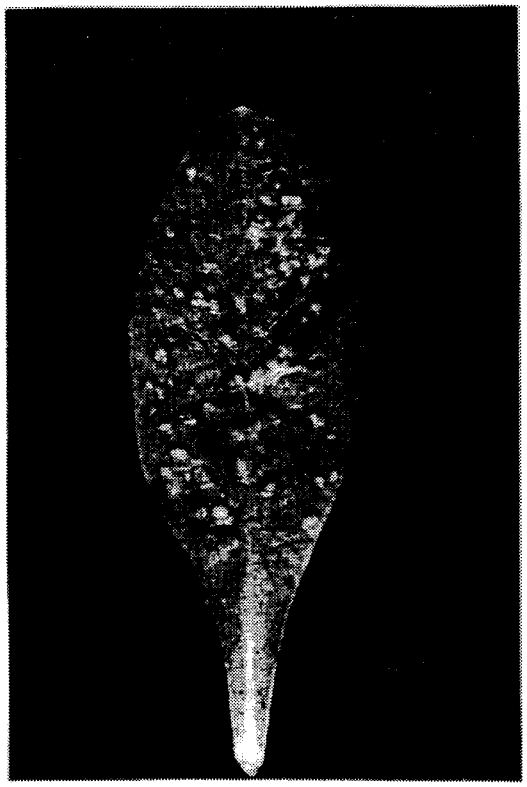

Dominant disease resistance genes in plants are believed to encode proteins that can recognize particular pathogens or races of pathogen and initiate a signal transduction cascade, resulting in expression of disease resistance. TMV enters the cell through mechanical damage to the plant tissue. Upon entering the cell its distribution and localization within the cell are not understood. In N containing tobacco plants, the N protein is presumed to interact directly or indirectly with some component of TMV. This component of TMV has not been well defined yet, but it is believed that the replicase is involved (Padgett and Beachy, *Plant Cell* 5:577–586 (1993)). Upon recognition of TMV, N initiates the resistance response, resulting in the formation of lesions locally and in the induction of systemic acquired resistance distally.

The present disclosure is believed to be the first report of the cloning, sequencing and mediation of transgenic tobacco mosaic virus resistance for the N gene of Nicotiana.

As defined herein, "N gene protein" refers to a protein having the ability to mediate resistance to TMV in a plant synthesizing N gene protein. The N gene includes the genomic sequences which encode an N gene protein and which direct and regulate the transcriptional and translational expression of the N-coding sequences. An exemplified N gene product has a predicted molecular weight of about 131 kDa and a predicted amino acid sequence as given in SEQ ID NO:4 and Table 7A. The exemplified genomic DNA sequence which encompasses the coding sequence for this N gene product is provided in SEQ ID NO: 1. A full length cDNA sequence (from clone C18) and a truncated cDNA sequence (from clone C16) are given in SEQ ID NO:3 and in SEQ ID NO:5, respectively.

The degeneracy of the genetic code is well known to the art; therefore, synonymous coding sequences with one or more codon substitutions can be readily determined by one of ordinary skill in the art. Synonymous coding sequences vary from the exemplified coding sequences but encode proteins of the same amino acid sequences as those specifically provided herein.

Specific embodiments of nucleotide sequences which encode N gene protein which has the function of mediating resistance to TMV are given in SEQ ID NOS:1, 3, and 5.

A cDNA sequence containing the full-length N gene is presented in SEQ ID NO:3. The cDNA sequence is 3760 bp in length. The resulting open reading frame (coding portion), initiating at base 60 and terminating at base 3494 encodes a protein 1144 amino acids in length. The encoded protein is described in Table 7A and in Example 5.

A cDNA sequence which encodes a truncated N gene protein relative to that of Table 7A is given in SEQ ID NO:5. This eDNA is 3830 bp in length, and encodes a protein of 652 amino acids (see SEQ ID NO:6).

The genomic DNA sequence containing the full-length N gene is presented in SEQ ID NO: 1. The genomic DNA is 7400 bp in length, and nucleotide sequence analysis reveals five exons, which together correspond to the coding sequence within SEQ ID NO:3. The sequence of the encoded N protein is given in SEQ ID NO:2 and SEQ ID NO:4.

Analysis of the N protein sequence and comparison to other protein sequences revealed significant sequence similarity to certain proteins involved in signal transduction (see also Table 7A and Example 5). The N gene protein contains three functional domains: a signaling domain, an ATP/GTP binding site (P-loop), and a leucine rich region. Such domains are present in proteins with roles in signal transduction.

The leucine-rich region (LRR) of N is composed of 13 repeats and contained within most of the repeats is the sequence LXXLXXLXL (or a similar sequence). In addition to the leucine residues, the presence of proline is a dominant feature of the LRRs. The LRRs we have defined are approximately 25 amino acids long on average. Proline has been arbitrarily designated to be the first amino acid in each repeat. Table 7C shows primary structure of N gene leucine rich repeats (amino acids (aa) 590–928) and comparison of its consensus sequence with LRR consensus of yeast adenylate cyclase, Drosophila Toll, human platelet membrane glycoprotein Iba chain, Htrk, Drosophila Chaoptin, Arabidopsis receptor-like transmembrane kinase (TMK1), and TMKL 1.

LRRs are thought to mediate protein-protein interactions in a wide variety of proteins. The importance of LRRs in the functions of some proteins has been determined by mutagenesis or isolation of mutations by virtue of a mutant phenotype. In yeast adenylate cyclase, mutations such as two amino acid deletions in 1 of the 26 LRRs abolishes the ability to be activated by Ras (Suzuki et al., (1990) *Proceedings of the National Academy of Science USA* 87:8711–8715). The amino acid substitution A156→V in one of 6 LRRs of the α subunit of human platelet glycoprotein 1b results in a bleeding disorder (Ware et al., (1993) *J. Clin. Invest.* 92:1213–1220).

The LRR is believed very important in governing specific protein-protein interactions. Without wishing to be bound by any particular theory, the LRR of N may interact with a component of TMV. Since small changes in LRR structure result in drastic changes in protein function, it is possible that the LRR mediates a specific interaction between TMV and the N protein. In addition, small changes in amino acid sequences could also result in new specificities which, from an evolutionary stand point, would be very beneficial to plants in evolving new resistance to ever changing pathogen populations. Another possible role of the LRRs is to interact with a specific effector molecule such as a kinase or phosphatase upon TMV recognition.

The predicted amino acid sequence of N contains a P-loop motif (Table 7A). The sequence GMGGVGKT (aa 216 to 223 of SEQ ID NO: 4) fits the P-loop consensus sequence (A/G)XXXXGK(S/T) found in various ATP- or GTP-binding proteins (Table 7A). The families of proteins containing the P-loop include adenylate kinases, ras family of proteins, elongation factors, ATP synthase b-subunit, thymidine kinases and phosphoglycerate kinases (Saraste, (1990) *Trends in Biochemical Sciences* 15: 430–434). The P-loop of N is not likely to be involved in GTP binding because the consensus sequences, DXXG and NXKD, required for GTP binding in addition to the P-loop, are not present (Dever et al. (1987) *Proceeding of the National Academy of Sciences USA* 84: 1814–1818).

In addition to the P-loop, two other "segments" appear to be involved in ATP binding in adenylate kinase and F1-ATPase (Fry et al. (1986) *Proceeding of the National Academy of Sciences USA* 83:907–911). Inspection of the N sequence suggests that these segments are present and at the proper spacing (underlined amino acid residues in Table 7A). Segment 2 contains the dipeptide (I,A,L,V)(V,I) and N has the sequence AI at positions 228 and 229, respectively. At 80–100 amino acids from the P-loop, segment 3 was defined as a glycine (G) followed by a stretch of 5 hydrophobic amino acids and an aspartate (D). N has the sequence VLIVLDD at amino acids 296–302. From the amino acid sequence, one cannot predict under what conditions ATP is bound or hydrolysed.

The amino terminal amino acids (8 to 150) of the N protein are similar to the cytoplasmic (signaling) domains of the Drosophila Toll protein and human Interleukin 1-receptor (IL-1R). The alignments are shown in Table 7B. The enclosed amino acids indicate regions where sequence identity or conservative substitutions are observed. The N sequence contains some of the conserved amino acids which are required for transmission of signal from cytoplasm to the nucleus in Toll and IL1-R regulatory pathways (Schneider et al. (1991) *Genes and Development* 5: 797–807; Heguy et al. (1992) *J. of Biological Chemistry* 267: 2605–2609).

Figure 5:
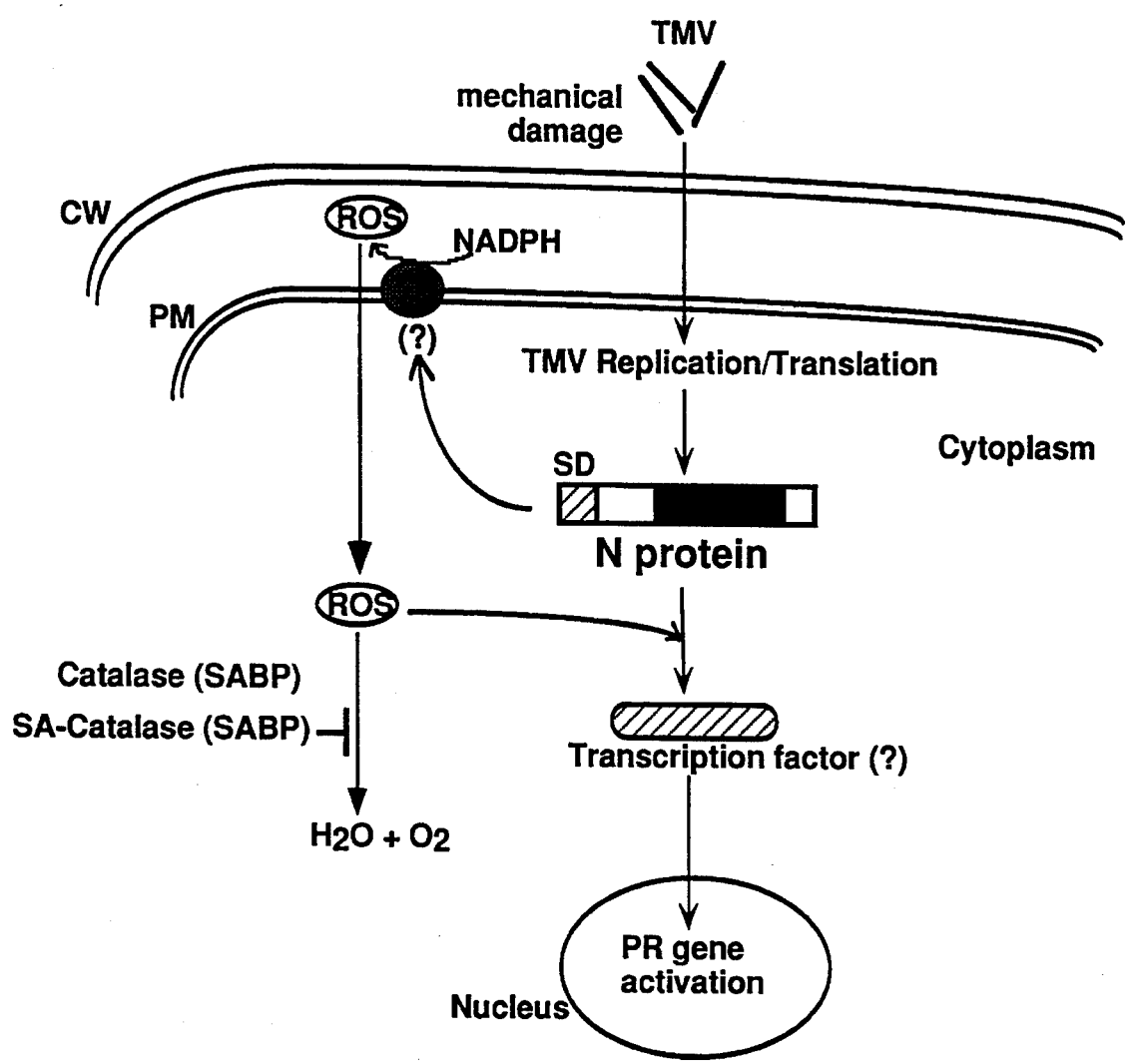
FIG. 5 is the model for N protein mediated signal transduction in response to TMV infection.

The sequence similarity between amino terminus region of N protein and the cytoplasmic domain of Drosophila Toll and human IL-1R leads to the speculation that upon TMV infection N may be triggering the similar type of intracellular signal transduction cascade (FIG. 5). Interaction of a variety of agents like viruses, cytokines (IL-1, TNF) and mitogens (phorbol 12-myristate 13-acetate, PMA), lectins, and calcium ianophores with interleukine-1 receptor (IL-1R) or perception of unknown signal by extracellular domain of Toll results in the activation and translocation of Rel-related transcription factors NFkB and dorsal respectively from cytoplasm to the nucleus. In mammalian immune, inflammatory and acute phase responses, the active transcription factor complex NF-kB induces or represses synthesis of variety of defense and signalling proteins after binding to the decameric sequence motif called the kB binding motif (reviewed in Baeuerle, (1991) *Biochimica et Biophysica Acta* 1072:63–80). These induced proteins initiate general cell defense mechanism by signalling the presence of pathogens to other cells (Baeuerle and Baltimore, (1988) *Science* 242:540–546 and Baeuerle, (1991) supra). Whereas in Drosophila embryo, the higher concentration of dorsal protein in the nucleus regulates the transcription of zygotic genes involved in the determination of dorsoventral polarity of the embryo (reviewed in Johnston and Nusslein-Volhard, *Cell* 68:201–219 (1992)). Point mutations in the signaling (cytoplasmic) domain of natural recessive alleles of Toll (Schneider et al. (1991) supra) and site-directed point mutations in the signaling domain of IL1-R (Heguy (1992) supra) resulted in a failure to translocate either dorsal or Nf-kB respectively to the nucleus.

Recently another rel-containing gene called Dif (dorsal-related immunity) involved in Drosophila immune response has been reported (Ip et al., *Cell* 75:753–763 (1993)). Similar to NFkB and dorsal, the Dif protein is normally present in the cytoplasm of the larval fat body; upon injury or infection it translocates into the nucleus and specifically binds to kB like motifs in the promotor region of various anti-microbial genes (Sun et al., *European Journal of Biochemistry*, 196:247–254 (1991); Engstrom et al., *Journal of Molecular Biology* 232:327–333 (1993); and Kappler et al., *EMBO J* 12:1561–1568 (1993)). Analogous to the above-mentioned immune and developmental responses, and without wishing to be bound by any particular theory, a product of TMV (elicitor) binds to the LRR or other region of N protein (receptor) in cytoplasm or through other unknown protein ultimately activating rel/kB like transcription factor complex, required for the induction of pathogen related (PR) genes.

One of the primary advantages of the invention is that it can provide a method to induce resistance to TMV in tobacco and related plants such as tomato and pepper. This is advantageous because N mediated resistance to TMV is highly effective and has not yet been overcome by common strains of TMV.

The cloned natural resistance gene N offers advantages over currently available techniques for protecting plants from TMV. Two genes widely used to obtain resistance to TMV are derived from the TMV coat-protein (CP) or polymerase gene. Disadvantages of the current TMV protection technology are that CP-mediated resistance may breakdown over time or with higher virus inoculum level, and polymerase-mediated resistance is very specific to the virus strain from which the polymerase gene is derived.

Another major concern of viral gene derived resistance is the risk or possibility of evolution of hyperstrains of viruses through recombination between the natural strains and the transgenes. Introducing the cloned plant viral resistance gene into commercial cultivars by transformation avoids the above-mentioned disadvantages. The N gene of tobacco confers resistance to all known strains of TMV except one.

The cloned natural plant virus resistance gene also permits fundamental studies on the mechanism of resistance gene-pathogen recognition and the signaling of the induction of defense responses so as to identify critical functional domains of the gene and to facilitate engineering of resistance genes with broader spectrums of resistance. This is the first description of a plant resistance gene whose protein sequence predicts a putative ATP/GTP binding site motif (P-loop), and a leucine rich region and signaling domain.

Cloning of the N gene was carried out by transposon tagging with the maize transposon Ac in *N. tabacum*. A positive selection was developed to isolate Ac induced mutants unable to respond to TMV with an HR (HR-mutants). One of the 36 HR- mutants carrying Ac had an unstable mutation that correlated with the presence of a single Ac transposon, designated Ac10. Genomic DNA sequences flanking Ac10 were used to screen cDNA and genomic DNA libraries for clones containing full-length cDNAs and genomic DNAs of the N gene. A genomic clone containing the N gene was isolated from a *N. glutinosa* genomic library for use to transform plants to impart resistance to TMV. The N gene was cloned into a vector, and used to transform TMV susceptible plants. The transformed plants demonstrated resistance to TMV.

As used herein, a nucleic acid molecule can be a DNA molecule, an RNA molecule or a DNA-RNA hybrid molecule. A non-naturally occurring nucleic acid molecule is one which does not occur in nature. A non-naturally occurring nucleic acid molecule, includes, for example, DNA sequences, in isolated and purified form; a recombinant nucleic acid molecule having a heterologous region, that is, an identifiable segment of DNA that is not covalently linked to the N gene coding sequence in nature; or such a non-naturally occurring molecule may be constructed of parts which have been chemically synthesized; a construct where the coding sequence itself is not found in nature, for example, a cDNA where the genomic coding sequence contains introns; or a synthetic sequence having codons different that the native gene. Parts from heterologous sources may be joined by any means known to the art, e.g., by ligation in vitro. Alternatively, parts may be joined by an in vivo process such as by recombination, but such recombination will be directed by the hand of man and the desired result will be identified by man.

Exemplary DNA molecules are the *Nicotiana glutinosa* N gene cDNAs identified by the nucleotide sequence given in SEQ ID NO:3 and the nucleotide sequence given in SEQ ID NO:5. The genomic nucleotide sequence containing the full-length *N. glutinosa* N gene is given in SEQ ID NO: 1.

Also encompassed by the invention are nucleic acid molecules comprising an N gene which has a nucleotide sequence with at least about 70% nucleotide homology with SEQ ID NO: 1 from about nucleotide 1 to about nucleotide 7400 and wherein the N gene protein encoded by the molecule has the function of mediating resistance to TMV in a plant synthesizing that N gene protein. The present invention also encompasses nucleic acid molecules comprising an N gene protein coding sequence wherein the coding sequence has at least about 70% nucleotide sequence homology with SEQ ID NO:3 from nucleotide 60 to nucleotide 3494, wherein the encoded N protein has the function of mediating TMV resistance in a plant expressing that protein. Homologous sequences encompassed by the invention can be identified in a Southern hybridization experiment using conditions wherein hybridization is due to at least about 70% homology, as opposed to nonspecific binding (see Example 2 for a discussion of stringent and non-stringent conditions). Homology is defined to mean that the nucleotides match over the defined length of a selected region. Hybridization conditions are described in Sambrook et al., *Molecular Cloning: A Laboratory Manual*, Cold Spring Harbor Laboratory (1989) and Ausubel et al., *Current Protocols in Molecular Biology*, Current Protocols (1989), which are herein incorporated by reference.

To identify an N gene from other Solanaceous species, genomic DNA from a plant of the family Solanaceae is isolated as described. The isolated DNA is cut with one or more restriction enzymes cloned in λ or other suitable vectors, electrophoresed, and blotted on to a nylon membrane such as Nytran. The blots are probed with a probe described herein. A genomic library made from these DNAs is screened using the above-named probes to identify an N gene. Activity of the gene is assessed, determined by expressing the gene in a solanaceous plant and assessing resistance of the transformed plant to TMV, as described in detail below.

Oligonucleotides derived from N gene sequence can also be used as primers in polymerase chain reaction (PCR). Tobacco contains one genomic region encoding N proteins. The conserved regions in the N gene are useful in the design of primers to mediate the recovery of functional N homolog genes in solanaceous plants. Further, antibodies raised against the domains of N protein can be used to screen expression libraries of other solanaceous plants.

A DNA coding sequence of N gene protein can also be prepared synthetically from degenerate oligonucleotides whose sequence contains codons for the amino acid sequence of N gene protein. Such oligonucleotides are prepared by standard methods and assembled and used to isolate the desired N gene.

The availability of the tobacco nucleic acid molecules encoding N gene protein makes accessible N gene sequences encoding N gene protein or functional homologs from other solanaceous plants. The tobacco genomic or cDNA sequences or portions thereof are used as oligonucleotide probes to hybridize to the additional genomic or cDNA sequences by hybridization under standard conditions. Sequences which hybridize specifically to an N gene coding sequence or its complement as described above and which encode an N functional homolog gene protein which mediates resistance to TMV in a plant of the Solanaceae family are encompassed by the invention. Such probes include those containing a complete N gene and those containing one or more of the following domains: 5' and 3' untranslated regions; signalling domain (aa 8 to 150); leucine rich repeat region (aa 591–929). Such oligonucleotides are prepared by standard methods and assembled by procedures known to those is the art. The length of the probe employed must be sufficient to hybridize to homologous regions of DNA wherein hybridization is due to at least about 70% homology, as opposed to nonspecific binding. Examples of DNA sequence useful as oligonucleotide probes are given in Example 5, below.

A specifically exemplified *Nicotiana glutinosa* N gene protein is characterized in terms of its amino acid sequence in SEQ ID NO:4, and the corresponding specifically exemplified coding sequence is provided in SEQ ID NO:3, from nucleotide 60 to nucleotide 3494.

It is well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Supplement 3, Chapter 22, pages 345–352, which is incorporated by reference herein, provides frequency tables for amino acid substitutions which can be employed as a measure of amino acid similarity. Dayhoff's frequency tables are based on comparisons of amino acid sequences for proteins having the same function from a variety of evolutionarily different sources.

The amino acid sequence of the protein may or may not be identical with the amino acid sequence which occurs naturally in solanaceous plants. The identity of an N gene protein can be confirmed by its ability to mediate resistance to TMV in a plant or plant cell synthesizing N gene protein. Such an assay is described in Example 1, below. In brief, the sequence encoding N gene protein is transformed into a plant or plant cell having the ability to synthesize N gene protein, from said sequence, e.g., a plant of the family Solanaceae. The transformed plant or plant cell is infected with TMV. The plant is observed for the presence of hypersensitive response. If resistance is observed, then the protein has the ability to mediate resistance to TMV. In addition, artificially induced mutations can be included so long as they do not destroy activity. A "mutated N protein" refers to a protein which has this activity, but which is derived by mutation of a DNA encoding an N protein. By "derived from mutation" is meant both direct physical derivation from a DNA encoding the starting material N gene protein using, for example, site specific mutagenesis or indirect derivation by synthesis of DNA having a sequence related to, but deliberately different from, that of the N gene. As means for constructing oligonucleotides of the required length are available, such DNAs can be constructed wholly or partially from their individual constituent nucleotides.

As discussed above, the availability of tobacco sequences encoding N gene protein make accessible functional homologs of N gene from other solanaceous plants, that is, a gene which has a portion encoding an "N-like" protein is defined as a polypeptide which has the function of mediating resistance to a viral plant pathogen, such as TMV. These N-like genes can be identified and isolated by virtue of their DNA sequence similarity (homology) to the tobacco N coding sequence provided herein. cDNA and/or genomic libraries can be screened by hybridization for significantly homologous sequences. These sequences can then be sequenced to ensure the presence of complete open reading forms, cloned into a plant vector so as to be expressible in a plant, and plant tissue can be transformed. Transgenic plants can be prepared using art known-techniques, and these transgenic plants can be tested to confirm that resistance to a pathogen has been gained due to the introduced N-like protein coding sequenced. N-like genes include L gene from pepper, Tm2 and Tm2a from tomato, and N' from *Nicotiana sylvestris*.

Another aspect of the invention is genetically engineered recombinant nucleic acid molecules, i.e., non-naturally occurring nucleic acid molecules, preferably DNA, containing a portion encoding an N gene protein or functional N gene homolog, which have the function of mediating resistance to TMV in a plant synthesizing N gene or functional homolog, respectively. A recombinant DNA molecule refers to a hybrid DNA sequence comprising at least two DNA sequences, the first sequence not normally being found together in nature with the second. Such molecules can be obtained by manipulation of genetic material using restriction enzymes, ligases, and similar recombinant techniques as described by, for example, Sambrook et al., supra, Ausubel et al., supra, and *DNA Cloning: A Practical Approach*, Volumes I and II (ed. D.N. Glover) IRL Press, Oxford, 1985. Examples include recombinant vectors, such as cloning or expression vectors which contain a DNA sequence encoding N gene protein which is in a 5' to 3' (sense) orientation or in a 3' to 5' (antisense) orientation. Example 7, below, describes preparation of an N gene recombinant DNA molecule. "Recombinant," as used in the present application, does not refer to naturally-occurring genetic recombinations.

Genetically engineered means that the result has been directed by the hand of man. A plant genetically engineered to contain a particular DNA molecule is one into which the DNA has been introduced by any means known to the art, including but not limited to Agrobacterium-mediated transformation, electroporation, particle bombardment, and the like. A genetically engineered nucleic acid molecule, such as a genetically engineered DNA molecule, is one which is the product of molecular biological process including but not limited to DNA ligation, in vitro mutagenesis or the like.

The DNA sequences of the invention are useful to prepare recombinant DNA expression molecules by cloning the sequence in any suitable expression vector that is capable of introducing a foreign gene into a heterologous host such as a bacterium, a yeast, a virus or its host organism, or in plants. The recombinant vector is constructed so that the coding sequence is located in the vector with the appropriate control sequence and operationally associated therewith, that is, the positioning and orientation of the N gene DNA coding sequence with respect to the control sequences are such that the coding sequence is transcribed under the control of the control sequences (i.e., by RNA polymerase which attaches to the DNA molecule at the control sequences). The control sequences may be ligated to the coding sequence prior to insertion into a vector. Alternatively, the coding sequence can be cloned directly into an expression vector which already contains the control sequence and an appropriate restriction site downstream from the control sequence. The vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the N gene coding sequence once inserted. The vector should be selected to provide a region which codes for a ribosomal binding site recognized by the ribosomes of the host cell into which the vector is to be inserted.

A recombinant DNA expression molecule containing a sequence which encodes N gene protein in the 5' to 3' orientation is inserted into a host cell for expression of N gene protein. A variety of expression systems and hosts are known in the art for production of a protein. An exemplary prokaryotic host is *Escherichia coli*. A large number of recombinant systems have been developed for expression in eukaryotic hosts, including yeast, insect cells, mammalian cells, and plant cells. These systems are well characterized, and require the ligation of the coding sequence under the control of a suitable transcription initiating system (promoter) and, if desired, termination sequences and enhancers. For production of N gene protein, host cells transformed by a recombinant DNA expression molecule are grown, and the protein isolated from the host cells. The selection of appropriate growth conditions and recovery methods are within the skill of the art.

The following exemplifies expression of N gene protein in *Escherichia coli*. The N gene DNA coding sequence is inserted into an expression vector such as pRSET (Invitrogen Corp., CA) or pET (Novagen, WI). The N gene protein coding sequence is then expressed under control of strong bacteriophage T7 transcription and translation signals. Especially useful in connection with the N genes of the present invention are expression systems which are operable in plants. The coding sequence for N gene protein and the DNA which represents the reverse transcript of the mRNA that is subsequently translated into N gene protein can be included in expression systems suitable for plants. For expression in plants, the recombinant expression cassette will contain in addition to the N gene coding sequence, a plant promoter region (if the sequence lacks one), a transcription initiation site (if the coding sequence to be transcribed lacks one), and a transcription termination sequence. The termination region may be obtained from the same gene as the promoter sequence or may be obtained from different genes. Unique restriction enzyme sites at the 5' and 3' ends of the cassette are typically included to allow for easy insertion into a pre-existing vector. Plant expression systems can be systems which are under control of a tissue-specific promoter, as well as those which involve promoters that are operable in all plant tissues.

Transcription initiation regions, for example, include the various opine initiation regions, such as octopine, mannopine, nopaline and the like. Plant viral promoters can also be used, such as the cauliflower mosaic virus (CaMV) 35S promoter. In addition, plant promoters such as ribulose-1,3-diphosphate carboxylase, fruit-specific promoters, heat shock promoters, seed-specific promoters, etc. can also be used. The particular promoter selected should be capable of causing sufficient expression to result in the production of an effective amount of the N gene protein to render the plant cells and plants regenerated therefrom resistant to infection by TMV. The CaMV 35S promoter has been shown to be highly active in many plant organs and during many stages of development when integrated into the genome of transgenic plants. Tissue-specific promoters are also well known.

Preferably, in molecules directing the expressing of TMV resistance via the N gene, transcription termination signal(s) are provided downstream of and operably linked to the N gene protein coding region. The termination signal may be that normally present within the N gene, or one or more heterologous transcription termination signals may be provided downstream of the N coding region. A number of transcriptional termination signals are well known to the art, for example those of *Agrobacterium tumefaciens* T-DNA genes including but not limited to nos.

The resulting expression system or cassette is ligated into or otherwise constructed to be included in a recombinant vector which is appropriate for plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

TMV resistance mediated by the N protein has been demonstrated in transgenic plants into which a genomic N clone has been introduced, where the plant was TMV-sensitive prior to genetic modification. Clone of cDNA encoding the N protein can also be used to confer TMV resistance in sensitive solanaceous plants. The cDNA is cloned downstream of and operably linked to a promoter functional in plant cells and introduced into plant tissue, and then transgenic plants are regenerated using vectors and techniques readily accessible to the skilled artisan. Vital resistance is confirmed by test innoculation with the challenge virus, e.g., TMV. It may be useful when using cDNA, to introduce both the full length (SEQ ID NO:3) and the truncated (SEQ ID NO:5) cDNAs into plant tissue after operably linking each sequence to transcriptional control sequences functional in plant cells. Again, TMV resistance is confirmed by TMV innoculation testing.

Other DNA sequences encoding additional functions may also be present in the vector, as is known in the art. For instance, in the case of Agrobacterium transformations, T-DNA sequences will also be included for subsequent transfer to plant chromosomes.

When an appropriate vector is obtained, transgenic plants are prepared which contain the desired expression system. The N gene protein coding sequences are inserted into a suitable plant transformation vector for transformation in the desired plant species, notably, a plant of the family Solanaceae, to render the plant resistant to TMV. In addition to tobacco (Nicotiana, e.g., *N. tabacura* and *N. glutinosa*), prominent food crops are in the Solanaceae family. These include tomato (Lysopersicon, e.g., *L. lycopersicum* and *L. esculentum*); pepper (Capsicum); potato (*Solanum tuberosum*); eggplant (*Solanum melongena*).

A number of techniques are known in the art for transformation of plants or plant cells. For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (J. Schell, *Science* 237:1176–1183 (1987)). Ti and Ri plasmids contain two regions essential for the production of transformed cells.

Construction of recombinant Ti and Ri plasmids in general follows methods typically used with the more common bacterial vectors, such as pUC 19. There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ 1 shuttle vector of DeBlock et al., *EMBO J* 3:1681–1689 (1984) and the non-oncogenic Ti plasmid pGV3850 described by Zambryski et al., *EMBO J* 2:2143–2150 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* 12:8711–8721 (1984) and the non-oncogenic Ti plasmid PAL4404 described by Hoekema et al., *Nature* 303:1.79–180 (1983). Some of these vectors are commercially available.

There are two common ways to transform plant cells with Agrobacterium: co-cultivation of Agrobacterium with cultured isolated protoplasts and transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants. Most dicot species can be transformed by Agrobacterium as all species which are a natural plant host for Agrobacterium are transformable in vitro.

Another procedure for cloning and transformation involves cloning the N gene coding sequence into T-DNA vector pMD1 between the CaMV 35S promoter and NOS terminator region. Plants bearing germinal Ac excision events are transformed according to Horsch et al. *Science* 227:1229–1231 (1985) with modifications (Hehl, *Molecular General Genetics* 217:53–59 (1989)). This procedure is described in detail in Example 1, below.

*Agrobacterium tumefaciens* mediated transformation is known to be effective with members of the Solanaceae family of plants and is particularly useful. Other transformation methods such as electroporation, microprojectile or particle gun technology, liposomes, and chemicals that increase free DNA uptake may also be used. Identification of transformed cells or plants is generally accomplished by including a selectable marker in the transforming vector, or by obtaining evidence of successful bacterial infection. Plant cells which have been transformed can also be regenerated using known techniques.

Regeneration of plants of the family Solanaceae is described in detail in Horsch et al., 1985, supra. Plant regeneration from cultured protoplasts is described in Evans et al., *Handbook of Plant Cell Cultures*, Vol. 1: (MacMillan Publishing Co. New York, 1983); and Vasil I.R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. Efficient regeneration will depend on the medium, on the genotype, and on the history of the culture. If these three variables are controlled, then regeneration is usually reproducible and repeatable. The regenerated plants are transferred to standard soil conditions and cultivated in a conventional manner.

After the expression cassette is stably incorporated into regenerated transgenic plants, it can be transferred to other plants by sexual crossing. Any of a number of standard breeding techniques can be used, depending upon the species to be crossed. The plants are then grown and harvested using conventional procedures.

EXAMPLES

The following examples are intended only to further illustrate the invention and are not intended to limit the scope of the invention as claimed. The examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218; Wu et al. (eds.) *Methods in Enzymology* 100, 101; Glover (ed.) ( 1985); *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include Kung and Arntzen (eds.) (1989) *Plant Biotechnology*, Butterworths, Stoneham, MA; R. A. Dixon (ed.) (1985) *Plant Cell. Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) Academic Press, San Diego, Calif.; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1989) *Plant Mol. Biol.* 13:273; Walden and Schell (1990) *Eur. J. Biochem.* 192:563; Joersbo and Brunstedt (1991) Physiol. Plant. 81:256 and references cited in those references. Abbreviations and nomenclature, where employed, are deemed standard in the field and are commonly used in professional journal such as those cited herein. All references cited in the present application are expressly incorporated by reference herein.

EXAMPLE 1

This example describes the isolation of an unstable HR-mutant. In brief, mutations of the N locus were isolated by transposon tagging using the maize transposon Ac. Next, mutants unable to mount a TMV-dependent HR were isolated using a positive selection scheme which selected TMV-infected N bearing plants that lost the ability to mount TMV dependent HR (HR-mutants). Plants homozygous for their HR- mutations were identified, and a mutant line having an unstable HR- was identified.

The U 1 strain of TMV (gift of M. Zaitlin) was propagated in the TMV susceptible (nn) tobacco cultivar (cv.) Petite Havana SR1, termed SR1 tobacco. Except for the inoculations performed for the mutant screen (see below), TMV inoculations were performed as follows: Inoculum was prepared by diluting the sap of macerated, TMV infected SR1 tobacco leaves ~10 fold in sterile water. A sponge saturated with the sap solution was used to rub the upper leaf surfaces of the plants at the six leaf stage. Plants were scored after 48 hours for local lesions and at intervals of 1 week post inoculation for signs of systemic infection (mosaic) and/or sectors of necrosis.

To isolate transgenic tobacco bearing active Ac transposons, TMV resistant tobacco, cv. Samsun NN. was transformed with pGV3850 HPT::pKU3 (Baker et al., *The EMBO Journal* 6:1547–1554 (1987)) according to Horsch et al. (*Science* 227:1229–1231 (1985)) using a modified procedure (Hehl and Baker, *Mol. Gert. Genet.* 217:53–59 (1989)). The pGV3850 HPT::pKU3 transformation vector carries the neomycin phosphotransferase II (NPTII) interrupted by Ac. After introduction of pGV3850 HPT::pKU3 into tobacco, Ac excises from the defective NPTII gene, resulting in NPTII expression and the growth of transformants on kanamycin containing medium.

In brief, leaf discs were prepared from sterile 6 to 8 week old TMV resistant tobacco, cv. Samsun NN plantlets grown on MS medium. Leaf discs were incubated in the presence of *Agrobacterium tumefaciens* containing pGV3850HPT:pKU3 or control Ti plasmid vectors for 2 to 4 days. Leaf discs were rinsed in MS medium containing 3 % sucrose and 500 mg/l Cefotaxime (CalbioChem, La Jolla, Calif.) and placed on MS medium containing 3% sucrose, 0.5 mg/l BAP (6 benzylaminopurine), 0.1 mg/l NAA (naphthalene acetic acid), 500 mg/l Cefotaxime and 200 mg/l kanamycin or 20 mg/l hygromycin. After 2 to 3 weeks, shoots were subsequently transferred to the same medium but containing 2 mg/l BAP. After 1 to 2 weeks the shoots were transferred again to the same medium but without hormones for root induction. The plants were transferred to the soil after 10 to 15 days. Transgenic calli were regenerated on 100 mg/l kanamycin to select for transgenic tissue harboring transposing Ac elements (Baker et al., 1987, supra). Genomic DNA was isolated from KnR primary transgenics, termed the TO generation.

Ac was determined to be very active in plant T0-3(pGV3850 HPT::pKU3) based on resistance to 100 mg/l kanamycin and the increase in Ac copy number as determined by Southern hybridization. Plant TO-3 was crossed to Samsun NN. Three T1 progeny derived from the cross, T1-9, 10, 13 determined to have transposing Ac elements were crossed to the TMV susceptible (nn) tobacco cultivar Petite Havana SR1 (SR1) to generate three F1 Nn::Ac populations to screen for loss of the TMV dependent hypersensitive response. To establish the endogenous instability of N, an Nn population without Ac was also generated by crossing Samsun NN and SR1. SR1 was used as the pollen donor in all crosses.

To isolate HR- mutants, approximately 64000 Nn: :Ac and 29000 Nn seeds (see Table 1) were sown at a rate of ~2000 seeds/flat with a density of ~3 seedlings/cm². Eight week old seedlings were placed at 30° C. and inoculated with a suspension of TMV and Celite (Fisher, Pittsburgh, Pa.) using an artist air brush (Paasche VL) (R. W. Fulton, *Nicotiana: Procedures for Experimental Use* pages 79–86 (1979)). The concentration of TMV was sufficient to give local lesions at an apparent density of 1.0/cm² on Samsun NN seedlings planted at a density of ~3/cm² and kept at 24° C. TMV was isolated from infected SR1 leaves according to Lane (*Methods in Enzymology* 118:687–691 (1986)). At three days post-inoculation (dpi), seedlings were transferred from 30° C. to 21° C. At 5 dpi, seedlings were scored for survival, then the second of three cycles of TMV inoculations and temperature shifts was begun to ensure a 100% inoculation rate.

TABLE 1

Isolation of HR- Mutants

| Cross | Plants screened | HR- mutants | Frequency[a] |
|---|---|---|---|
| Samsun NN × nn | 29000 | 11 | $3.8 \times 10^{-4}$ |
| T1-9[b], −10[b], and −13[b] × nn | 64000 | 36 | $5.6 \times 10^{-4}$ |
| Total | 93000 | 47 | $5.0 \times 10^{-4}$ |

[a]The frequency is calculated by dividing the number of HR- plants by the total number of F1 plants screened for each cross.
[b]Samsun NN plants bearing active Ac transposons Two plant pathogenic bacteria, *Pseudomonas syringae* pv. tomato (P.s.t.) strain DC3000 and P.s. pv. *phaseolicola* (P.s.p.) strain NP 53121, and the non-pathogenic P.s.t. strain DC 3000 hrpS::Tn5 (gifts of B. Staskawicz) were suspended in double distilled $H_2O$ at a concentration of $1 \times 10^8$ cells per ml. Each bacterial suspension or water control was injected with a 10 ml syringe and 20 gauge needle (Z. Klement, In *Methods in Phytobacteriology* (Ed. Klement et al.) Akdemiae Kiado, Budapest, Hungary, 101–102 (1990)) into one of four sites on the underside of a single leaf. Three plants from each of the following genotypes were used: Nt-1G/g selfed offspring of 9 HR-mutants, two TMV sensitive (SR1 and Xanthi) and two TMV resistant (Samsun NN and Xanthi nc) tobacco cultivars. Leaves were scored for their response to the four different treatments at 48 hours post inoculation.

The positive selection scheme allows the isolation of mutants unable to mount a TMV dependent HR among large populations of Nn seedlings. The mutant selection scheme exploits the suppression of HR expression on N bearing plants when infected with TMV and held at temperatures above 28° C. Plants carrying a functional N gene do not form local lesions at temperatures above 28° C. and TMV spreads systemically throughout the plant. Suppression of the HR is reversible, and TMV infected plants carrying N develop lethal systemic necrosis (systemic HR) when the temperature is lowered to the permissive 24 ° C. This is a positive mutant selection because only plants that have lost the ability to mount TMV dependent HR (HR- mutants) are expected to survive.

Forty-seven HR- mutants were thus isolated from heterozygous (Nn) F1 seedlings produced from four independent crosses between Samsun NN or three NN::Ac parents and SR1 tobacco. The TMV infected HR- plants were obtained from a total of 93,000 F1 seedlings. Eleven mutants were isolated from 29,000 seedlings from the Samsun NN control cross, while 36 mutants were isolated from 64,000 seedlings from the three NN::Ac crosses (Table 1). The frequency of loss of resistance to TMV was similar in the Nn progeny of Samsun NN and NN::Ac at $3.8 \times 10^{-4}$ and $5.6 \times 10^{-4}$, respectively. The ability to obtain HR- mutants at a similar frequency in Nn populations with and without Ac, indicates that the endogenous mutation rate of N is very high.

To determine if the HR- mutants were defective in a general ability to mount an HR, progeny of nine mutants, including C2-2, were inoculated with two bacterial pathogens known to elicit an HR on tobacco. The pathogenic bacteria, *Pseudomonas syringae* pv. tomato (P.s.t.) strain DC 3000 and P.s. pv. *phaseolicola* (P.s.p.) strain NP 53121, elicited an HR in all cases whereas the non-pathogen, P.s.t. strain DC 3000 hrpS::Tn5, and the water control did not. These results indicated that the HR- mutants did not lack a general ability to mount an HR to a bacterial pathogen and that the HR- phenotype was probably specific to the TMV resistance response.

To identify plants homozygous for their HR- mutations, the self crossed progeny of 15 mutants were examined molecularly. DNA was isolated from 27–64 selfed progeny of each mutant, digested with EcoRI, and hybridized with the N-linked Nt-1 RFLP probe (Hehl and Baker, *The Plant Cell* 27:709–721 (1990)). Nt-1 identifies an RFLP, Nt-1G, that is introgressed into the TMV resistant tobacco cultivar Samsun NN from *N. glutinosa*. Nt-1G replaces its Nt-1T homolog in Samsun NN and maps to ≤0.25 cM of the N locus. It was assumed that the mutant lines indicated in Table 2 are homozygous for their HR- mutations because they are homozygous for the tightly linked Nt-1G marker or are homozygous for the deletion of the Nt-1G marker.

A hallmark of Ac-induced mutations is that they are often unstable. The stability of the HR- phenotype was examined in the selfcross progeny of 15 homozygous mutant lines. Ninety-five to 150 progeny of each line were inoculated with TMV and scored for their phenotype. Offspring of one mutant line, D 11–1, demonstrated instability of the HR- phenotype at a high frequency. Of the 145 D11–1 plants scored, 20 were TMV resistant ($TMV^R$) and 68 were TMV susceptible ($TMV^S$). Interestingly, fifty-seven plants displayed sectors of necrosis on a TMV susceptible background ($TMV^{R/S}$ phenotype) (Table 2). Lesion mimic mutants also display sectors of necrosis. Necrosis on lesion mimic mutants is generally expressed spontaneously in the absence of abiotic or biotic factors that elicit necrotic responses (V. Walbot et al., *Genetic Engineering of Plants* pages 431–442 (1983)). The sectors of necrosis observed in the D 1 1–1 progeny and other populations used in the studies described here are distinguishable from a lesion mimic phenotype, because they are dependent on TMV infection. Identification of $TMV^R$ and $TMV^{R/S}$ individuals in this population indicated that the HR- mutation is unstable. The $TMV^R$ and $TMV^{R/S}$ phenotypes were not observed in the offspring of the other 14 mutant lines (Table 2).

TABLE 2

Identification of an unstable HR- mutant line

| | mutant | Phenotype[c] | | | |
|---|---|---|---|---|---|
| line[a] | parent[b] | $TMV^R$ | $TMV^{R/S}$ | $TMV^S$ | Total[d] |
| D2-2 | C3-2 | 0 | 0 | 144 | 144 |
| D6-2 | C3-6 | 0 | 0 | 126 | 126 |
| D9-2 | C1-1 | 0 | 0 | 125 | 125 |
| D11-1 | C2-2 | 20 | 57 | 68 | 145 |
| D12-6 | C2-3 | 0 | 0 | 134 | 134 |
| D13-3 | C2-5 | 0 | 0 | 149 | 149 |
| D15-3 | C2-7 | 0 | 0 | 133 | 133 |
| D16-3 | C2-9 | 0 | 0 | 134 | 134 |
| D17-2 | C2-10 | 0 | 0 | 143 | 143 |
| D21-1 | C2-16 | 0 | 0 | 95 | 95 |
| D23-5 | C2-19 | 0 | 0 | 148 | 148 |
| D24-2 | C2-20 | 0 | 0 | 111 | 111 |
| D26-2 | C2-21 | 0 | 0 | 144 | 144 |

TABLE 2-continued

Identification of an unstable HR- mutant line

| | mutant | Phenotype[c] | | | |
|---|---|---|---|---|---|
| line[a] | parent[b] | TMV[R] | TMV[R/S] | TMV[S] | Total[d] |
| D27-2 | C2-22 | 0 | 0 | 150 | 150 |
| D28-2 | C2-23 | 0 | 0 | 150 | 150 |
| Samsun NN | na | 150 | 0 | 0 | 150 |
| SR1 | na | 0 | 0 | 150 | 150 | na = not applicable
[a]The lines tested in these experiments were the self progeny of F1, Nn, mutants. These plants are homozygous for the N-linked Nt-1G RFLP
[b]F1 mutant progenitor. C1-X is from T1-9 × SR1, C3-X is from T1-10 × SR1, and C2-X are from T1-13 × SR1
[c]Selfed progeny of each homozygous mutant line were germinated in flats of 50 seedlings each. Seedlings were inoculated at approximately 6 weeks of age with the U1 strain of TMV and scored at 48 hours and subsequent one week intervals post inoculation for phenotype. Samsun NN and SR1 are used as controls for the TMV[R] and TMV[S] phenotypes, respectively. Phenotypes are designated as follows: TMV[R] (TMV resistant), TMV[S] (TMV susceptible), and TMV[R/S] (TMV dependent sectors of necrosis on a TMV susceptible background).
[d]Total number of seedlings inoculated and scored for their phenotype from each mutant line.

Shown in FIG. 1 are the three different phenotypes observed in this unstable mutant line (D 11–1 progeny) following TMV inoculation. The leaf in FIG. 1A is from a TMV resistant plant and displays the characteristic lesions of a TMV resistant (HR+) wild type or revertant plant. The leaf in FIG. 1B is from a TMV susceptible plant and displays areas of light and dark green (mosaic). The leaf in FIG. 1C displays the TMV[R/S] phenotype that is defined by the areas of necrosis and mosaic. Unlike the TMV[R] leaf, necrosis of the TMV[R/S] leaf is not confined to discreet lesions. The TMV[R/S] leaf shown here displays small necrotic patches, however, plants have been observed where the necrosis can consume half-leaves, whole leaves, and be seen running up the stem. The observation of the TMV[R] and TMV[R/S] phenotypes in the progeny of D11–1 demonstrates that the HR- mutation in this mutant line is unstable.

EXAMPLE 2

This example describes tests to determine if the TMV[R/S] phenotype is due to two Ac transposons, which cosegregated with the N-linked RFLP marker Nt-1G.

Unless otherwise noted herein, for DNA—DNA hybridizations, the target DNA is purified and digested with one or more restriction endonucleases. The digested DNA is then size-fractionated by agarose gel electrophoresis, and then blotted to Nytran membrane (Schleicher & Schuell, Keene, N.H.). Hybridization probes are prepared using random hexamer primers and labeled with [$^{32}$P]-dCTP and Klenow polymerase. Standard conditions for stringent hybridization were hybridization at 42° C. in the presence of 50% formamide, 5×SSC, 5 x Denhardt's solution with washes at 65° C. using 0.1×SSC, 1% (w/v) sodium dodecyl sulfate (SDS).

Standard conditions for non-stringent hybridizations were hybridization at 35° C. using 50% formamide, 5×SSC, 5×Denhardt's solution with 50° C. washes using 0.1×SSC, 1% SDS.

Figure 2A:
FIG. 2A–2C illustrate Southern blot hybridization analysis of the probe Nt1 RFLP marker and Ac to the D 111 population.

To isolate N-linked Nt-1G RFLP, DNA fragments isolated as insertion sites of transposed Ac elements from SR1 were used for RFLP analysis (Hehl and Baker, Mol. Gert. Genet. 217:53–59 (1989), Hehl and Baker, The Plant Cell 2:709–721 (1990)). One DNA fragment, designated Nt-1, detects an RFLP between the TMV[S] tobacco cv SR1 and the TMV[R] tobacco cultivar Samsun NN. FIG. 2A shows the result of the hybridization of a 1.2 kb BglII/HindIII Nt-1 fragment to EcoRI digested genomic DNA from the three diploid tobacco species N. glutinosa (the source of the N gene), N. sylvestris, and N. tomentosiformis (FIG. 2A, lanes 1, 4, and 5) and two N. tabacum cultivars Samsun NN and SR1 (FIG. 2A, lanes 2 and 3). Nt-1 detects RFLPs specific for each of the diploid tobacco species. The 13.1 kb DNA fragment is present in Samsun NN, SR1, and N. sylvestris, (FIG. 2A, lanes 2, 3, and 4). The 15.5 kb DNA fragment is present in N. tomentosformis and SR1 (FIG. 2A, lanes 5 and 3) and the 14.3 kb DNA fragment is present in N. glutinosa and Samsun NN (FIG. 2A, lanes 1 and 2). Samsun NN lacks the 15.5 kb N. tomentosiformis RFLP (Nt-1T) but carries an RFLP identical in size with the 14.3 kb RFLP in N. glutinosa (Nt-1G).

Linkage between Nt-1G and N was tested in 420 TMV[S] F2 progeny of a cross between Samsun NN and SR1 tobacco segregating 3:1 for TMV resistance and susceptibility and 1:2:1 for the Nt-1G and Nt-1T RFLPs. DNA from TMV susceptible F2 plants was digested with EcoRI and hybridized with Nt-1. One TMV[S] plant had an Nt-1G RFLP demonstrating that Nt-1G is very tightly linked to N≦0.25 cM.

Two Ac transposons cosegregated with the N-linked RFLP, Nt-1G. If the TMV[R/S] phenotype was dependent on a mutable allele of N, it was expected to cosegregate with a molecular marker linked to the N locus. The cosegregation of the TMV[R/S] phenotype with the N-linked Nt-1G marker in the testcross progeny of the unstable HR- mutant, C2–2, and SR1 tobacco was tested. Testcross progeny (termed the D 111 population) were inoculated with TMV and scored for their phenotype. Of the 264 D 111 plants scored, 164 were TMV susceptible (TMV[S]) while 80 displayed sectors of necrosis in a TMV susceptible background. Wild type TMV resistant plants were not observed. DNA of 80 D 111 plants was digested with EcoRI and hybridized with Nt-1. The Nt-1 genotype of the plants was determined and 39 individuals were Nt-1G/T while 41 were Nt-1T/T (Table 3). The 26 plants that displayed the TMV[R/S] phenotype had the Nt-1G marker, while the Nt-1T/T plants were TMV[S] (Table 3). These results indicated that the unstable HR- mutation, defined by the ability to form necrotic sectors, was linked to Nt-1G.

Because the unstable HR- mutation was linked to Nt-1, whether an Ac transposon cosegregated with the Nt-1G RFLP marker in the D111 population was investigated. D 111 DNA digested with EcoRI was hybridized with a probe from the 5' end of Ac. Two Ac hybridizing bands, named Ac8 (8.0 kb EcoRI Ac band) and Ac10 (10.2 kb EcoRI Ac band), were found to cosegregate with Nt-1G. Thirty Nt-1G/T plants had both Ac8 and Ac10, 5 had Ac*, 3 had Ac10, and 1 plant had neither element (Table 4). Ac8 and Ac10 were not present in the 41 Nt-1T/T plants, establishing that these two Ac transposons were linked to Nt-1G.

Figure 2B:
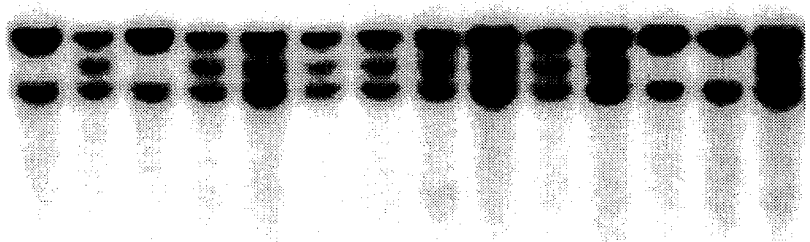
Figure 2C:
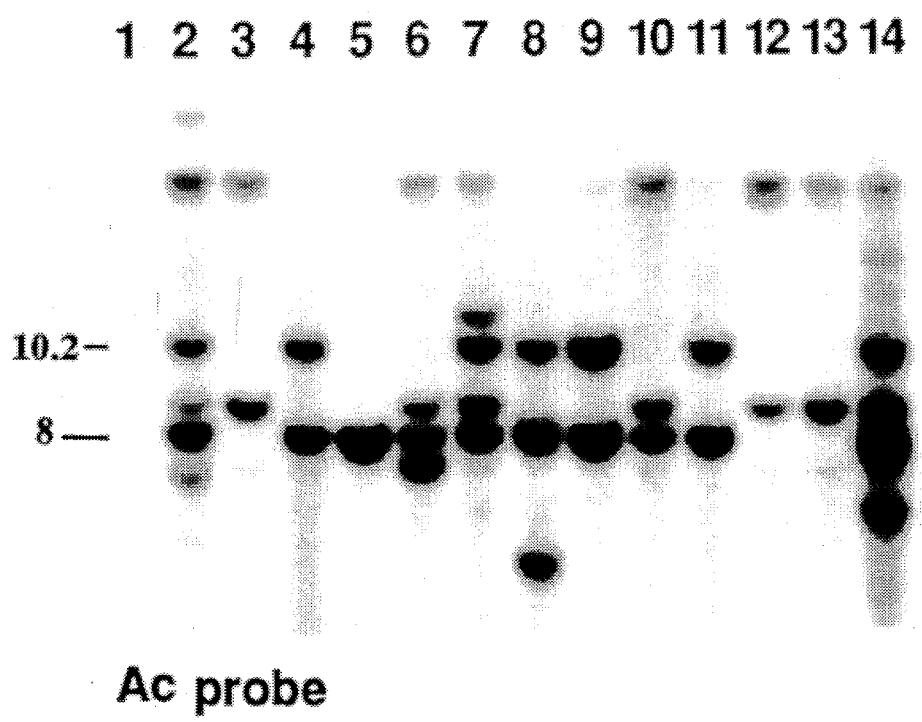

An example of the Southern hybridization data summarized in Tables 3 and 4 is shown in FIG. 2B and 2C, respectively. Displayed in FIG. 2B is hybridization of Nt-1 to EcoRI digested DNAs of 14 D 111 plants. Ten plants shown here have the heterozygous, Nn, Nt-1G/T genotype as demonstrated by the presence of the 14.3 kb Nt-IG RFLP and the 15.5 kb Nt-1T RFLP (lanes 2,4–11, and 14). Six of these plants had the TMV[R/S] phenotype corresponding to lanes 2, 4, 7, 9, 11, and 14. Four plants have the homozygous, nn, genotype Nt-1T/T genotype as demonstrated by the presence of the 15.5 kb Nt-1T RFLP and absence of the 14.3 kb Nt-1G RFLP (lanes 1, 3, 12, and 13). The four plants of the Nt-1T/T genotype did not have the $TMV^{R/S}$ phenotype. Subsequently, these DNAs were hybridized with the 5' Ac probe as shown in FIG. 2C. All 10 plants of the Nt-1G/T genotype carry the 8.0 kb Ac band (termed, Ac8) while 7 of these individuals (lanes 2, 4, 7, 8, 9, 11, and 14) carry the 10.2 kb Ac (termed, Ac10). Plants of the Nt-1T/T genotype do not contain either the 8.0 kb or the 10.2 kb Ac RFLPs, although they do carry other Ac transposons.

TABLE 3

The Unstable HR- Phenotype Cosegregates with the N-linked RFLP, Nt-1G

| Nt-1 genotype[b] | TMV Phenotype[a] | | | |
|---|---|---|---|---|
| | $TMV^R$ | $TMV^{R/S}$ | $TMV^S$ | Total |
| Nt-1G/T | 0 | 26 | 13 | 39 |
| Nt-1T/T | 0 | 0 | 41 | 41 |

[a]80 plants from the cross of the unstable HR- mutant, C2-2, and SR1 tobacco (the D111 population) were inoculated with TMV and scored for their phenotypes as described in Table 2.
[b]DNA isolated from the D111 plants was digested with Eco RI for Southern analysis with Nt-1.

TABLE 4

Two Ac transposons cosegregate with Nt-1G

| Nt-1 genotype | Cosegregating Ac bands[a,b] | | | | |
|---|---|---|---|---|---|
| | Ac10/8 | Ac10 | Ac8 | — | Total |
| Nt-1GT | 30 | 3 | 5 | 1 | 39 |
| Nt-1T/T | 0 | 0 | 0 | 41 | 41 |

[a]Following Nt-1 hybridization, Southern blots containing D111 DNAs digested with Eco RI were stripped and hybridized with the 5' Ac probe.
[b]Two Ac bands were identified that cosegregated with Nt-1G, however most plants had 3 to 8 additional copies of Ac.

EXAMPLE 3

This example describes the test to determine whether Ac8 or Ac10 is responsible for the unstable HR- mutation.

To determine whether Ac8 or Ac10 causes the unstable HR- mutation, a germinal revertant (D112-15) was identified from the selfed progeny of the HR- mutant C2-2. D112-15 was homozygous for Nt-1G and carded both Ac8 and Ac10. Because both Ac8 and Ac10 were present, it was assumed that one transposon tagged allele of N had germinally reverted to wild type while the other still contained Ac and thus had the potential to revert. D112-15 was crossed to SR1 to test whether excision of Ac8 or Ac10 could be correlated with reversion to resistance and instability of the HR- mutation. The progeny of this cross (the E501 population) were expected to segregate ~1:1 for $TMV^R$ to $TMV^S$ +$TMV^{R/S}$ and have the Nt-1G/T genotype. The Ac responsible for the unstable mutation of N was expected to be absent from all resistant offspring of this cross. Ninety-five E501 plants were inoculated with TMV and scored for their phenotype. Fifty-four were $TMV^R$, necrotic sectors were observed on 21 plants, and 20 were $TMV^S$ (Table 5). DNA from these plants was digested with EcoRI and probed with Nt-1 followed by the 5' Ac probe. All 95 plants were of the Nt-1G/T genotype. Significantly, none of the 54 TMV resistant individuals had the 10.2 kb EcoRI Ac band whereas the 8 kb band was present in 52 plants (Table 5). The presence of Ac8 and the absence of Ac 10 in the TMV resistant E501 progeny implicated Ac 10 as the element causing the unstable HR- mutation and thus tagging N.

TABLE 5

Ac10 is Correlated with the HR- mutation

| N-Linked Ac | TMV Phenotype[a,b] | | |
|---|---|---|---|
| | $TMV^R$ | $TMV^{R/S}$ | $TMV^S$ |
| Ac10 | 0 | 1 | 1 |
| Ac10/Ac8 | 0 | 18 | 1 |
| Ac8 | 52 | 1 | 18 |
| — | 2 | 1 | 0 |

[a]95 plants from the cross of the $TMV^R$ germinal revertant, D112-15, and SR1 tobacco (the E501 population) were inoculated with TMV and scored for their phenotype as described in Table 2.
[b]DNA isolated from the E501 plants was digested with Eco RI for Southern analysis and hybridized with the 5' Ac probe.

The Ac copy number is high in the D 111 and E501 populations which could mask, perhaps, other Ac elements cosegregating with Nt-1G. A $TMV^S$ plant, E501-70, was identified that had only the Ac10. To confirm that Ac10 alone could cause the unstable HR- mutation, selfed progeny of this plant (the F501 population) were examined for their phenotypes following TMV infection and analyzed for the presence of Ac10 and their Nt-1 genotypes. Seven $TMV^R$ plants were recovered from 500 total plants. Molecular analysis showed that three $TMV^R$ plants were heterozygous for Nt-1G and did not have Ac10 hybridization while four $TMV^R$ plants were Nt-1G/G and had the Ac10 band. As with the D112-15 plant, it was assumed that the Ac hybridization in the Nt-1G homozygotes was due to the presence of a mutant allele of N in these plants as well as the revertant one.

In the E501 and F501 populations there is a correlation between the presence of Ac10 and the $TMV^{R/S}$ phenotype. Nineteen of 21 E501 plants of the $TMV^{R/S}$ phenotype had Ac10 hybridization, 12 of 12 F501 $TMV^{R/S}$ plants analyzed molecularly had the 10.2 kb Ac band. These results indicated that the presence of Ac10 is necessary for plants to form the sectors of necrosis and maintain the potential to revert somatically to resistance. Tissue from sectored plants without Ac10 hybridization probably have more excision, so that the 10.2 kb Ac band is no longer detectable by Southern blot hybridization.

In the D111 and E501 populations, a 2.3 kb EcoRI band that hybridized to a 3' Ac probe behaved identically to the 10.2 kb 5' Ac band. Given that Ac is 4.6 bp, an EcoRI wild type or excision fragment of 7.9 kb is predicted. This fragment was expected to be restored in $TMV^R$ revertants. To test for the presence of the genomic insertion and excision fragments, the genomic sequences flanking Ac10 were isolated by IPCR from plant D111-95 that contained only Ac10 and Ac8 (FIG. 2C, lane 9). (See Example 4 below.)

Genomic sequences flanking Ac10 were isolated by the inverse polymerase chain reaction (IPCR). Template DNA from plant D 111-95 that carried only Ac8 and Ac10 was digested with HpaII, ligated and linearized with ClaI. PCR reactions were carried out in 50 µl using Taq polymerase (Promega, Madison, Wis.) on a Perkin-Elmer Thermocycle (Emeryville, Calif.). The parameters were 94° C.-1 min., 55° C.-1 min., and 72° C.-2 min. for 35 cycles. A 419 bp product (Ac10-1) 5' to Ac10 was amplified using Ac specific primers CC28 (5'-CACGGATCCATACGATAACGGTCGG-TACGGGA-3') and CC32 (5'-CACGAATTCGGAAACG-GAAACGGTAGAGC-3'). To obtain the Ac10 3' flanking sequence (Ac10-2), D111–95 DNA was digested with EcoRI, ligated and linearized with AccI. A 122 bp product was amplified using primers CC21 (5'-CACCTGCAGAGATCTTTACCGACCGTTACCGACCG) and CC30 (CACCTGCAGAGATCTGCAGGCTTATAATATAAGGC-3'). IPCR products were cloned into the TA Cloning Vector (Invitrogen, San Diego, Calif.).

A 400 bp IPCR product from the 5' end of Ac was isolated (Ac10-1). Ac10–1 was cloned into the TA cloning vector and sequenced. PCR primers were synthesized to generate an Ac10–1 probe with no Ac sequences to reduce the possibility of spurious Ac hybridization. When used as a probe on tobacco genomic DNA, Ac10-1 detected repetitive sequences. Hybridization to the 10.2 kb Ac insertion band was observed in the DNA of D11-1; however, the predicted 7.9 kb EcoRI excision band was not discernable due to the repetitive nature of the probe. The IPCR clone obtained from the 3' end of Ac10 (Ac10–2) was 1118 bp in length and appeared unreliable as a probe.

A reliable, low copy number probe, N-5, was obtained from the 3' end (bases 5020 to 5370) of cDNA clone C7. This corresponds to bases 6587–6600, 6934–6948, and 6977–7270 of SEQ ID NO: 1. Molecular analyses of the E501 and F501 populations was continued using the restriction endonuclease EcoRI. DNA from the ES01 and F501 populations were digested with EcoRI and hybridized with Ac and N-5 probes. The Ac probe hybridized to a 10.2 kb EcoRI band corresponding to Ac 10 in the ES01 and F501 populations. Ac hybridization to selected individuals from each generation in the unstable HR-mutant line is shown in FIG. 3C. Ac hybridization was not observed in the control DNAs of SR1, *N. glutinosa*, or Samsun NN. The original HR- mutant C2-2 has a 10.2 kb Ac band in addition to at least two other Ac transposons. The germinal revertant, D112-15, has the 10.2 kb Ac band as well as at least 10 other Acs. E501-70, the TMV$^S$ offspring of D112-15, has only the 10.2 kb Ac10 band. Two germinal revertant TMV$^R$ offspring of E501-70, F501-65, and F501-66, do not have the 10.2 kb band. F501-65 has a new Ac insertion while F501-66 no longer has Ac hybridization. The sectored plants F501-2, 3, and 4 all still have Ac10 insertion. F501-48 and F501-64 are two examples of TMV$^S$ plants that also no longer have Ac10 hybridization. F501-48 no longer has Ac hybridization whereas F501-64 has a new insertion.

Figure 3A:
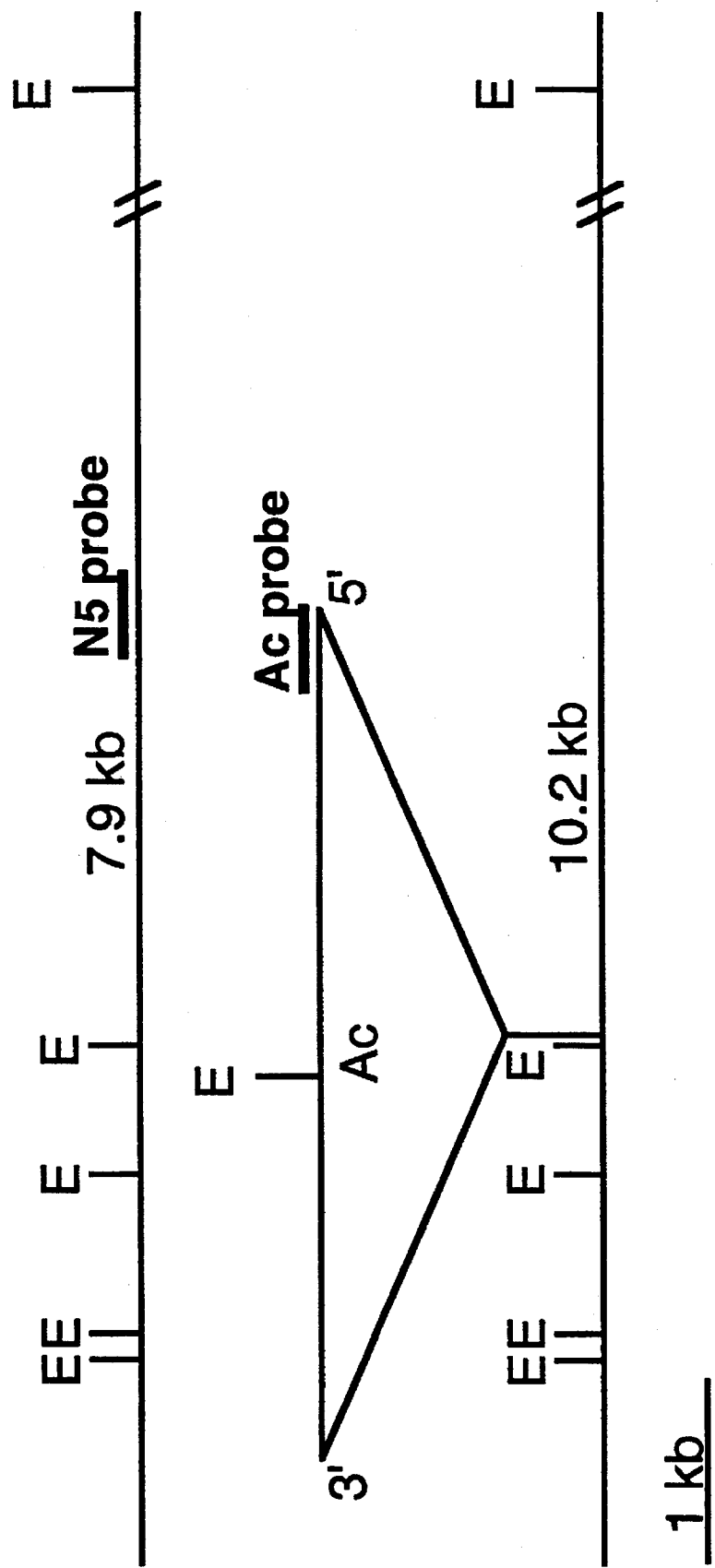

Given that Ac is 4.6 kb, a 7.9 kb EcoRI wild type or excision fragment is predicted when N-5 is used as a probe (see FIG. 3A). Examples of probe N-5 hybridization is shown in FIG. 3B. N-5 hybridizes to an 7.9 kb band in *N. glutinosa* and Samsun NN. The HR- mutant, C2-2, has hybridization to a 10.2 kb Ac10 insertion band and weak hybridization to the 7.9 kb band. D112-15 has both the 10.2 kb and 7.9 kb bands. E501-70 has the 10.2 kb insertion band and some hybridization to the 7.9 kb band. The two germinal revertants, F501-65 and F501-66, have only the 7.9 kb band. These plants were Nt-1 G/T, so they only carry one allele of N that has reverted. Other revertants, such as D112-15, which are Nt-1G/G have both the insertion and excision fragments. F501-2, 3, and 4 have both the 10.2 kb and 7.9 kb RFLPs. F501-48 and F501-64 have only the 7.9 kb excision fragment.

Significantly, the 54 TMV$^R$ E501 progeny of D112-15 had the 7.9 kb EcoRI excision band as did the 7 TMV$^R$ F501 plants. These results indicate that restoration of genomic DNA sequences to wild type is required for reversion to resistance. These results also demonstrate that one mutant allele of N had germinally reverted in D112-15 and that excision of Ac10 was responsible for the restoration of N gene function. These results were confirmed in the analysis of the progeny of E01-70, bearing only the Ac10, where all 7 TMV$^R$ plants had the 7.9 kb excision band. The Nt-1G/T plants showed no Ac10 hybridization, and they possessed the 7.9 kb wild type sized genomic fragment.

The TMV$^{R/S}$ plants, with the exception of two from the E501 generation, have both 10.2 kb and 7.9 kb bands. The presence of these bands together in the same tissue indicates that cells with Ac10 in place and Ac10 excision are present. Each band indicates that some tissue will be either TMV$^S$ or potentially revertant. This would explain the TMV$^{R/S}$ phenotype observed in these studies.

EXAMPLE 4

This example describes the analysis of the sequences of the genomic insertion and excision sites.

PCR products containing Ac excision sites were directly sequenced. Plants used are indicated in Table 6. Primers flanking the excision site NG 1-5 (bases 4477 to 4496 5'-GCCCTCGAGAAATCAAGAAAACAGAGGTC-3') and N7-52 (bases 4838 to 4856 5'-GCACTCGAGCTTCAAGATTACTACATTG-3') were used to amplify an ~379 bp product. PCR reactions were carried out as for IPCR except the following parameters were used: 94° C.-1min., 55° C.-2min., and 72° C.-3min. for 25 cycles. The PCR products were purified by electrophoresis in low melt agarose (FMC) followed by phenol extraction. Approximately 500 fmol of each product was used for sequencing with the fmol DNA Sequencing System (Promega, Madison, Wis.) using primer N7-52.

Nineteen of the 21 TMV$^S$ E501 plants as well as the four TMV$^S$ F501 plants of the Nt-1G/T genotype had the excision band and were missing Ac10 (Ac 10(-)). An Ac property that has been conserved in tobacco is that upon insertion, an eight base pair direct duplication flanking the element is created. This was confirmed in the sequences of Ac 10-1 and Ac 10-2. Ac 10 is flanked by an 8 bp direct repeat 5'-ATTTGCCG-3'. Frequently, Ac excision is imprecise and a "footprint" is left behind. Footprints can cause frameshift mutations and/or amino acid insertions or deletions that prevent the production of a functional gene product.

TABLE 6

| Wild type | | | |
|---|---|---|---|
| | | | Phenotype |
| | | —CAT TTG CCG TCT— | TMV$^R$ |
| | Ac insertion | | |
| | | —CAT TTG CCG//Ac//AT TTG CCG TCT— | TMV$^s$ |
| | Ac excision | | |

TABLE 6-continued

| N* footprints | | | |
|---|---|---|---|
| F501-48 | —CAT TTG CCC TTT GCC GTC | −9 aa- * | TMV$^S$ |
| F501-64 | —CAT TTG CCT GCC GTC | −9 aa- * | TMV$^S$ |
| E501-2 | —CAT TTG CTT TGC CGT | −4 aa- * | TMV$^S$ |
| E501-3 | —CAT TTG CCA TTT TGC CGT | −4 aa- * | TMV$^S$ |
| E501-9 | —CAT TTG CCC CGT | −4 aa- * | TMV$^S$ |
| E501-16 | —CAT TTG CCC TTT GCC GTC | −9 aa- * | TMV$^S$ |
| E501-28 | —CAT TTG CCC TTT GCC GTC | −9 aa- * | TMV$^S$ |
| N revertants | | | |
| D112-15 | —CAT TTG CCG TCT— | | TMV$^R$ |
| F501-34 | —CAT TTG CCG TCT— | | TMV$^R$ |
| F501-45 | —CAT TTG CCG TCT— | | TMV$^R$ |
| F501-65 | —CAT TTG CCG TCT— | | TMV$^R$ |
| F501-66 | —CAT TTG CCG TCT— | | TMV$^R$ |
| F501-67 | —CAT TTG CCG TCT— | | TMV$^R$ |
| F501-68 | —CAT TTG CCG TCT— | | TMV$^R$ |
| F501-69 | —CAT TTG CCG TCT— | | TMV$^R$ |

Table 6 shows sequence analysis of the Ac10 target site in the N gene and the resistance or sensitivity (to TMV infection) phenotype associated with a particular genotype. Upon insertion of Ac 10, an 8 bp sequence of wild type N sequence (from nucleotide 5034 to 5041; ATTTGCCG) is duplicated. Triplets of bases in Table 6 indicate codons within the cDNA sequence. Additional sequences that remained in sensitive plants following excision of Ac10 are underlined. The asterisk indicates the occurrence of a premature stop codon which occurs either nine or four amino acids downstream. E501s are backcross progeny of germinal revertant plant D112-15, and F501s are selfed progeny of plant E501-70. TMV sensitive and resistant phenotypes in Table 6 are indicated by TMV$^S$ and TMV$^R$, respectively.

Ac10 tags the N gene. The excision sites of seven Ac10(−) TMV$^S$ plants were sequenced, and each was found to have nucleotide changes when compared to the wild type excision site (Table 6). These nucleotide changes demonstrate that imperfect excision of Ac10 results in footprints that cause frameshift mutations. The predicted polypeptides are terminated 9 amino acids or 4 amino acids downstream of the footprint (Table 6).

Additionally, the excision sites of D112-15 and six TMV$^R$ plants from the F501 generation were sequenced and found to have the wild type sequence (Table 6). The ability to find revertant plants without base changes suggests that this region is very important to protein function, and that amino acid substitutions, additions, or deletions are not tolerated. However, a TMV$^S$ plant with a footprint that would allow synthesis of a full length but nonfunctional protein has not yet been identified. These results described herein demonstrate that Ac10 has tagged the N gene and suggest that precise excision of Ac10 from the N gene is required to restore the HR+ phenotype.

EXAMPLE 5

N cDNAs were isolated from a *N. glutinosa* cDNA library as follows: Plants eight to twelve weeks old were infected with TMV at 32° C. The temperature was shifted to 24° C. at 24 hours post inoculation. Leaves were harvested for polyadenylated (Poly (A)$^+$)RNA isolation at 48 hours post inoculation. cDNA was prepared from 5 μg of Poly (A)$^+$ RNA using the λ-Zap cDNA synthesis kit (Stratagene, La Jolla, Calif.). cDNA was packaged with Gigapack II Gold packaging extracts from Stratagene and plated on the host strain *Escherichia coli* XL 1-Blue mrf.

Ac10-1 was used to screen 1.0×10$^6$ clones of a cDNA library constructed from RNA of TMV-infected *N. gluti-nosa*. Fifteen clones were identified as having homology to Ac10-1; however, only one (C7) had 100% sequence identity to Ac10-1. A probe (N-5) was derived from bases 5020 to 5370 at the 3' terminus of C7 that was single copy in tobacco and that hybridized to a 7.9 kb EcoRI fragment. Subsequently, 1×10$^6$ plaques were hybridized with the N-5 probe. Three clones (C16, C17, and C18) were isolated in the second screen, and all had 100% sequence identity to Ac10-1. The full length sequences of cDNA C7, C16, and C18 inserts were determined (see below).

Double stranded plasmid DNA was sequenced by the dideoxy chain termination method (Sanger et al., *Proc. Natl. Acad. Sci. USA* 74:5463–5467 (1977)) using the Sequenase version 2.0 system (United States Biochemical Corporation, Cleveland, Ohio), and for sequencing of the C7 cDNA, nested deletions were prepared by the Exonuclease III method (Henikoff, *Methods in Enzymology* 155:156–165 (1987)). cDNAs C16 and C18 were sequenced using primers derived from C7 sequence.

Figure 4A:
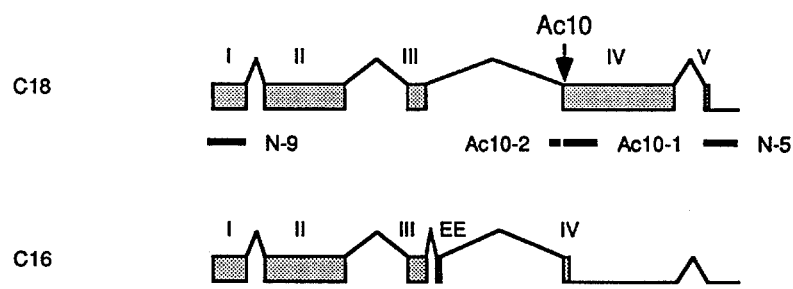
FIG. 4A and FIG. 4B summarize organization of the N gene.
Figure 4B:
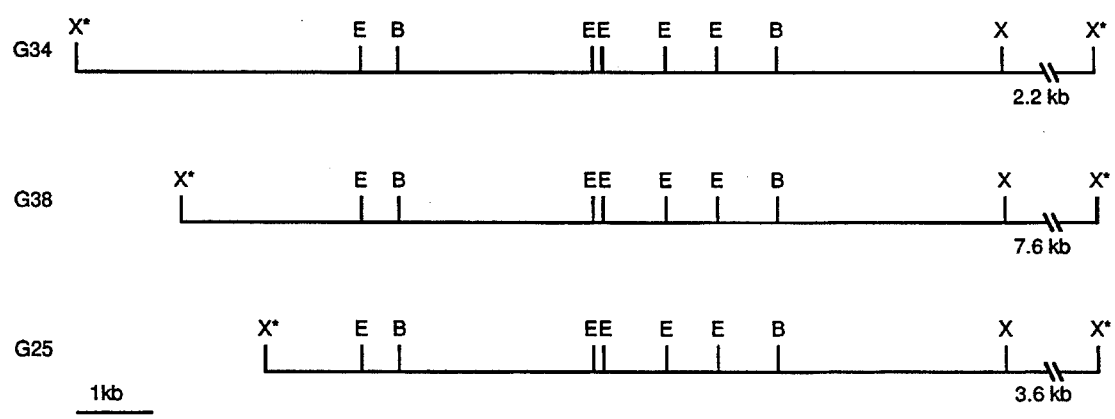

Sequence analyses were performed using the GCG sequence analysis programs (Madison, Wis.). Maps were deduced for the exons and introns encoded by the genomic N gene (see SEQ ID NO: 1) from sequence analysis of the C7, C16, and C18 cDNA clones and partial sequencing of the G38 λ clone (FIG. 4B). Taken together, C7 and C18 predict that five exons are spliced to form an open reading frame of 3432 base pairs that encodes a polypeptide of 1144 amino acids (N). The C18 cDNA sequence is presented in SEQ ID NO:3. C16 encodes a polypeptide of 652 amino acids (Ntr), because a 70 base pair exon is spliced alternatively to make a truncated open reading frame of 1956 bp (FIG. 4A and SEQ ID NO:5). This extra exon (EE) may be spliced in a manner similar to that of the fibronectin EDA exon (M. Caputi, *Nucleic Acids Research.* 22:1018–1022 (1994)). Sequence motifs within the 70 bp exon are 95% similar to sequences in the EDA exon that define a bipartite enhancer that modulates splicing of this 81 bp exon.

The 3' termini of the cDNAs vary in length, indicating that different polyadenylation signals are used. Multiple potential polyadenylation signals are found at positions in the 3' untranslated region of these cDNA clones that could account for the different processing events. C7 has the longest 3' terminus and contains the sequence for the truncated C16 and C18 3' termini. C7 and C16 are identical at the 5' terminus. C18 sequence is found entirely within C16 and C7, so it is not a full length cDNA and has the shortest 3' terminus. C7 contains intron 2 and may be from a mRNA that was not fully spliced. C16 and C18 lack intron 2. Addition of the 5' 750 bp of sequence of C16 or C7 to C18 forms a predicted open reading frame of 3432 bp encoding a polypeptide of 1144 amino acids (Table 7A). Partial sequencing of the G38 λ clone shows that all sequences necessary to give rise to the three types of cDNAs isolated are present in the genomic sequence. Thus these cDNAs are encoded by a single gene.

The predicted molecular weight of the predicted N and Ntr proteins are 131.4 kd and 75.3 kd, respectively. Table 7A shows the deduced amino acid sequence for the N gene product (see also SEQ ID NO: 4). The potential signaling (cytoplasmic) domain is underlined. Amino acids conserved among ATP/GTP-binding site motif (P-loop) are double underlined. Leucine rich repeats (LRR1 to LRR13) are in italics. Eight potential N-linked glycosylation sites occur within the amino acid sequence of N. These sites are indicated by the letters in bold type in Table 7A and have the consensus amino acid sequence NX(S/T). Abbreviations used in Tables 7A-C for the one letter amino acid code are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

Analysis of the N protein sequence with the program ualom indicates that no transmembrane region is present in N. Furthermore, analysis of the N protein sequence with the program "Signalase" indicates no signal sequence is present. Thus, based on sequence analysis, N appears to be localized to the cytoplasm.

The deduced amino acid sequence of the N polypeptide was compared with Genbank (release 82.0) using the BLAST program (Altschul et al., *J. Mol. Biology* 215:403–410 (1990)). The predicted amino acid sequence shows limited but significant similarities to proteins known to be involved in signal transduction.

The predicted amino acid sequence of N contains a P-loop motif (Table 7A). The sequence GMGGVGKT (aa 216 to 223) fits the P-loop consensus sequence (A/G)XXXXGK(S/T) found in various ATP- or GTP-binding proteins (Table 7A). The families of proteins containing the P-loop includes adenylate kinases, ras family of proteins, elongation factors, ATP synthase b-subunit, thymidine kinases and phosphoglycerate kinases (M. Saraste et al., *Trends in Biochemical Sciences* 15:430–434 (1990)). This particular P-loop is most likely to be involved in the binding of ATP. The consensus sequences, DXXG and NXKD, for GTP binding in addition to the P-loop are not present in the aa sequence (Dever et al., *Proceedings of the National Academy of Sciences USA* 84:1814–1818 (1987)).

In addition to the P-loop, Fry et al. (*Proceedings of the National Academy of Sciences USA* 83:907–911 (1986)) defined two other "segments" that appear to be involved in ATP binding in adenylate kinase and F1-ATPase. Inspection of the N sequence suggests that these segments are present and at the proper spacing. Segment 2 contains the dipeptide (I,A,L,V)(V,I) and N has the sequence AI at positions 228 and 229, respectively (Table 7A). At 80–100 amino acids from the P-loop, segment 3 was defined as a glycine followed by a stretch of 5 hydrophobic amino acids and an aspartic acid (Table 7A). N has the sequence VLIVLDD at amino acids 296–302. From the amino acid sequence, it is not possible to predict under what conditions ATP is bound or upon binding whether ATP hydrolysis occurs spontaneously or requires other factors.

Table 7B shows alignment of amino terminal amino acids (the potential signaling domain) (8 to 150 of SEQ ID NO:4) with the cytoplasmic (signaling) domain of the *Drosophila* Toll protein, (aa 804–9996; Yamagata et al., *Gene* 139:223–228 (1994)) and human Interleukin 1-receptor protein (H IL1-R, aa 317–524; Signs et al., *Proceedings of the National Academy of Science* 86:8946–8950 (1989)). Boxes indicate the regions of similarity. Conservative substitutions used are: hydrophobic amino acid=L/I/V/M/A/F; ionic amino acid=K/R/D/E/Q/N/H; aromatic amino acid=F/Y.

The N sequence contains some of the conserved amino acids required for transmission of signal :from cytoplasm to nucleus in Toll and IL1-R regulatory pathways (Schneider et al., *Genes and Development* 5:797–807 (1991); Heguy et al., *Journal of Biological Chemistry*, 267:2605–2609 (1992)).

The deduced amino acid sequence of N from amino acids 590 to 928 of SEQ ID NO:4 contains a leucine-rich region composed of thirteen repeats of approximately 25 amino acids in length. Table 7C shows primary structure of N gene leucine rich repeats (LRR) (aa 590–928) and comparison of its consensus sequence with LRR consensus of yeast adenylate cyclase (AdCy, Kataoka et al., *Cell* 43:493–505 (1985)), Drosophila Toll (Hashimoto et al., *Cell* 52:269–279 (1988)), human platelet membrane glycoprotein Iba chain (H Gplba, Titani et al., *Proceedings of the National Academy of Science* 84:5610–5614 (1987)), Drosophila Chaoptin (Reinke et al., *Cell* 52:291–301 (1988)) and *Arabidopsis* receptor-like transmembrane kinase (TMK1, Chang et al., 1Plant Cell 4:1263–1271 (1992)); TMKL1, Valon et al., (*Plant Molecular Biology* 23:415–421 (1993)); and RLK5, Walker, *The Plant Journal* 3:451–456 (1993)).

Leucine-rich repeats (LRRs) are found in a wide variety of proteins involved in signal transduction, cell adhesion, and various other functions, and they are thought to mediate protein-protein interactions. The consensus sequence derived from the aligned LRRs is similar to the consensus found in yeast adenylate cyclases (Kataoka (1985) supra), Drosophila Toll (Hashimoto et al.,(1988) supra), human platelet membrane glycoprotein Iba chain (Titani et al., (1987) supra), Drosophila Chaoptin (Reinke et al., (1988) supra) and Arabidopsis receptor like transmembrane kinases (Chang et al., (1992) supra; Valon et al., (1993) supra; and J. Walker, (1993) supra) (Table 7C). With the exception of the yeast adenylate cyclase, the LRR domain is believed to be in the extracellular matrix in these proteins.

TABLE 7A

| 1 MASSSSSSRW | SYDVFLSFRG | EDTRKTFTSH | LYEVLNDKGI | KTFQDDKRLE | YGATIPGELC |
|---|---|---|---|---|---|
| 61 KAIEESQFAI | VVFSENYATS | RWCLNELVKI | MECKTRFKQT | VIPIFYDVDP | SHVRNQKESF |

TABLE 7A-continued

| | | | | | |
|---|---|---|---|---|---|
| 121 AKAFEEHETK | YKDDVEGIQR | WRIALNEAAN | LKGSCDNRDK | TDADCIRQIV | DQISSKLCKI |
| 181 SLSYLQNIVG | IDTHLEKIES | LLEIGINGVR | IMGIWGMGGV | GKTTIARAIF | DTLLGRMDSS |
| 241 YQFDGACFLK | DIKENKRGMH | SLQNALLSEL | LREKANYNNE | EDGKHQMASR | LRSKKVLIVL |
| 301 DDIDNKDHYL | EYLAGDLDWF | GNGSRIIITT | RDKHLIEKND | IIYEVTALPD | HESIQLFKQH |
| 361 AFGKEVPNEN | FEKLSLEVVN | YAKGLPLALK | VWGSLLHNLR | LTEWKSAIEH | MKNNSYSGII |
| 421 DKLKISYDGL | EPKQQEMFLD | IACFLRGEEK | DYILQILESC | HIGAEYGLRI | LIDKSLVFIS |
| 481 EYNQVQMHDL | IQDMGKYIVN | FQKDPGERSR | LWLAKEVEEV | MSNNTGTMAM | EAIWVSSYSS |
| 541 TLRFSNQAVK | NMKRLRVFNM | GRSSTHYAID | YLPNNLRCFV | CTNYPWESFP | STFELKMLVH |
| 601 LQLRHNSLRH | LWTETKHLPS | LRRIDLSWSK | RLTRTPDFTG | MPNLEYVNLY | QCSNLEEVHH |
| 661 SLGCCSKVIG | LYLNDCKSLK | RFPCVNVESL | EYLGLRSCDS | LEKLPEIYGR | MKPEIQIHMQ |
| 721 GSGIRELPSS | IFQYKTHVTK | LLLWNMKNLV | ALPSSICRLK | SLVSLSVSGC | SKLESLPEEI |
| 781 GDLDNLRVFD | ASDTLIRPP | SSIIRLNKLI | ILMFRGFKD | VHFEFPPVAE | GLHSLEYLNL |
| 841 SYCNLIDGGL | PEEIGSLSSL | KKLDLSRNNF | EHLPSSIAQL | GALQSLDLKD | CQRLTQLPEL |
| 901 PPELNELHVD | CHMALKFIHY | LVTKRKKIHR | VKLDDAHNDT | MYNLFAYTMF | QNISSMRHDI |
| 961 SASDSLSLTV | FTGQPYPEKI | PSWFHHQGWD | SSVSVNLPEN | WYIPDKFLGF | AVCYSRSLID |
| 1021 TTAHLIPVCD | DKMSRMTQKL | ALSECDTESS | NYSEWDIHFF | FVPFAGLWDT | SKANGKTPND |
| 1081 YGIIRLSFSG | EEKMYGLRLL | YKEGPEVNAL | LQMRENSNEP | TEHSTGIRRT | QYNNRTSFYE |
| 1141 LING | | | | | |

TABLE 7B

```
    N   S R W - S Y D V F L S F R G E D T R K T F T S H L Y E V - - L N D K G I K T F Q -
  TOLL  D K D K K F D A F I S Y S H K D Q S - - F I E Q Y L - V P Q L E H - G P Q K F Q L
 HILDR  S D G K T Y D A Y I L Y P - K E G S - - - T C D I F - V F K L E - K Q C G - Y K L

N   - D D K R L E Y - G A T I P G E L C K A I E E S Q F A I V V F S E N Y A T S R W C
  TOLL  C V H E R D W L V G G F I P E N I V R S V A D S R R T I I V L S Q N F I E S E W A
 HIL-1R F I Y G R D D Y V G E D I V E V I N E N V K K S R R L I I I L V R E T S G F S W L

N   L N E L V K I M E C K T R F K Q T V I P F Y D V - D P S H V R N Q K E S F A K A
  TOLL  R M E F - R A A H R S A L N E G R A R I I V V I Y S D I G D V E K L D E E L - K A
 HIL-1R S S E E - O I A M Y N A L V Q D G I K V V L L E I E K I Q D Y E K M P E S I - K -

N   F E E H E T K Y K - D D V E G I Q R W R I A L N E A A N
  TOLL  Y L K M N T Y L K W G D - P W F W D - K L R F G V P H R
 HIR-1R F I K K H G A I R W G D K T R F W K - N V R Y H M P V Q
```

TABLE 7C

```
590
P S T F E   L K M L V   H L Q L R   H   N S L R H   L W T E T K H L
P S        L R R I D   L S W S K R L T     R T P D F T G M

P N   L E Y V N   L Y Q C S N L E   E V H H S L G C C S K V I G L Y L N D C K S L K R F
P C V N V E S     L E Y L G L R S C D S L E K L
```

TABLE 7C-continued

```
         P E   I Y G R M K P EIQIH    M Q G S G   I R E L
         P S S I F Q Y K T H VTKLL    L WN MK N L V A L

P S S I C R L K S L V S L S V S G C S K L E S L
         P E E I G D L D N L R V F D A S D T L I L R P
         P S S I I R L N K L I I L M F R G F K D G V H F E F P
         P V A E G   L H S L E Y L N L S Y C N   L I D G G L
         P E E I G S L S S L K K L D L S R N N F E H   L
         P S S I A Q L G A L Q S L D L K D C Q R L T Q L P E L
         P P E L N E L H V D C H M A L K F I  H Y L V T K R K K L
                                                                928
```

| | |
|---|---|
| N Gene | P ——α——L——L——L—L————L——L |
| AdCy | P ——α——L——L——L—L——N—L——L |
| Toll | P ——L F—H——N L——L—L——N—L——L |
| Toll | P ——L F—H——N L——L—L——N—L——L |
| H Gp1ba | P—G L L——L P—L S—L——L S—N—L T T L |
| H trk | L——L—α——N—L——α |
| Chaoptin | P———F——L——L——L D L S—N—L——I |
| RLK5 | P——L——L——L——L—L——N—L S G—I |
| TMK1 | L——L——L——L—L——N—α—G—α P |
| TMKL1 | ——I————L—S L—L——N—L S G—L P |

EXAMPLE 6

This example describes the isolation of genomic N gene sequences.

To cream a genomic library, DNA prepared from *N. glutinosa* was partial digested with MboI and size fractionated by gel electrophoresis. DNA fragments>12 kb were ligated to BamHI digested, dephosphorylated arms of bacteriophage λ Gem-11 (Promega). Ligations were packaged with Gigapack II Gold packaging extracts (Stratagene, La Jolla, Calif.) and 1×10⁶ plaque forming units were plated on the SURE *E. coli* strain purchased from GIBCO, BRL., Gaithersburg, Md.) host strain.

To isolate genomic N gene sequences, a bacteriophage λ library of the MboI partialled *N. glutinosa* DNA was screened with probes, N-5 and N-9 (nucleotides 695 to 1090 of C7). Three clones were purified that hybridized to both N-5 and N-9. These clones (G25, G34, and G38) were restriction mapped with EcoRI, BamHI, and XhoI, and characterized by Southern analysis (FIG. 4B). It was determined that the three clones overlapped and contained the entire genomic N gene. G34 has 1.4 kb more DNA upstream of the N gene than G38, whereas G38 is 5.4 kb longer 3' of the gene. The G25 clone sequences were contained with the G38 clone.

EXAMPLE 7

This example describes susceptible or mutant plants transformed with genomic N gene clones, which plants were resistant to TMV.

SR1 tobacco and TMV sensitive plants F501–48 and F501–64 bearing germinal Ac excision events were transformed with either pTG34 or pTG38. pTG34 and pTG38 were constructed by subcloning a 12.0 kb or 10.6 kb XhoI fragment, respectively, from the overlapping DNA clones G34 or G38 into the T-DNA vector, pOCA28 (Olscewski et al., *Nucleic Acids Research* 16:10765-10781 (1988)) that was linearized with SalI and treated with calf intestinal alkaline phosphatase. The transformations were performed as described for the pGV3850 HPT::pKU3 construct (see Example 1).

Clones G34 and G38 were chosen for genomic complementation to determine whether this gene was sufficient to confer TMV resistance to TMV susceptible tobacco. These two clones were more likely than G25 to contain all cis sequences necessary for proper expression of the transgene because of their more extensive 5' ends. The 10.6 kb G38 and 12.0 kb G34 XhoI fragments were subcloned into the T-DNA vector pOCA28 and transformed into tobacco via Agrobacterium mediated transformation.

Clones pTG34 and pTG38 both conferred TMV resistance to TMV susceptible SR1 tobacco and the mutants F501–48 and F501–64. FIG. 1D shows that TMV susceptible SR1 plants transformed with cloned *N. glutinosa* N gene DNA (clone pTG-38) were made resistant to TMV.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 7400 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Nicotiana glutinosa
        ( F ) TISSUE TYPE: leaf ( i x ) FEATURE:
        ( A ) NAME/KEY: exon
        ( B ) LOCATION: join(294..772, 1003..2098, 2941..3213,
            5032..6600, 6934..6951)

( i x ) FEATURE:
        ( A ) NAME/KEY: intron
        ( B ) LOCATION: 773..1002

( i x ) FEATURE:
        ( A ) NAME/KEY: intron
        ( B ) LOCATION: 2099..2940

( i x ) FEATURE:
        ( A ) NAME/KEY: intron
        ( B ) LOCATION: 3214..5031

( i x ) FEATURE:
        ( A ) NAME/KEY: intron
        ( B ) LOCATION: 6601..6933

( i x ) FEATURE:
        ( A ) NAME/KEY: CDS
        ( B ) LOCATION: join(294..772, 1003..2098, 2941..3213,
            5032..6600, 6934..6951)

( x i ) SEQUENCE DESCRIPTION: SEQ ID NO:1:

```
TCAATCAATG GAAGGAATTC CTACTCCCTT CTATTAAAGT CAAAGAAAAC CCAATAATTC        60

CTTTTATTGC ATTAAGAAGA ATTTTCCTAC TAGTGTATAT CAGTTGACTA GGACACCAAT       120

AATTCTATGG AGTAGAGCCC ATCTCACACA AACTTTTCC AATAGCAATA TAACTCTTAT        180

CTCTTCTAAT ATATATAAAA ATTTGTTGAA AATACATCTA TTATTCTCTT ACCACAATCA       240

CAATTTTTTC ACATACAGTT TCTTACTCTT TTCAGAGAAT TAACGTTGAG TCC ATG          296
                                                              Met
                                                               1

GCA TCT TCT TCT TCT TCT TCT AGA TGG AGC TAT GAT GTT TTC TTA AGT         344
Ala Ser Ser Ser Ser Ser Ser Arg Trp Ser Tyr Asp Val Phe Leu Ser
          5                   10                  15

TTT AGA GGC GAA GAT ACT CGA AAA ACG TTT ACA AGT CAC TTA TAC GAA         392
Phe Arg Gly Glu Asp Thr Arg Lys Thr Phe Thr Ser His Leu Tyr Glu
            20                  25                  30

GTC TTG AAT GAT AAG GGA ATA AAA ACC TTT CAA GAT GAT AAA AGG CTA         440
Val Leu Asn Asp Lys Gly Ile Lys Thr Phe Gln Asp Asp Lys Arg Leu
        35                  40                  45

GAG TAC GGC GCA ACC ATC CCA GGT GAA CTC TGT AAA GCT ATA GAA GAG         488
Glu Tyr Gly Ala Thr Ile Pro Gly Glu Leu Cys Lys Ala Ile Glu Glu
50                  55                  60                  65

TCT CAA TTT GCC ATT GTT GTT TTC TCA GAG AAT TAT GCA ACA TCA AGG         536
Ser Gln Phe Ala Ile Val Val Phe Ser Glu Asn Tyr Ala Thr Ser Arg
```

|  |  |  |  |  |  |  |  |  |  |  |  |  |  |  |  |
|---|---|---|---|---|---|---|---|---|---|---|---|---|---|---|---|
|  |  |  |  |  | 70 |  |  |  |  | 75 |  |  |  |  | 80 |

```
TGG TGT TTG AAT GAA CTA GTG AAG ATC ATG GAA TGC AAA ACT CGA TTT     584
Trp Cys Leu Asn Glu Leu Val Lys Ile Met Glu Cys Lys Thr Arg Phe
            85                  90              95

AAG CAA ACT GTT ATA CCG ATA TTC TAT GAT GTG GAT CCA TCA CAT GTT     632
Lys Gln Thr Val Ile Pro Ile Phe Tyr Asp Val Asp Pro Ser His Val
        100             105             110

CGG AAC CAA AAG GAG AGC TTT GCA AAA GCC TTT GAA GAA CAT GAA ACA     680
Arg Asn Gln Lys Glu Ser Phe Ala Lys Ala Phe Glu Glu His Glu Thr
115             120             125

AAG TAT AAG GAT GAT GTT GAG GGA ATA CAA AGA TGG AGG ATT GCT TTA     728
Lys Tyr Lys Asp Asp Val Glu Gly Ile Gln Arg Trp Arg Ile Ala Leu
130             135             140                         145

AAT GAA GCG GCC AAT CTC AAA GGC TCA TGT GAT AAT CGT GAC AA          772
Asn Glu Ala Ala Asn Leu Lys Gly Ser Cys Asp Asn Arg Asp Lys
            150             155             160

GTGAGTTAAA AACATATAAG CTGAATACTT TGCATTCAAA TGAGTTAAAC ATAATCTTAA   832

ATAAATTTTT CAATTTTTG GAATAAATTG ATAGTTGATT ATATATGTTT CTATCAGTTA    892

ATTACAAACT CAATAACATT ATTACGTAGA TAAAATTTTT ATTAGTTCTT CAAAGAGTTT   952

GATTTATGTG CACACTCTTT GTATATATCA CAATCTTTTT ACTTTGTAG G ACT GAT     1009
                                                       Thr Asp

GCA GAC TGT ATT CGA CAG ATT GTT GAC CAA ATC TCA TCC AAA TTA TGC     1057
Ala Asp Cys Ile Arg Gln Ile Val Asp Gln Ile Ser Ser Lys Leu Cys
        165             170             175

AAG ATT TCT TTA TCT TAT TTG CAA AAC ATT GTT GGA ATA GAT ACT CAT     1105
Lys Ile Ser Leu Ser Tyr Leu Gln Asn Ile Val Gly Ile Asp Thr His
        180             185             190

TTA GAG AAA ATA GAA TCC TTA CTA GAG ATA GGA ATC AAT GGT GTT CGG     1153
Leu Glu Lys Ile Glu Ser Leu Leu Glu Ile Gly Ile Asn Gly Val Arg
195             200             205                         210

ATT ATG GGG ATC TGG GGA ATG GGG GGA GTC GGT AAA ACA ACA ATA GCA     1201
Ile Met Gly Ile Trp Gly Met Gly Gly Val Gly Lys Thr Thr Ile Ala
            215             220             225

AGA GCT ATA TTT GAT ACT CTT TTA GGA AGA ATG GAT AGT TCC TAT CAA     1249
Arg Ala Ile Phe Asp Thr Leu Leu Gly Arg Met Asp Ser Ser Tyr Gln
        230             235             240

TTT GAT GGT GCT TGT TTC CTT AAG GAT ATT AAA GAA AAC AAA CGT GGA     1297
Phe Asp Gly Ala Cys Phe Leu Lys Asp Ile Lys Glu Asn Lys Arg Gly
        245             250             255

ATG CAT TCT TTG CAA AAT GCC CTT CTC TCT GAA CTT TTA AGG GAA AAA     1345
Met His Ser Leu Gln Asn Ala Leu Leu Ser Glu Leu Leu Arg Glu Lys
260             265             270

GCT AAT TAC AAT AAT GAG GAG GAT GGA AAG CAC CAA ATG GCT AGT AGA     1393
Ala Asn Tyr Asn Asn Glu Glu Asp Gly Lys His Gln Met Ala Ser Arg
275             280             285                         290

CTT CGT TCG AAG AAG GTC CTA ATT GTG CTT GAT GAT ATA GAT AAT AAA     1441
Leu Arg Ser Lys Lys Val Leu Ile Val Leu Asp Asp Ile Asp Asn Lys
            295             300             305

GAT CAT TAT TTG GAG TAT TTA GCA GGT GAT CTT GAT TGG TTT GGT AAT     1489
Asp His Tyr Leu Glu Tyr Leu Ala Gly Asp Leu Asp Trp Phe Gly Asn
            310             315             320

GGT AGT AGA ATT ATT ATA ACA ACT AGA GAC AAG CAT TTG ATA GAG AAG     1537
Gly Ser Arg Ile Ile Ile Thr Thr Arg Asp Lys His Leu Ile Glu Lys
        325             330             335

AAT GAT ATA ATA TAT GAG GTG ACT GCA CTA CCC GAT CAT GAA TCC ATT     1585
Asn Asp Ile Ile Tyr Glu Val Thr Ala Leu Pro Asp His Glu Ser Ile
340             345             350

CAA TTG TTC AAA CAA CAT GCT TTC GGA AAA GAA GTT CCA AAT GAG AAT     1633
```

```
Gln Leu Phe Lys Gln His Ala Phe Gly Lys Glu Val Pro Asn Glu Asn
355                 360                 365                 370

TTT GAG AAG CTT TCA TTA GAG GTA GTA AAT TAT GCT AAA GGC CTT CCT       1681
Phe Glu Lys Leu Ser Leu Glu Val Val Asn Tyr Ala Lys Gly Leu Pro
                375                 380                 385

TTA GCC CTC AAA GTG TGG GGT TCT TTG CTG CAT AAC CTA CGA TTA ACT       1729
Leu Ala Leu Lys Val Trp Gly Ser Leu Leu His Asn Leu Arg Leu Thr
            390                 395                 400

GAA TGG AAA AGT GCT ATA GAG CAC ATG AAA AAT AAC TCT TAT TCT GGA       1777
Glu Trp Lys Ser Ala Ile Glu His Met Lys Asn Asn Ser Tyr Ser Gly
        405                 410                 415

ATT ATT GAT AAG CTC AAA ATA AGT TAT GAT GGA TTA GAG CCC AAA CAA       1825
Ile Ile Asp Lys Leu Lys Ile Ser Tyr Asp Gly Leu Glu Pro Lys Gln
    420                 425                 430

CAA GAG ATG TTT TTA GAT ATA GCA TGC TTC TTG CGA GGG GAA GAA AAA       1873
Gln Glu Met Phe Leu Asp Ile Ala Cys Phe Leu Arg Gly Glu Glu Lys
435                 440                 445                 450

GAT TAC ATC CTA CAA ATC CTT GAG AGT TGT CAT ATT GGA GCT GAA TAC       1921
Asp Tyr Ile Leu Gln Ile Leu Glu Ser Cys His Ile Gly Ala Glu Tyr
                455                 460                 465

GGG TTA CGT ATT TTA ATT GAC AAA TCT CTT GTG TTC ATC TCT GAA TAT       1969
Gly Leu Arg Ile Leu Ile Asp Lys Ser Leu Val Phe Ile Ser Glu Tyr
            470                 475                 480

AAT CAG GTT CAA ATG CAT GAC TTA ATA CAG GAT ATG GGT AAA TAT ATA       2017
Asn Gln Val Gln Met His Asp Leu Ile Gln Asp Met Gly Lys Tyr Ile
        485                 490                 495

GTG AAT TTT CAA AAA GAT CCC GGA GAA CGT AGC AGA TTA TGG CTC GCC       2065
Val Asn Phe Gln Lys Asp Pro Gly Glu Arg Ser Arg Leu Trp Leu Ala
    500                 505                 510

AAG GAA GTC GAA GAA GTG ATG AGC AAC AAC ACA GTAAGTAAGC TAAATAATGC     2118
Lys Glu Val Glu Glu Val Met Ser Asn Asn Thr
515                 520                 525

AATAATATTT AATTTCTAAT TTTATATTCT AAAGACACAT AGGGCAGTCA ATTCCAGTTA     2178

TTTGTTCCTC TTGCTTCATA GTCTTGACGG TACATCATTT TAGTTGTTTA CTTTAGTTAG     2238

TAGGAGATAT AAAAGTAATA TTAATTACCT CATTAGTAAA AAAAAACATT AATTGCCTAA     2298

TTTGTTTAGT AGCCGCTTTA ATTTACGTTC CCTAATTCGT TTTTTCTTAT ATTTTTTAGG     2358

GATGGATTAG TCTAGTAGCC ACTTAATCTG TTTGATCCAA TGTCTTTCTT TGGATTAACT     2418

TGAAAATTTT ATGACATTAT ATATAATAAC TCAATCATTC ATTCACTTTA CCATTATTAT     2478

TTTTTATATA AAGTTACAAT TTATTGGTAC TGTTTCAGTT ACAATTACTT TCCAACATGG     2538

AAAACTTATA AACTGGACTC CAATAAACTT ATAAGAAAAA TGTAATAATA GAAAATAAAA     2598

TTATATAATT AATTACAAAA AAGTATTTTT CTGAAGTAAC ATCAGTATTT CTTAAAAAGA    2658

ATCCAATTAA CATTGTATCT TAAACTTTGG TATTGTAAGG CGTGAGAAAG TAGTGGCCTT    2718

ATTTCAATTT GACGTGAAGA ATAGAATGCC TTTTAACGAC ATAAGGGAAG GGGGCAAGAA    2778

TAAGTTTCTA TTCAGCCGGG CTCGAAGCAG AAGGTAGAAC GTAATATCTT TTGTTGGTTC    2838

AGCTCATCAA GCTATTACAA AAGAGTCCGC TCATATTAAC AAACGGAGTT TATACGACAT    2898

TTGAAATTAT ACTTTGTAGA CTAATGATCT TCTTGTTACC AG GGG ACC ATG GCA       2952
                                                 Gly Thr Met Ala

ATG GAA GCA ATT TGG GTT TCT TCT TAT TCT AGT ACT CTA CGC TTT AGC      3000
Met Glu Ala Ile Trp Val Ser Ser Tyr Ser Ser Thr Leu Arg Phe Ser
530                 535                 540                 545

AAT CAG GCC GTG AAA AAT ATG AAA AGG CTT AGG GTA TTT AAC ATG GGG      3048
Asn Gln Ala Val Lys Asn Met Lys Arg Leu Arg Val Phe Asn Met Gly
            550                 555                 560
```

| | | | | | | | | | | | | | | | | |
|---|---|---|---|---|---|---|---|---|---|---|---|---|---|---|---|---|
| AGG | TCG | TCG | ACA | CAT | TAT | GCC | ATC | GAT | TAT | CTG | CCC | AAC | AAC | TTG | CGT | 3096 |
| Arg | Ser | Ser | Thr 565 | His | Tyr | Ala | Ile | Asp 570 | Tyr | Leu | Pro | Asn | Asn 575 | Leu | Arg | |
| TGT | TTT | GTT | TGC | ACT | AAC | TAT | CCT | TGG | GAG | TCA | TTT | CCA | TCT | ACA | TTT | 3144 |
| Cys | Phe | Val 580 | Cys | Thr | Asn | Tyr | Pro | Trp 585 | Glu | Ser | Phe | Pro | Ser 590 | Thr | Phe | |
| GAA | CTC | AAA | ATG | CTT | GTT | CAC | CTC | CAA | CTC | CGA | CAC | AAT | TCT | CTG | CGT | 3192 |
| Glu | Leu | Lys 595 | Met | Leu | Val | His 600 | Leu | Gln | Leu | Arg | His 605 | Asn | Ser | Leu | Arg | |
| CAT | TTA | TGG | ACA | GAA | ACA | AAG | GTACAATAGC | | TTGAATTCTA | | TTTTGTTGTC | | | | | 3243 |
| His 610 | Leu | Trp | Thr | Glu | Thr 615 | Lys | | | | | | | | | | |

| | | | | |
|---|---|---|---|---|
| ATTTATTTTT | CTCTCTAACT | ATCTTTGTCC | TTAATTTGG | TGATAATGAA CAAATATTAT | 3303 |
| TGTTTTTTGT | TATGAAACAA | TAAAGAAGA | AGAACAATAT | TGCAGAGAAA GAGGGAGATG | 3363 |
| GAATTCTTAT | TGAATTTTGG | GGCGATTTAC | AATGGGGTAA | GACCCCTCTA TTTACAGGGG | 3423 |
| AAAAATAACT | TAGCCTCAAA | ATAAAGCTCT | TTAAAAGATA | GACATTCACT CTAAATAGAA | 3483 |
| TTCTATTATA | ACACTTTTGG | CGTACTTCCT | TTTTTGGCTA | GAATTATGAT ACATGTCTTT | 3543 |
| AAATGAACAG | AAGTTGCTTT | TGTAATTTAT | CAGGACTTAT | GTTGAAACTT ATGAAAATTG | 3603 |
| TTATTGTTTA | TGTTGTCTAA | TACTAAATAT | AAAATACAAT | AATATTTTAT CGTAATTTTT | 3663 |
| TAAAAATTTG | TCAAATAATG | CAAATGAAAA | ATTAAATTTT | TTGGTCCTTT AAAAATTTGA | 3723 |
| GAATGAAAAA | GTACGAGTTA | TACTTCCTAA | AAGTTTGATA | GTGAATAATA TGTAAAATTT | 3783 |
| AAAGAATGAC | TAATATTGGA | CTAATACTTT | AAAACAAATA | ACTTAATATA CAAATTATAG | 3843 |
| CGAGACATTT | TCATTCGTTG | TACTGAATGC | AAGAAAGAAA | GGAAAAAAAA ACTCATTTAT | 3903 |
| AATATAGTTT | GTCTTCTACT | ATTTTACCTT | ATTGCTTCAA | ATTTGTATTT TATCGATTTT | 3963 |
| GCTATATCTT | ATGATTTTTT | TCACGGTCAA | TATTCTTCTT | ACAAGAATAA ATTTTATATA | 4023 |
| CCTCAAGTGT | TTTGTCAATT | TGATAAATAA | TTTTTCTTAT | ATGATGAACT TGTAAAATAA | 4083 |
| TAGAATTGGA | TTCTTTTGCT | AATTAGTTAA | TTCAACGACT | TAATTATTTA TTCTCAACAT | 4143 |
| TAAAGGAAAT | AATTTAGTTT | TTATTAATTC | AAACTCTTAG | TATTTGCTCA TTCTAATTTT | 4203 |
| CAGTCCAATA | AGAATTCAAT | TTTCAAATAG | TAAGAAAAGT | CATATATTTT GAATTTTATG | 4263 |
| TTTTCCGAAG | CATTGTTTGT | TTGTTTAACT | CTACGGGAGT | TTTCTAACTC ACATTTGTA | 4323 |
| TAATAAAATT | TTTTGAGTAG | TAGTTCAGTA | CAACTCTAAT | ATTAATGGGC TTTAAATAAG | 4383 |
| GAAATATATA | TTACGTAAAA | ATTAAATCA | TTTTAAAGTT | CTTTCCTACC AAGTAAATAA | 4443 |
| GGGAAAATTT | AATAACAAAA | ATTTAGTTGA | TTTTAAAATC | CTAAATATTA GAAAATTAAC | 4503 |
| TTAAAATATA | ATTTCGTCTA | GTGTAAAATT | TATTTTTAAA | GGGTAAAAAA GACGAACGAC | 4563 |
| ATTAAGAGCC | TTTGTAATTT | TAATATAGTA | TAAATATAAA | TAATTTACCT TTATTCAGTT | 4623 |
| TCTTAACAAG | TAATTTTCCA | TATATAAAAA | ATAAATTTCT | ATATTCACAC AAAAATAATG | 4683 |
| TGTTGGCCCT | CGTAATTCAA | ATACTATCAT | TCATTTCTTG | TCGAGGGAGT AGTAAATACT | 4743 |
| TTAGGAAAG | TTAGCAATAA | GTAATCAAGA | AATCAAGAAA | ACAGAGGTCA TTTGATGCCC | 4803 |
| ACAAATACAA | ATGAAAAAAC | AAAACAAATG | TTACGAAACA | ATAAAGAAC AAGAATAGCC | 4863 |
| TCAAAGTAAA | ACTCTCTGAT | AGACATTTAC | TCTAAATAGA | ATTCTATTTA TAACAATCAA | 4923 |
| AAAGTTTCTA | CATTTATAGA | TAGCTCCACT | AGCCAAATAT | TTTATTATTG GAATCAGCAA | 4983 |
| AATAGGTTGT | TTCTTTTTTT | ATTCTCATTC | TGTCTGTGTT | CTAAACAG CAT TTG CCG | 5040 |
| | | | | His Leu Pro | |

| | | | | | | | | | | | | | | | | |
|---|---|---|---|---|---|---|---|---|---|---|---|---|---|---|---|---|
| TCT | CTA | CGG | AGG | ATA | GAT | CTC | AGC | TGG | TCT | AAA | AGA | TTG | ACG | CGA | ACA | 5088 |
| Ser 620 | Leu | Arg | Arg | Ile 625 | Asp | Leu | Ser | Trp | Ser 630 | Lys | Arg | Leu | Thr | Arg 635 | Thr | |

| | | | | | | | | | | | | | | | | |
|---|---|---|---|---|---|---|---|---|---|---|---|---|---|---|---|---|
| CCA | GAT | TTC | ACG | GGG | ATG | CCA | AAT | TTG | GAG | TAT | GTG | AAT | TTG | TAT | CAA | 5136 |
| Pro | Asp | Phe | Thr | Gly 640 | Met | Pro | Asn | Leu | Glu 645 | Tyr | Val | Asn | Leu | Tyr 650 | Gln | |
| TGT | AGT | AAT | CTT | GAA | GAA | GTT | CAC | CAT | TCC | CTG | GGA | TGT | TGC | AGC | AAA | 5184 |
| Cys | Ser | Asn | Leu | Glu 655 | Glu | Val | His | His | Ser 660 | Leu | Gly | Cys | Cys | Ser 665 | Lys | |
| GTC | ATT | GGT | TTA | TAT | TTG | AAT | GAT | TGT | AAA | AGC | CTT | AAG | AGG | TTT | CCA | 5232 |
| Val | Ile | Gly 670 | Leu | Tyr | Leu | Asn | Asp 675 | Cys | Lys | Ser | Leu | Lys 680 | Arg | Phe | Pro | |
| TGT | GTT | AAC | GTG | GAA | TCT | CTT | GAA | TAT | CTG | GGT | CTA | AGA | AGT | TGC | GAT | 5280 |
| Cys | Val | Asn 685 | Val | Glu | Ser | Leu | Glu 690 | Tyr | Leu | Gly | Leu | Arg 695 | Ser | Cys | Asp | |
| AGT | TTA | GAG | AAA | TTG | CCA | GAA | ATC | TAC | GGG | AGA | ATG | AAG | CCG | GAG | ATA | 5328 |
| Ser 700 | Leu | Glu | Lys | Leu | Pro 705 | Glu | Ile | Tyr | Gly | Arg 710 | Met | Lys | Pro | Glu | Ile 715 | |
| CAG | ATT | CAC | ATG | CAA | GGC | TCT | GGG | ATA | AGG | GAA | CTA | CCA | TCA | TCT | ATT | 5376 |
| Gln | Ile | His | Met | Gln 720 | Gly | Ser | Gly | Ile | Arg 725 | Glu | Leu | Pro | Ser | Ser 730 | Ile | |
| TTT | CAG | TAC | AAA | ACT | CAT | GTT | ACC | AAG | CTA | TTG | TTG | TGG | AAT | ATG | AAA | 5424 |
| Phe | Gln | Tyr | Lys 735 | Thr | His | Val | Thr | Lys 740 | Leu | Leu | Leu | Trp | Asn 745 | Met | Lys | |
| AAC | CTT | GTA | GCT | CTT | CCA | AGC | AGC | ATA | TGT | AGG | TTG | AAA | AGT | TTG | GTT | 5472 |
| Asn | Leu | Val 750 | Ala | Leu | Pro | Ser | Ser 755 | Ile | Cys | Arg | Leu | Lys 760 | Ser | Leu | Val | |
| AGT | CTG | AGT | GTG | TCG | GGT | TGC | TCA | AAA | CTT | GAA | AGC | TTG | CCA | GAA | GAG | 5520 |
| Ser | Leu | Ser 765 | Val | Ser | Gly | Cys | Ser 770 | Lys | Leu | Glu | Ser | Leu 775 | Pro | Glu | Glu | |
| ATA | GGG | GAT | TTA | GAC | AAC | TTA | CGG | GTG | TTT | GAT | GCC | AGT | GAT | ACT | CTA | 5568 |
| Ile 780 | Gly | Asp | Leu | Asp | Asn 785 | Leu | Arg | Val | Phe | Asp 790 | Ala | Ser | Asp | Thr | Leu 795 | |
| ATT | TTA | CGA | CCT | CCG | TCT | TCC | ATC | ATA | CGC | TTG | AAC | AAA | CTT | ATA | ATC | 5616 |
| Ile | Leu | Arg | Pro 800 | Pro | Ser | Ser | Ile | Ile 805 | Arg | Leu | Asn | Lys | Leu 810 | Ile | Ile | |
| TTG | ATG | TTT | CGA | GGC | TTC | AAA | GAT | GGA | GTG | CAC | TTT | GAG | TTC | CCT | CCT | 5664 |
| Leu | Met | Phe | Arg 815 | Gly | Phe | Lys | Asp | Gly 820 | Val | His | Phe | Glu | Phe 825 | Pro | Pro | |
| GTG | GCT | GAA | GGA | TTA | CAC | TCA | TTG | GAA | TAT | CTG | AAT | CTC | AGT | TAC | TGC | 5712 |
| Val | Ala | Glu 830 | Gly | Leu | His | Ser | Leu 835 | Glu | Tyr | Leu | Asn | Leu 840 | Ser | Tyr | Cys | |
| AAT | CTA | ATA | GAT | GGA | GGA | CTT | CCG | GAA | GAG | ATT | GGA | TCC | TTA | TCC | TCT | 5760 |
| Asn | Leu | Ile 845 | Asp | Gly | Gly | Leu | Pro 850 | Glu | Glu | Ile | Gly | Ser 855 | Leu | Ser | Ser | |
| TTG | AAA | AAG | TTG | GAT | CTC | AGT | AGA | AAT | AAT | TTT | GAG | CAT | TTG | CCT | TCA | 5808 |
| Leu | Lys | Lys 860 | Leu | Asp | Leu | Ser | Arg 865 | Asn | Asn | Phe | Glu | His 870 | Leu | Pro | Ser 875 | |
| AGT | ATA | GCC | CAA | CTT | GGT | GCT | CTT | CAA | TCC | TTA | GAC | TTA | AAA | GAT | TGC | 5856 |
| Ser | Ile | Ala | Gln | Leu 880 | Gly | Ala | Leu | Gln | Ser 885 | Leu | Asp | Leu | Lys | Asp 890 | Cys | |
| CAG | AGG | CTT | ACA | CAG | CTA | CCA | GAA | CTT | CCC | CCA | GAA | TTA | AAT | GAA | TTG | 5904 |
| Gln | Arg | Leu | Thr 895 | Gln | Leu | Pro | Glu | Leu 900 | Pro | Pro | Glu | Leu | Asn 905 | Glu | Leu | |
| CAT | GTA | GAT | TGT | CAT | ATG | GCT | CTG | AAA | TTT | ATC | CAT | TAT | TTA | GTA | ACA | 5952 |
| His | Val | Asp | Cys 910 | His | Met | Ala | Leu | Lys 915 | Phe | Ile | His | Tyr | Leu 920 | Val | Thr | |
| AAG | AGA | AAG | AAA | CTA | CAT | AGA | GTG | AAA | CTT | GAT | GAT | GCA | CAC | AAT | GAT | 6000 |
| Lys | Arg | Lys 925 | Lys | Leu | His | Arg | Val 930 | Lys | Leu | Asp | Asp | Ala 935 | His | Asn | Asp | |
| ACT | ATG | TAC | AAT | TTG | TTT | GCA | TAT | ACC | ATG | TTT | CAG | AAT | ATC | TCT | TCC | 6048 |
| Thr 940 | Met | Tyr | Asn | Leu | Phe 945 | Ala | Tyr | Thr | Met | Phe 950 | Gln | Asn | Ile | Ser | Ser 955 | |

```
ATG AGG CAT GAC ATC TCT GCT TCA GAT TCC TTG TCA CTA ACA GTA TTT    6096
Met Arg His Asp Ile Ser Ala Ser Asp Ser Leu Ser Leu Thr Val Phe
            960                 965                 970

ACC GGT CAA CCG TAT CCT GAA AAG ATC CCG AGT TGG TTC CAC CAT CAG    6144
Thr Gly Gln Pro Tyr Pro Glu Lys Ile Pro Ser Trp Phe His His Gln
            975                 980                 985

GGT TGG GAT AGT AGT GTA TCA GTC AAT TTG CCT GAA AAT TGG TAT ATA    6192
Gly Trp Asp Ser Ser Val Ser Val Asn Leu Pro Glu Asn Trp Tyr Ile
            990                 995                 1000

CCT GAT AAA TTC TTG GGA TTT GCT GTA TGT TAC TCT CGT AGC TTA ATT    6240
Pro Asp Lys Phe Leu Gly Phe Ala Val Cys Tyr Ser Arg Ser Leu Ile
            1005                1010                1015

GAC ACA ACA GCT CAC TTG ATT CCC GTA TGT GAT GAC AAG ATG TCG CGC    6288
Asp Thr Thr Ala His Leu Ile Pro Val Cys Asp Asp Lys Met Ser Arg
1020            1025                1030                1035

ATG ACC CAG AAA CTT GCC TTA TCA GAA TGT GAT ACA GAA TCA TCC AAC    6336
Met Thr Gln Lys Leu Ala Leu Ser Glu Cys Asp Thr Glu Ser Ser Asn
            1040                1045                1050

TAT TCA GAA TGG GAT ATA CAT TTT TTC TTT GTA CCT TTT GCT GGC TTA    6384
Tyr Ser Glu Trp Asp Ile His Phe Phe Phe Val Pro Phe Ala Gly Leu
            1055                1060                1065

TGG GAT ACA TCT AAG GCA AAT GGA AAA ACA CCA AAT GAT TAT GGG ATT    6432
Trp Asp Thr Ser Lys Ala Asn Gly Lys Thr Pro Asn Asp Tyr Gly Ile
            1070                1075                1080

ATT AGG CTA TCT TTT TCT GGA GAA GAG AAG ATG TAT GGA CTT CGT TTG    6480
Ile Arg Leu Ser Phe Ser Gly Glu Glu Lys Met Tyr Gly Leu Arg Leu
            1085                1090                1095

TTG TAT AAA GAA GGA CCA GAG GTT AAT GCC TTG TTA CAA ATG AGG GAA    6528
Leu Tyr Lys Glu Gly Pro Glu Val Asn Ala Leu Leu Gln Met Arg Glu
1100            1105                1110                1115

AAT AGC AAT GAA CCA ACA GAA CAT TCC ACT GGG ATA AGG AGG ACT CAA    6576
Asn Ser Asn Glu Pro Thr Glu His Ser Thr Gly Ile Arg Arg Thr Gln
            1120                1125                1130

TAT AAC AAC AGA ACT TCC TTT TAT GTAAGTCTCT ACTTCTATTA GCTACAAAGT   6630
Tyr Asn Asn Arg Thr Ser Phe Tyr
            1135

CTTCTTCCAA AATCAATACT CCATCCGTTC CAGTTTATGT GAACCTATTT TTTGTTCGTC  6690
CATTCTAAAA AGAATGACCC CTTTCTAAAT TGGAAATAA TTTTGGTTAA ACTTATAATT   6750
CTACCATTAA CGAGAAGCTT TTATAACCAC ACAAATATTC TGGGGCCCTT TTTGAATTGT  6810
TTAGGACCAT AAATTCCAAA AGTCCTCATT TTTTCTTAAA CTCCGTGCCC AATCAAACAA  6870
GTTCACGTAA ATTGGAACGG AGGGAATATA TTTTTTCTTC TCATTCTTTT CCCCTATTTA  6930
CAG GAG CTC ATC AAT GGG TGATGTACAT ATCAACAACG AGTTTTAAAG           6978
    Glu Leu Ile Asn Gly
    1140            114

GATTCCAACA AGTATAACTT TTTATGCTCA AATCAGCTCC TTGTATTGTG GAGAAAGCTG  7038
AGTACGAGAT GAAGTTGACG TCCGTTATCC TTTATGATCT CTCTGTTCTT TGTGTTAACT  7098
TGCCTACTTC ATCAGATGAA TAACAGAAGC CGTTCCTCT CATTCTCAAC ACTGTTTGCA   7158
CGTCTGTTGT TACTTGTTAA AATGGATCTT GATAAAGTAA TAACATCTCT ATATTACTTA  7218
TAAGTGGTTT TAACAAGTTC ACTCTTTTGC TTTTGCAGTT CAAATGGGAA CACAATGTAT  7278
ATTGAGAACT AGAACAATGA CACTGCATAT ATATATATAT ATGTATGTAT GTAATTCTCG  7338
TCTTTTGGAC TAGAATACCT TGTTTCATTA TGAAATGAAT TAACATCTTC GCCTTTGCTG  7398
AC                                                                7400
```

( 2 ) INFORMATION FOR SEQ ID NO:2:

( i ) SEQUENCE CHARACTERISTICS:
        ( A ) LENGTH: 1144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ser Ser Ser Ser Ser Ser Arg Trp Ser Tyr Asp Val Phe Leu
 1               5                  10                  15

Ser Phe Arg Gly Glu Asp Thr Arg Lys Thr Phe Thr Ser His Leu Tyr
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
            180                 185                 190

Thr His Leu Glu Lys Ile Glu Ser Leu Leu Glu Ile Gly Ile Asn Gly
        195                 200                 205

Val Arg Ile Met Gly Ile Trp Gly Met Gly Gly Val Gly Lys Thr Thr
    210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
            260                 265                 270

Glu Lys Ala Asn Tyr Asn Asn Glu Glu Asp Gly Lys His Gln Met Ala
        275                 280                 285

Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
            340                 345                 350

Ser Ile Gln Leu Phe Lys Gln His Ala Phe Gly Lys Glu Val Pro Asn
        355                 360                 365
```

| | | | | | | | | | | | | | | |
|---|---|---|---|---|---|---|---|---|---|---|---|---|---|---|
|Glu|Asn 370|Phe|Glu|Lys|Leu|Ser 375|Leu|Glu|Val|Val|Asn 380|Tyr|Ala|Lys|Gly|
|Leu 385|Pro|Leu|Ala|Leu|Lys 390|Val|Trp|Gly|Ser|Leu 395|Leu|His|Asn|Leu|Arg 400|
|Leu|Thr|Glu|Trp|Lys 405|Ser|Ala|Ile|Glu|His 410|Met|Lys|Asn|Asn|Ser 415|Tyr|
|Ser|Gly|Ile|Ile 420|Asp|Lys|Leu|Lys|Ile 425|Ser|Tyr|Asp|Gly|Leu 430|Glu|Pro|
|Lys|Gln|Gln 435|Glu|Met|Phe|Leu|Asp 440|Ile|Ala|Cys|Phe 445|Leu|Arg|Gly|Glu|
|Glu|Lys 450|Asp|Tyr|Ile|Leu|Gln 455|Ile|Leu|Glu|Ser|Cys 460|His|Ile|Gly|Ala|
|Glu 465|Tyr|Gly|Leu|Arg|Ile 470|Leu|Ile|Asp|Lys|Ser 475|Leu|Val|Phe|Ile|Ser 480|
|Glu|Tyr|Asn|Gln|Val 485|Gln|Met|His|Asp|Leu 490|Ile|Gln|Asp|Met|Gly 495|Lys|
|Tyr|Ile|Val|Asn 500|Phe|Gln|Lys|Asp|Pro 505|Gly|Glu|Arg|Ser|Arg 510|Leu|Trp|
|Leu|Ala|Lys 515|Glu|Val|Glu|Glu|Val 520|Met|Ser|Asn|Asn|Thr 525|Gly|Thr|Met|
|Ala|Met 530|Glu|Ala|Ile|Trp|Val 535|Ser|Ser|Tyr|Ser|Ser 540|Thr|Leu|Arg|Phe|
|Ser 545|Asn|Gln|Ala|Val|Lys 550|Asn|Met|Lys|Arg|Leu 555|Arg|Val|Phe|Asn|Met 560|
|Gly|Arg|Ser|Ser|Thr 565|His|Tyr|Ala|Ile|Asp 570|Tyr|Leu|Pro|Asn|Asn 575|Leu|
|Arg|Cys|Phe|Val 580|Cys|Thr|Asn|Tyr|Pro 585|Trp|Glu|Ser|Phe|Pro 590|Ser|Thr|
|Phe|Glu|Leu 595|Lys|Met|Leu|Val|His 600|Leu|Gln|Leu|Arg|His 605|Asn|Ser|Leu|
|Arg|His 610|Leu|Trp|Thr|Glu|Thr 615|Lys|His|Leu|Pro|Ser 620|Leu|Arg|Arg|Ile|
|Asp 625|Leu|Ser|Trp|Ser|Lys 630|Arg|Leu|Thr|Arg|Thr 635|Pro|Asp|Phe|Thr|Gly 640|
|Met|Pro|Asn|Leu|Glu 645|Tyr|Val|Asn|Leu|Tyr 650|Gln|Cys|Ser|Asn|Leu 655|Glu|
|Glu|Val|His|His 660|Ser|Leu|Gly|Cys|Cys 665|Ser|Lys|Val|Ile|Gly 670|Leu|Tyr|
|Leu|Asn|Asp|Cys 675|Lys|Ser|Leu|Lys|Arg 680|Phe|Pro|Cys|Val 685|Asn|Val|Glu|
|Ser|Leu 690|Glu|Tyr|Leu|Gly|Leu 695|Arg|Ser|Cys|Asp|Ser 700|Leu|Glu|Lys|Leu|
|Pro 705|Glu|Ile|Tyr|Gly|Arg 710|Met|Lys|Pro|Glu|Ile 715|Gln|Ile|His|Met|Gln 720|
|Gly|Ser|Gly|Ile|Arg 725|Glu|Leu|Pro|Ser|Ser 730|Ile|Phe|Gln|Tyr|Lys 735|Thr|
|His|Val|Thr|Lys 740|Leu|Leu|Leu|Trp|Asn 745|Met|Lys|Asn|Leu|Val 750|Ala|Leu|
|Pro|Ser|Ser 755|Ile|Cys|Arg|Leu|Lys 760|Ser|Leu|Val|Ser|Leu 765|Ser|Val|Ser|
|Gly|Cys 770|Ser|Lys|Leu|Glu|Ser 775|Leu|Pro|Glu|Glu|Ile 780|Gly|Asp|Leu|Asp|
|Asn 785|Leu|Arg|Val|Phe|Asp 790|Ala|Ser|Asp|Thr|Leu 795|Ile|Leu|Arg|Pro|Pro 800|

```
Ser  Ser  Ile  Ile  Arg  Leu  Asn  Lys  Leu  Ile  Ile  Leu  Met  Phe  Arg  Gly
               805                      810                     815
Phe  Lys  Asp  Gly  Val  His  Phe  Glu  Phe  Pro  Pro  Val  Ala  Glu  Gly  Leu
               820                      825                     830
His  Ser  Leu  Glu  Tyr  Leu  Asn  Leu  Ser  Tyr  Cys  Asn  Leu  Ile  Asp  Gly
               835                      840                     845
Gly  Leu  Pro  Glu  Glu  Ile  Gly  Ser  Leu  Ser  Ser  Leu  Lys  Lys  Leu  Asp
          850                      855                     860
Leu  Ser  Arg  Asn  Asn  Phe  Glu  His  Leu  Pro  Ser  Ser  Ile  Ala  Gln  Leu
865                      870                     875                          880
Gly  Ala  Leu  Gln  Ser  Leu  Asp  Leu  Lys  Asp  Cys  Gln  Arg  Leu  Thr  Gln
                    885                     890                     895
Leu  Pro  Glu  Leu  Pro  Pro  Glu  Leu  Asn  Glu  Leu  His  Val  Asp  Cys  His
               900                     905                      910
Met  Ala  Leu  Lys  Phe  Ile  His  Tyr  Leu  Val  Thr  Lys  Arg  Lys  Lys  Leu
               915                     920                      925
His  Arg  Val  Lys  Leu  Asp  Asp  Ala  His  Asn  Asp  Thr  Met  Tyr  Asn  Leu
          930                      935                     940
Phe  Ala  Tyr  Thr  Met  Phe  Gln  Asn  Ile  Ser  Ser  Met  Arg  His  Asp  Ile
945                      950                     955                          960
Ser  Ala  Ser  Asp  Ser  Leu  Ser  Leu  Thr  Val  Phe  Thr  Gly  Gln  Pro  Tyr
                    965                     970                     975
Pro  Glu  Lys  Ile  Pro  Ser  Trp  Phe  His  His  Gln  Gly  Trp  Asp  Ser  Ser
               980                     985                     990
Val  Ser  Val  Asn  Leu  Pro  Glu  Asn  Trp  Tyr  Ile  Pro  Asp  Lys  Phe  Leu
          995                     1000                    1005
Gly  Phe  Ala  Val  Cys  Tyr  Ser  Arg  Ser  Leu  Ile  Asp  Thr  Thr  Ala  His
          1010                    1015                    1020
Leu  Ile  Pro  Val  Cys  Asp  Asp  Lys  Met  Ser  Arg  Met  Thr  Gln  Lys  Leu
1025                    1030                    1035                         1040
Ala  Leu  Ser  Glu  Cys  Asp  Thr  Glu  Ser  Ser  Asn  Tyr  Ser  Glu  Trp  Asp
               1045                    1050                    1055
Ile  His  Phe  Phe  Phe  Val  Pro  Phe  Ala  Gly  Leu  Trp  Asp  Thr  Ser  Lys
               1060                    1065                    1070
Ala  Asn  Gly  Lys  Thr  Pro  Asn  Asp  Tyr  Gly  Ile  Ile  Arg  Leu  Ser  Phe
          1075                    1080                    1085
Ser  Gly  Glu  Glu  Lys  Met  Tyr  Gly  Leu  Arg  Leu  Leu  Tyr  Lys  Glu  Gly
          1090                    1095                    1100
Pro  Glu  Val  Asn  Ala  Leu  Leu  Gln  Met  Arg  Glu  Asn  Ser  Asn  Glu  Pro
1105                    1110                    1115                         1120
Thr  Glu  His  Ser  Thr  Gly  Ile  Arg  Arg  Thr  Gln  Tyr  Asn  Asn  Arg  Thr
               1125                    1130                    1135
Ser  Phe  Tyr  Glu  Leu  Ile  Asn  Gly
               1140
```

( 2 ) INFORMATION FOR SEQ ID NO:3:

( i ) SEQUENCE CHARACTERISTICS:
        ( A ) LENGTH: 3760 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Nicotiana glutinosa -continued ( F ) TISSUE TYPE: leaf ( i x ) FEATURE:
    ( A ) NAME/KEY: CDS
    ( B ) LOCATION: 60..3494

( x i ) SEQUENCE DESCRIPTION: SEQ ID NO:3:

```
GGCACGAGAT TTTTTCACAT ACAGTTTCTT ACTCTTTTCA GAGAATTAAC GTTGAGTCC                    59

ATG GCA TCT TCT TCT TCT TCT TCT AGA TGG AGC TAT GAT GTT TTC TTA                   107
Met Ala Ser Ser Ser Ser Ser Ser Arg Trp Ser Tyr Asp Val Phe Leu
 1               5                  10                  15

AGT TTT AGA GGC GAA GAT ACT CGA AAA ACG TTT ACA AGT CAC TTA TAC                   155
Ser Phe Arg Gly Glu Asp Thr Arg Lys Thr Phe Thr Ser His Leu Tyr
             20                  25                  30

GAA GTC TTG AAT GAT AAG GGA ATA AAA ACC TTT CAA GAT GAT AAA AGG                   203
Glu Val Leu Asn Asp Lys Gly Ile Lys Thr Phe Gln Asp Asp Lys Arg
         35                  40                  45

CTA GAG TAC GGC GCA ACC ATC CCA GGT GAA CTC TGT AAA GCT ATA GAA                   251
Leu Glu Tyr Gly Ala Thr Ile Pro Gly Glu Leu Cys Lys Ala Ile Glu
     50                  55                  60

GAG TCT CAA TTT GCC ATT GTT GTT TTC TCA GAG AAT TAT GCA ACA TCA                   299
Glu Ser Gln Phe Ala Ile Val Val Phe Ser Glu Asn Tyr Ala Thr Ser
 65                  70                  75                  80

AGG TGG TGT TTG AAT GAA CTA GTG AAG ATC ATG GAA TGC AAA ACT CGA                   347
Arg Trp Cys Leu Asn Glu Leu Val Lys Ile Met Glu Cys Lys Thr Arg
                 85                  90                  95

TTT AAG CAA ACT GTT ATA CCG ATA TTC TAT GAT GTG GAT CCA TCA CAT                   395
Phe Lys Gln Thr Val Ile Pro Ile Phe Tyr Asp Val Asp Pro Ser His
             100                 105                 110

GTT CGG AAC CAA AAG GAG AGC TTT GCA AAA GCC TTT GAA GAA CAT GAA                   443
Val Arg Asn Gln Lys Glu Ser Phe Ala Lys Ala Phe Glu Glu His Glu
         115                 120                 125

ACA AAG TAT AAG GAT GAT GTT GAG GGA ATA CAA AGA TGG AGG ATT GCT                   491
Thr Lys Tyr Lys Asp Asp Val Glu Gly Ile Gln Arg Trp Arg Ile Ala
     130                 135                 140

TTA AAT GAA GCG GCC AAT CTC AAA GGC TCC TGT GAT AAT CGT GAC AAG                   539
Leu Asn Glu Ala Ala Asn Leu Lys Gly Ser Cys Asp Asn Arg Asp Lys
145                 150                 155                 160

ACT GAT GCA GAC TGT ATT CGA CAG ATT GTT GAC CAA ATC TCA TCC AAA                   587
Thr Asp Ala Asp Cys Ile Arg Gln Ile Val Asp Gln Ile Ser Ser Lys
                 165                 170                 175

TTA TGC AAG ATT TCT TTA TCT TAT TTG CAA AAC ATT GTT GGA ATA GAT                   635
Leu Cys Lys Ile Ser Leu Ser Tyr Leu Gln Asn Ile Val Gly Ile Asp
             180                 185                 190

ACT CAT TTA GAG AAA ATA GAA TCC TTA CTA GAG ATA GGA ATC AAT GGT                   683
Thr His Leu Glu Lys Ile Glu Ser Leu Leu Glu Ile Gly Ile Asn Gly
         195                 200                 205

GTT CGG ATT ATG GGG ATC TGG GGA ATG GGG GGA GTC GGT AAA ACA ACA                   731
Val Arg Ile Met Gly Ile Trp Gly Met Gly Gly Val Gly Lys Thr Thr
     210                 215                 220

ATA GCA AGA GCT ATA TTT GAT ACT CTT TTA GGA AGA ATG GAT AGT TCC                   779
Ile Ala Arg Ala Ile Phe Asp Thr Leu Leu Gly Arg Met Asp Ser Ser
225                 230                 235                 240

TAT CAA TTT GAT GGT GCT TGT TTC CTT AAG GAT ATT AAA GAA AAC AAA                   827
Tyr Gln Phe Asp Gly Ala Cys Phe Leu Lys Asp Ile Lys Glu Asn Lys
                 245                 250                 255

CGT GGA ATG CAT TCT TTG CAA AAT GCC CTT CTC TCT GAA CTT TTA AGG                   875
Arg Gly Met His Ser Leu Gln Asn Ala Leu Leu Ser Glu Leu Leu Arg
             260                 265                 270

GAA AAA GCT AAT TAC AAT AAT GAG GAG GAT GGA AAG CAC CAA ATG GCT                   923
Glu Lys Ala Asn Tyr Asn Asn Glu Glu Asp Gly Lys His Gln Met Ala
```

|     |     |     |     |     | 275 |     |     |     |     | 280 |     |     |     |     | 285 |     |     |     |      |
|-----|-----|-----|-----|-----|-----|-----|-----|-----|-----|-----|-----|-----|-----|-----|-----|-----|-----|-----|------|
| AGT | AGA | CTT | CGT | TCG | AAG | AAG | GTC | CTA | ATT | GTG | CTT | GAT | GAT | ATA | GAT |     |     |     | 971  |
| Ser | Arg | Leu | Arg | Ser | Lys | Lys | Val | Leu | Ile | Val | Leu | Asp | Asp | Ile | Asp |     |     |     |      |
|     | 290 |     |     |     | 295 |     |     |     |     | 300 |     |     |     |     |     |     |     |     |      |
| AAT | AAA | GAT | CAT | TAT | TTG | GAG | TAT | TTA | GCA | GGT | GAT | CTT | GAT | TGG | TTT |     |     |     | 1019 |
| Asn | Lys | Asp | His | Tyr | Leu | Glu | Tyr | Leu | Ala | Gly | Asp | Leu | Asp | Trp | Phe |     |     |     |      |
| 305 |     |     |     | 310 |     |     |     |     | 315 |     |     |     |     | 320 |     |     |     |     |      |
| GGT | AAT | GGT | AGT | AGA | ATT | ATT | ATA | ACA | ACT | AGA | GAC | AAG | CAT | TTG | ATA |     |     |     | 1067 |
| Gly | Asn | Gly | Ser | Arg | Ile | Ile | Ile | Thr | Thr | Arg | Asp | Lys | His | Leu | Ile |     |     |     |      |
|     |     |     |     | 325 |     |     |     |     | 330 |     |     |     |     | 335 |     |     |     |     |      |
| GAG | AAG | AAT | GAT | ATA | ATA | TAT | GAG | GTG | ACT | GCA | CTA | CCC | GAT | CAT | GAA |     |     |     | 1115 |
| Glu | Lys | Asn | Asp | Ile | Ile | Tyr | Glu | Val | Thr | Ala | Leu | Pro | Asp | His | Glu |     |     |     |      |
|     |     |     | 340 |     |     |     |     | 345 |     |     |     |     | 350 |     |     |     |     |     |      |
| TCC | ATT | CAA | TTG | TTC | AAA | CAA | CAT | GCT | TTC | GGA | AAA | GAA | GTT | CCA | AAT |     |     |     | 1163 |
| Ser | Ile | Gln | Leu | Phe | Lys | Gln | His | Ala | Phe | Gly | Lys | Glu | Val | Pro | Asn |     |     |     |      |
|     |     | 355 |     |     |     |     | 360 |     |     |     |     | 365 |     |     |     |     |     |     |      |
| GAG | AAT | TTT | GAG | AAG | CTT | TCA | TTA | GAG | GTA | GTA | AAT | TAT | GCT | AAA | GGC |     |     |     | 1211 |
| Glu | Asn | Phe | Glu | Lys | Leu | Ser | Leu | Glu | Val | Val | Asn | Tyr | Ala | Lys | Gly |     |     |     |      |
|     | 370 |     |     |     |     | 375 |     |     |     |     | 380 |     |     |     |     |     |     |     |      |
| CTT | CCT | TTA | GCC | CTC | AAA | GTG | TGG | GGT | TCT | TTG | CTG | CAT | AAC | CTA | CGA |     |     |     | 1259 |
| Leu | Pro | Leu | Ala | Leu | Lys | Val | Trp | Gly | Ser | Leu | Leu | His | Asn | Leu | Arg |     |     |     |      |
| 385 |     |     |     |     | 390 |     |     |     |     | 395 |     |     |     |     | 400 |     |     |     |      |
| TTA | ACT | GAA | TGG | AAA | AGT | GCT | ATA | GAG | CAC | ATG | AAA | AAT | AAC | TCT | TAT |     |     |     | 1307 |
| Leu | Thr | Glu | Trp | Lys | Ser | Ala | Ile | Glu | His | Met | Lys | Asn | Asn | Ser | Tyr |     |     |     |      |
|     |     |     |     | 405 |     |     |     |     | 410 |     |     |     |     | 415 |     |     |     |     |      |
| TCT | GGA | ATT | ATT | GAT | AAG | CTC | AAA | ATA | AGT | TAT | GAT | GGA | TTA | GAG | CCC |     |     |     | 1355 |
| Ser | Gly | Ile | Ile | Asp | Lys | Leu | Lys | Ile | Ser | Tyr | Asp | Gly | Leu | Glu | Pro |     |     |     |      |
|     |     |     | 420 |     |     |     |     | 425 |     |     |     |     | 430 |     |     |     |     |     |      |
| AAA | CAA | CAA | GAG | ATG | TTT | TTA | GAT | ATA | GCA | TGC | TTC | TTG | CGA | GGG | GAA |     |     |     | 1403 |
| Lys | Gln | Gln | Glu | Met | Phe | Leu | Asp | Ile | Ala | Cys | Phe | Leu | Arg | Gly | Glu |     |     |     |      |
|     |     | 435 |     |     |     |     | 440 |     |     |     |     | 445 |     |     |     |     |     |     |      |
| GAA | AAA | GAT | TAC | ATC | CTA | CAA | ATC | CTT | GAG | AGT | TGT | CAT | ATT | GGA | GCT |     |     |     | 1451 |
| Glu | Lys | Asp | Tyr | Ile | Leu | Gln | Ile | Leu | Glu | Ser | Cys | His | Ile | Gly | Ala |     |     |     |      |
|     | 450 |     |     |     |     | 455 |     |     |     |     | 460 |     |     |     |     |     |     |     |      |
| GAA | TAC | GGG | TTA | CGT | ATT | TTA | ATT | GAC | AAA | TCT | CTT | GTG | TTC | ATC | TCT |     |     |     | 1499 |
| Glu | Tyr | Gly | Leu | Arg | Ile | Leu | Ile | Asp | Lys | Ser | Leu | Val | Phe | Ile | Ser |     |     |     |      |
| 465 |     |     |     |     | 470 |     |     |     |     | 475 |     |     |     |     | 480 |     |     |     |      |
| GAA | TAT | AAT | CAG | GTT | CAA | ATG | CAT | GAC | TTA | ATA | CAG | GAT | ATG | GGT | AAA |     |     |     | 1547 |
| Glu | Tyr | Asn | Gln | Val | Gln | Met | His | Asp | Leu | Ile | Gln | Asp | Met | Gly | Lys |     |     |     |      |
|     |     |     |     | 485 |     |     |     |     | 490 |     |     |     |     | 495 |     |     |     |     |      |
| TAT | ATA | GTG | AAT | TTT | CAA | AAA | GAT | CCC | GGA | GAA | CGT | AGC | AGA | TTA | TGG |     |     |     | 1595 |
| Tyr | Ile | Val | Asn | Phe | Gln | Lys | Asp | Pro | Gly | Glu | Arg | Ser | Arg | Leu | Trp |     |     |     |      |
|     |     |     | 500 |     |     |     |     | 505 |     |     |     |     | 510 |     |     |     |     |     |      |
| CTC | GCC | AAG | GAA | GTC | GAA | GAA | GTG | ATG | AGC | AAC | AAC | ACA | GGG | ACC | ATG |     |     |     | 1643 |
| Leu | Ala | Lys | Glu | Val | Glu | Glu | Val | Met | Ser | Asn | Asn | Thr | Gly | Thr | Met |     |     |     |      |
|     |     | 515 |     |     |     |     | 520 |     |     |     |     | 525 |     |     |     |     |     |     |      |
| GCA | ATG | GAA | GCA | ATT | TGG | GTT | TCT | TCT | TAT | TCT | AGT | ACT | CTA | CGC | TTT |     |     |     | 1691 |
| Ala | Met | Glu | Ala | Ile | Trp | Val | Ser | Ser | Tyr | Ser | Ser | Thr | Leu | Arg | Phe |     |     |     |      |
|     | 530 |     |     |     |     | 535 |     |     |     |     | 540 |     |     |     |     |     |     |     |      |
| AGC | AAT | CAG | GCC | GTG | AAA | AAT | ATG | AAA | AGG | CTT | AGG | GTA | TTT | AAC | ATG |     |     |     | 1739 |
| Ser | Asn | Gln | Ala | Val | Lys | Asn | Met | Lys | Arg | Leu | Arg | Val | Phe | Asn | Met |     |     |     |      |
| 545 |     |     |     |     | 550 |     |     |     |     | 555 |     |     |     |     | 560 |     |     |     |      |
| GGG | AGG | TCG | TCG | ACA | CAT | TAT | GCC | ATC | GAT | TAT | CTG | CCC | AAC | AAC | TTG |     |     |     | 1787 |
| Gly | Arg | Ser | Ser | Thr | His | Tyr | Ala | Ile | Asp | Tyr | Leu | Pro | Asn | Asn | Leu |     |     |     |      |
|     |     |     |     | 565 |     |     |     |     | 570 |     |     |     |     | 575 |     |     |     |     |      |
| CGT | TGT | TTT | GTT | TGC | ACT | AAC | TAT | CCT | TGG | GAG | TCA | TTT | CCA | TCT | ACA |     |     |     | 1835 |
| Arg | Cys | Phe | Val | Cys | Thr | Asn | Tyr | Pro | Trp | Glu | Ser | Phe | Pro | Ser | Thr |     |     |     |      |
|     |     |     | 580 |     |     |     |     | 585 |     |     |     |     | 590 |     |     |     |     |     |      |
| TTT | GAA | CTC | AAA | ATG | CTT | GTT | CAC | CTC | CAA | CTC | CGA | CAC | AAT | TCT | CTG |     |     |     | 1883 |
| Phe | Glu | Leu | Lys | Met | Leu | Val | His | Leu | Gln | Leu | Arg | His | Asn | Ser | Leu |     |     |     |      |

|     |     |     |     |     |     |     |     |     |     |     |     |     |     |     |     |      |
|---|---|---|---|---|---|---|---|---|---|---|---|---|---|---|---|---|
|     |     |     | 595 |     |     |     |     | 600 |     |     |     |     | 605 |     |     |      |
| CGT | CAT | TTA | TGG | ACA | GAA | ACA | AAG | CAT | TTG | CCG | TCT | CTA | CGG | AGG | ATA | 1931 |
| Arg | His | Leu | Trp | Thr | Glu | Thr | Lys | His | Leu | Pro | Ser | Leu | Arg | Arg | Ile |      |
|     | 610 |     |     |     | 615 |     |     |     |     | 620 |     |     |     |     |     |      |
| GAT | CTC | AGC | TGG | TCT | AAA | AGA | TTG | ACG | CGA | ACA | CCA | GAT | TTC | ACG | GGG | 1979 |
| Asp | Leu | Ser | Trp | Ser | Lys | Arg | Leu | Thr | Arg | Thr | Pro | Asp | Phe | Thr | Gly |      |
| 625 |     |     |     | 630 |     |     |     |     | 635 |     |     |     |     |     | 640 |      |
| ATG | CCA | AAT | TTG | GAG | TAT | GTG | AAT | TTG | TAT | CAA | TGT | AGT | AAT | CTT | GAA | 2027 |
| Met | Pro | Asn | Leu | Glu | Tyr | Val | Asn | Leu | Tyr | Gln | Cys | Ser | Asn | Leu | Glu |      |
|     |     |     |     | 645 |     |     |     |     | 650 |     |     |     |     | 655 |     |      |
| GAA | GTT | CAC | CAT | TCC | CTG | GGA | TGT | TGC | AGC | AAA | GTC | ATT | GGT | TTA | TAT | 2075 |
| Glu | Val | His | His | Ser | Leu | Gly | Cys | Cys | Ser | Lys | Val | Ile | Gly | Leu | Tyr |      |
|     |     |     | 660 |     |     |     |     | 665 |     |     |     |     | 670 |     |     |      |
| TTG | AAT | GAT | TGT | AAA | AGC | CTT | AAG | AGG | TTT | CCA | TGT | GTT | AAC | GTG | GAA | 2123 |
| Leu | Asn | Asp | Cys | Lys | Ser | Leu | Lys | Arg | Phe | Pro | Cys | Val | Asn | Val | Glu |      |
|     |     | 675 |     |     |     |     | 680 |     |     |     |     | 685 |     |     |     |      |
| TCT | CTT | GAA | TAT | CTG | GGT | CTA | AGA | AGT | TGC | GAT | AGT | TTA | GAG | AAA | TTG | 2171 |
| Ser | Leu | Glu | Tyr | Leu | Gly | Leu | Arg | Ser | Cys | Asp | Ser | Leu | Glu | Lys | Leu |      |
|     |     | 690 |     |     |     | 695 |     |     |     |     | 700 |     |     |     |     |      |
| CCA | GAA | ATC | TAC | GGG | AGA | ATG | AAG | CCG | GAG | ATA | CAG | ATT | CAC | ATG | CAA | 2219 |
| Pro | Glu | Ile | Tyr | Gly | Arg | Met | Lys | Pro | Glu | Ile | Gln | Ile | His | Met | Gln |      |
| 705 |     |     |     |     | 710 |     |     |     |     | 715 |     |     |     |     | 720 |      |
| GGC | TCT | GGG | ATA | AGG | GAA | CTA | CCA | TCA | TCT | ATT | TTT | CAG | TAC | AAA | ACT | 2267 |
| Gly | Ser | Gly | Ile | Arg | Glu | Leu | Pro | Ser | Ser | Ile | Phe | Gln | Tyr | Lys | Thr |      |
|     |     |     |     | 725 |     |     |     |     | 730 |     |     |     |     | 735 |     |      |
| CAT | GTT | ACC | AAG | CTA | TTG | TTG | TGG | AAT | ATG | AAA | AAC | CTT | GTA | GCT | CTT | 2315 |
| His | Val | Thr | Lys | Leu | Leu | Leu | Trp | Asn | Met | Lys | Asn | Leu | Val | Ala | Leu |      |
|     |     |     | 740 |     |     |     |     | 745 |     |     |     |     | 750 |     |     |      |
| CCA | AGC | AGC | ATA | TGT | AGG | TTG | AAA | AGT | TTG | GTT | AGT | CTG | AGT | GTG | TCG | 2363 |
| Pro | Ser | Ser | Ile | Cys | Arg | Leu | Lys | Ser | Leu | Val | Ser | Leu | Ser | Val | Ser |      |
|     |     | 755 |     |     |     |     | 760 |     |     |     |     | 765 |     |     |     |      |
| GGT | TGC | TCA | AAA | CTT | GAA | AGC | TTG | CCA | GAA | GAG | ATA | GGG | GAT | TTA | GAC | 2411 |
| Gly | Cys | Ser | Lys | Leu | Glu | Ser | Leu | Pro | Glu | Glu | Ile | Gly | Asp | Leu | Asp |      |
|     |     | 770 |     |     |     |     | 775 |     |     |     |     | 780 |     |     |     |      |
| AAC | TTA | CGG | GTG | TTT | GAT | GCC | AGT | GAT | ACT | CTA | ATT | TTA | CGA | CCT | CCG | 2459 |
| Asn | Leu | Arg | Val | Phe | Asp | Ala | Ser | Asp | Thr | Leu | Ile | Leu | Arg | Pro | Pro |      |
| 785 |     |     |     |     | 790 |     |     |     |     | 795 |     |     |     |     | 800 |      |
| TCT | TCC | ATC | ATA | CGC | TTG | AAC | AAA | CTT | ATA | ATC | TTG | ATG | TTT | CGA | GGC | 2507 |
| Ser | Ser | Ile | Ile | Arg | Leu | Asn | Lys | Leu | Ile | Ile | Leu | Met | Phe | Arg | Gly |      |
|     |     |     |     | 805 |     |     |     |     | 810 |     |     |     |     | 815 |     |      |
| TTC | AAA | GAT | GGA | GTG | CAC | TTT | GAG | TTC | CCT | CCT | GTG | GCT | GAA | GGA | TTA | 2555 |
| Phe | Lys | Asp | Gly | Val | His | Phe | Glu | Phe | Pro | Pro | Val | Ala | Glu | Gly | Leu |      |
|     |     |     | 820 |     |     |     |     | 825 |     |     |     |     | 830 |     |     |      |
| CAC | TCA | TTG | GAA | TAT | CTG | AAT | CTC | AGT | TAC | TGC | AAT | CTA | ATA | GAT | GGA | 2603 |
| His | Ser | Leu | Glu | Tyr | Leu | Asn | Leu | Ser | Tyr | Cys | Asn | Leu | Ile | Asp | Gly |      |
|     |     | 835 |     |     |     |     | 840 |     |     |     |     | 845 |     |     |     |      |
| GGA | CTT | CCG | GAA | GAG | ATT | GGA | TCC | TTA | TCC | TCT | TTG | AAA | AAG | TTG | GAT | 2651 |
| Gly | Leu | Pro | Glu | Glu | Ile | Gly | Ser | Leu | Ser | Ser | Leu | Lys | Lys | Leu | Asp |      |
|     | 850 |     |     |     |     | 855 |     |     |     |     | 860 |     |     |     |     |      |
| CTC | AGT | AGA | AAT | AAT | TTT | GAG | CAT | TTG | CCT | TCA | AGT | ATA | GCC | CAA | CTT | 2699 |
| Leu | Ser | Arg | Asn | Asn | Phe | Glu | His | Leu | Pro | Ser | Ser | Ile | Ala | Gln | Leu |      |
| 865 |     |     |     |     | 870 |     |     |     |     | 875 |     |     |     |     | 880 |      |
| GGT | GCT | CTT | CAA | TCC | TTA | GAC | TTA | AAA | GAT | TGC | CAG | AGG | CTT | ACA | CAG | 2747 |
| Gly | Ala | Leu | Gln | Ser | Leu | Asp | Leu | Lys | Asp | Cys | Gln | Arg | Leu | Thr | Gln |      |
|     |     |     |     | 885 |     |     |     |     | 890 |     |     |     |     | 895 |     |      |
| CTA | CCA | GAA | CTT | CCC | CCA | GAA | TTA | AAT | GAA | TTG | CAT | GTA | GAT | TGT | CAT | 2795 |
| Leu | Pro | Glu | Leu | Pro | Pro | Glu | Leu | Asn | Glu | Leu | His | Val | Asp | Cys | His |      |
|     |     |     |     | 900 |     |     |     |     | 905 |     |     |     |     | 910 |     |      |
| ATG | GCT | CTG | AAA | TTT | ATC | CAT | TAT | TTA | GTA | ACA | AAG | AGA | AAG | AAA | CTA | 2843 |
| Met | Ala | Leu | Lys | Phe | Ile | His | Tyr | Leu | Val | Thr | Lys | Arg | Lys | Lys | Leu |      |

|     |     |     |     |     | 915 |     |     |     |     | 920 |     |     |     |     | 925 |      |
|-----|-----|-----|-----|-----|-----|-----|-----|-----|-----|-----|-----|-----|-----|-----|-----|------|
| CAT | AGA | GTG | AAA | CTT | GAT | GAT | GCA | CAC | AAT | GAT | ACT | ATG | TAC | AAT | TTG | 2891 |
| His | Arg | Val | Lys | Leu | Asp | Asp | Ala | His | Asn | Asp | Thr | Met | Tyr | Asn | Leu |      |
|     | 930 |     |     |     |     | 935 |     |     |     |     | 940 |     |     |     |     |      |
| TTT | GCA | TAT | ACC | ATG | TTT | CAG | AAT | ATC | TCT | TCC | ATG | AGG | CAT | GAC | ATC | 2939 |
| Phe | Ala | Tyr | Thr | Met | Phe | Gln | Asn | Ile | Ser | Ser | Met | Arg | His | Asp | Ile |      |
| 945 |     |     |     |     | 950 |     |     |     |     | 955 |     |     |     |     | 960 |      |
| TCT | GCT | TCA | GAT | TCC | TTG | TCA | CTA | ACA | GTA | TTT | ACC | GGT | CAA | CCG | TAT | 2987 |
| Ser | Ala | Ser | Asp | Ser | Leu | Ser | Leu | Thr | Val | Phe | Thr | Gly | Gln | Pro | Tyr |      |
|     |     |     |     | 965 |     |     |     |     | 970 |     |     |     |     | 975 |     |      |
| CCT | GAA | AAG | ATC | CCG | AGT | TGG | TTC | CAC | CAT | CAG | GGT | TGG | GAT | AGT | AGT | 3035 |
| Pro | Glu | Lys | Ile | Pro | Ser | Trp | Phe | His | His | Gln | Gly | Trp | Asp | Ser | Ser |      |
|     |     |     | 980 |     |     |     |     | 985 |     |     |     |     |     | 990 |     |      |
| GTA | TCA | GTC | AAT | TTG | CCT | GAA | AAT | TGG | TAT | ATA | CCT | GAT | AAA | TTC | TTG | 3083 |
| Val | Ser | Val | Asn | Leu | Pro | Glu | Asn | Trp | Tyr | Ile | Pro | Asp | Lys | Phe | Leu |      |
|     |     | 995 |     |     |     |     | 1000|     |     |     |     | 1005|     |     |     |      |
| GGA | TTT | GCT | GTA | TGT | TAC | TCT | CGT | AGC | TTA | ATT | GAC | ACA | ACA | GCT | CAC | 3131 |
| Gly | Phe | Ala | Val | Cys | Tyr | Ser | Arg | Ser | Leu | Ile | Asp | Thr | Thr | Ala | His |      |
|     | 1010|     |     |     |     | 1015|     |     |     |     | 1020|     |     |     |     |      |
| TTG | ATT | CCC | GTA | TGT | GAT | GAC | AAG | ATG | TCG | CGC | ATG | ACC | CAG | AAA | CTT | 3179 |
| Leu | Ile | Pro | Val | Cys | Asp | Asp | Lys | Met | Ser | Arg | Met | Thr | Gln | Lys | Leu |      |
| 1025|     |     |     |     | 1030|     |     |     |     | 1035|     |     |     |     | 1040|      |
| GCC | TTA | TCA | GAA | TGT | GAT | ACA | GAA | TCA | TCC | AAC | TAT | TCA | GAA | TGG | GAT | 3227 |
| Ala | Leu | Ser | Glu | Cys | Asp | Thr | Glu | Ser | Ser | Asn | Tyr | Ser | Glu | Trp | Asp |      |
|     |     |     |     | 1045|     |     |     |     | 1050|     |     |     |     | 1055|     |      |
| ATA | CAT | TTT | TTC | TTT | GTA | CCT | TTT | GCT | GGC | TTA | TGG | GAT | ACA | TCT | AAG | 3275 |
| Ile | His | Phe | Phe | Phe | Val | Pro | Phe | Ala | Gly | Leu | Trp | Asp | Thr | Ser | Lys |      |
|     |     |     | 1060|     |     |     |     | 1065|     |     |     |     | 1070|     |     |      |
| GCA | AAT | GGA | AAA | ACA | CCA | AAT | GAT | TAT | GGG | ATC | ATT | AGG | CTA | TCT | TTT | 3323 |
| Ala | Asn | Gly | Lys | Thr | Pro | Asn | Asp | Tyr | Gly | Ile | Ile | Arg | Leu | Ser | Phe |      |
|     |     | 1075|     |     |     |     | 1080|     |     |     |     | 1085|     |     |     |      |
| TCT | GGA | GAA | GAG | AAG | ATG | TAT | GGA | CTT | CGT | TTG | TTG | TAT | AAA | GAA | GGA | 3371 |
| Ser | Gly | Glu | Glu | Lys | Met | Tyr | Gly | Leu | Arg | Leu | Leu | Tyr | Lys | Glu | Gly |      |
|     | 1090|     |     |     |     | 1095|     |     |     |     | 1100|     |     |     |     |      |
| CCA | GAG | GTT | AAT | GCC | TTG | TTA | CAA | ATG | AGG | GAA | AAT | AGC | AAT | GAA | CCA | 3419 |
| Pro | Glu | Val | Asn | Ala | Leu | Leu | Gln | Met | Arg | Glu | Asn | Ser | Asn | Glu | Pro |      |
| 1105|     |     |     |     | 1110|     |     |     |     | 1115|     |     |     |     | 1120|      |
| ACA | GAA | CAT | TCC | ACT | GGG | ATA | AGG | AGG | ACT | CAA | TAT | AAC | AAC | AGA | ACT | 3467 |
| Thr | Glu | His | Ser | Thr | Gly | Ile | Arg | Arg | Thr | Gln | Tyr | Asn | Asn | Arg | Thr |      |
|     |     |     |     | 1125|     |     |     |     | 1130|     |     |     |     | 1135|     |      |
| TCC | TTT | TAT | GAG | CTC | ATC | AAT | GGG | TGATGTACAT | ATCAACAACG | AGTTTTAAAG | 3521 |
| Ser | Phe | Tyr | Glu | Leu | Ile | Asn | Gly |   |   |   |      |
|     |     |     | 1140|     |     |     |     |   |   |   |      |

| GATTCCAACA | AGTATAACTT | TTTATGCTCA | AATCAGCTCC | TTGTATTGTG | GAGAAAGCTG | 3581 |
| AGTACGAGAT | GAAGTTGACG | TCCGTTATCC | TTTATGATCT | CTCTGTTCTT | TGTGTTAACT | 3641 |
| TGCCTACTTC | ATCAGATGAA | TAACAGAAGC | CCGTTCCTCT | CATTCTCAAC | ACTGTTTGCA | 3701 |
| CGTCTGTTGT | TACTTGTTAA | AATGGATCTT | GATAAAGTAA | TAACATCTCT | ATATTACTT  | 3760 |

( 2 ) INFORMATION FOR SEQ ID NO:4:

( i ) SEQUENCE CHARACTERISTICS:
        ( A ) LENGTH: 1144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Ser | Ser | Ser | Ser | Ser | Ser | Arg | Trp | Ser | Tyr | Asp | Val | Phe | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Ser Phe Arg Gly Glu Asp Thr Arg Lys Thr Phe Thr Ser His Leu Tyr
            20                  25                  30
Glu Val Leu Asn Asp Lys Gly Ile Lys Thr Phe Gln Asp Lys Arg
        35                  40                  45
Leu Glu Tyr Gly Ala Thr Ile Pro Gly Glu Leu Cys Lys Ala Ile Glu
    50                  55                  60
Glu Ser Gln Phe Ala Ile Val Val Phe Ser Glu Asn Tyr Ala Thr Ser
65                  70                  75                  80
Arg Trp Cys Leu Asn Glu Leu Val Lys Ile Met Glu Cys Lys Thr Arg
                85                  90                  95
Phe Lys Gln Thr Val Ile Pro Ile Phe Tyr Asp Val Asp Pro Ser His
            100                 105                 110
Val Arg Asn Gln Lys Glu Ser Phe Ala Lys Ala Phe Glu Glu His Glu
        115                 120                 125
Thr Lys Tyr Lys Asp Asp Val Glu Gly Ile Gln Arg Trp Arg Ile Ala
    130                 135                 140
Leu Asn Glu Ala Ala Asn Leu Lys Gly Ser Cys Asp Asn Arg Asp Lys
145                 150                 155                 160
Thr Asp Ala Asp Cys Ile Arg Gln Ile Val Asp Gln Ile Ser Ser Lys
                165                 170                 175
Leu Cys Lys Ile Ser Leu Ser Tyr Leu Gln Asn Ile Val Gly Ile Asp
            180                 185                 190
Thr His Leu Glu Lys Ile Glu Ser Leu Leu Glu Ile Gly Ile Asn Gly
        195                 200                 205
Val Arg Ile Met Gly Ile Trp Gly Met Gly Gly Val Gly Lys Thr Thr
    210                 215                 220
Ile Ala Arg Ala Ile Phe Asp Thr Leu Leu Gly Arg Met Asp Ser Ser
225                 230                 235                 240
Tyr Gln Phe Asp Gly Ala Cys Phe Leu Lys Asp Ile Lys Glu Asn Lys
                245                 250                 255
Arg Gly Met His Ser Leu Gln Asn Ala Leu Leu Ser Glu Leu Leu Arg
            260                 265                 270
Glu Lys Ala Asn Tyr Asn Asn Glu Glu Asp Gly Lys His Gln Met Ala
        275                 280                 285
Ser Arg Leu Arg Ser Lys Lys Val Leu Ile Val Leu Asp Asp Ile Asp
    290                 295                 300
Asn Lys Asp His Tyr Leu Glu Tyr Leu Ala Gly Asp Leu Asp Trp Phe
305                 310                 315                 320
Gly Asn Gly Ser Arg Ile Ile Ile Thr Thr Arg Asp Lys His Leu Ile
                325                 330                 335
Glu Lys Asn Asp Ile Ile Tyr Glu Val Thr Ala Leu Pro Asp His Glu
            340                 345                 350
Ser Ile Gln Leu Phe Lys Gln His Ala Phe Gly Lys Glu Val Pro Asn
        355                 360                 365
Glu Asn Phe Glu Lys Leu Ser Leu Glu Val Val Asn Tyr Ala Lys Gly
    370                 375                 380
Leu Pro Leu Ala Leu Lys Val Trp Gly Ser Leu His Asn Leu Arg
385                 390                 395                 400
Leu Thr Glu Trp Lys Ser Ala Ile Glu His Met Lys Asn Asn Ser Tyr
                405                 410                 415
Ser Gly Ile Ile Asp Lys Leu Lys Ile Ser Tyr Asp Gly Leu Glu Pro
            420                 425                 430
Lys Gln Gln Glu Met Phe Leu Asp Ile Ala Cys Phe Leu Arg Gly Glu
```

|     |     | 435 |     |     |     | 440 |     |     |     | 445 |     |     |     |
|-----|-----|-----|-----|-----|-----|-----|-----|-----|-----|-----|-----|-----|-----|

Glu Lys Asp Tyr Ile Leu Gln Ile Leu Glu Ser Cys His Ile Gly Ala
450                     455                 460

Glu Tyr Gly Leu Arg Ile Leu Ile Asp Lys Ser Leu Val Phe Ile Ser
465                 470                 475                     480

Glu Tyr Asn Gln Val Gln Met His Asp Leu Ile Gln Asp Met Gly Lys
            485                 490                     495

Tyr Ile Val Asn Phe Gln Lys Asp Pro Gly Glu Arg Ser Arg Leu Trp
            500                 505                 510

Leu Ala Lys Glu Val Glu Glu Val Met Ser Asn Asn Thr Gly Thr Met
        515                 520                 525

Ala Met Glu Ala Ile Trp Val Ser Ser Tyr Ser Ser Thr Leu Arg Phe
530                     535                 540

Ser Asn Gln Ala Val Lys Asn Met Lys Arg Leu Arg Val Phe Asn Met
545                 550                 555                     560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
                580                 585                 590

Phe Glu Leu Lys Met Leu Val His Leu Gln Leu Arg His Asn Ser Leu
            595                 600                 605

Arg His Leu Trp Thr Glu Thr Lys His Leu Pro Ser Leu Arg Arg Ile
    610                 615                 620

Asp Leu Ser Trp Ser Lys Arg Leu Thr Arg Thr Pro Asp Phe Thr Gly
625                 630                 635                     640

Met Pro Asn Leu Glu Tyr Val Asn Leu Tyr Gln Cys Ser Asn Leu Glu
            645                 650                 655

Glu Val His His Ser Leu Gly Cys Cys Ser Lys Val Ile Gly Leu Tyr
            660                 665                 670

Leu Asn Asp Cys Lys Ser Leu Lys Arg Phe Pro Cys Val Asn Val Glu
            675                 680                 685

Ser Leu Glu Tyr Leu Gly Leu Arg Ser Cys Asp Ser Leu Glu Lys Leu
690                 695                 700

Pro Glu Ile Tyr Gly Arg Met Lys Pro Glu Ile Gln Ile His Met Gln
705                 710                 715                 720

Gly Ser Gly Ile Arg Glu Leu Pro Ser Ser Ile Phe Gln Tyr Lys Thr
                725                 730                 735

His Val Thr Lys Leu Leu Leu Trp Asn Met Lys Asn Leu Val Ala Leu
            740                 745                 750

Pro Ser Ser Ile Cys Arg Leu Lys Ser Leu Val Ser Leu Ser Val Ser
        755                 760                 765

Gly Cys Ser Lys Leu Glu Ser Leu Pro Glu Glu Ile Gly Asp Leu Asp
    770                 775                 780

Asn Leu Arg Val Phe Asp Ala Ser Asp Thr Leu Ile Leu Arg Pro Pro
785                 790                 795                     800

Ser Ser Ile Ile Arg Leu Asn Lys Leu Ile Ile Leu Met Phe Arg Gly
            805                 810                 815

Phe Lys Asp Gly Val His Phe Glu Phe Pro Pro Val Ala Glu Gly Leu
        820                 825                 830

His Ser Leu Glu Tyr Leu Asn Leu Ser Tyr Cys Asn Leu Ile Asp Gly
        835                 840                 845

Gly Leu Pro Glu Glu Ile Gly Ser Leu Ser Ser Leu Lys Lys Leu Asp
850                 855                 860

| Leu | Ser | Arg | Asn | Asn | Phe | Glu | His | Leu | Pro | Ser | Ser | Ile | Ala | Gln | Leu |
| 865 | | | | 870 | | | | | 875 | | | | | | 880 |

| Gly | Ala | Leu | Gln | Ser | Leu | Asp | Leu | Lys | Asp | Cys | Gln | Arg | Leu | Thr | Gln |
| | | | | 885 | | | | | 890 | | | | | 895 | |

| Leu | Pro | Glu | Leu | Pro | Pro | Glu | Leu | Asn | Glu | Leu | His | Val | Asp | Cys | His |
| | | | 900 | | | | | 905 | | | | 910 | | | |

| Met | Ala | Leu | Lys | Phe | Ile | His | Tyr | Leu | Val | Thr | Lys | Arg | Lys | Lys | Leu |
| | | | 915 | | | | 920 | | | | | 925 | | | |

| His | Arg | Val | Lys | Leu | Asp | Asp | Ala | His | Asn | Asp | Thr | Met | Tyr | Asn | Leu |
| | 930 | | | | | 935 | | | | | 940 | | | | |

| Phe | Ala | Tyr | Thr | Met | Phe | Gln | Asn | Ile | Ser | Ser | Met | Arg | His | Asp | Ile |
| 945 | | | | | 950 | | | | | 955 | | | | | 960 |

| Ser | Ala | Ser | Asp | Ser | Leu | Ser | Leu | Thr | Val | Phe | Thr | Gly | Gln | Pro | Tyr |
| | | | | 965 | | | | | 970 | | | | | 975 | |

| Pro | Glu | Lys | Ile | Pro | Ser | Trp | Phe | His | His | Gln | Gly | Trp | Asp | Ser | Ser |
| | | | 980 | | | | | 985 | | | | | 990 | | |

| Val | Ser | Val | Asn | Leu | Pro | Glu | Asn | Trp | Tyr | Ile | Pro | Asp | Lys | Phe | Leu |
| | | | 995 | | | | 1000 | | | | | 1005 | | | |

| Gly | Phe | Ala | Val | Cys | Tyr | Ser | Arg | Ser | Leu | Ile | Asp | Thr | Thr | Ala | His |
| | | | 1010 | | | | 1015 | | | | | 1020 | | | |

| Leu | Ile | Pro | Val | Cys | Asp | Asp | Lys | Met | Ser | Arg | Met | Thr | Gln | Lys | Leu |
| 1025 | | | | | 1030 | | | | | 1035 | | | | | 1040 |

| Ala | Leu | Ser | Glu | Cys | Asp | Thr | Glu | Ser | Ser | Asn | Tyr | Ser | Glu | Trp | Asp |
| | | | | 1045 | | | | | 1050 | | | | | 1055 | |

| Ile | His | Phe | Phe | Phe | Val | Pro | Phe | Ala | Gly | Leu | Trp | Asp | Thr | Ser | Lys |
| | | | 1060 | | | | | 1065 | | | | | 1070 | | |

| Ala | Asn | Gly | Lys | Thr | Pro | Asn | Asp | Tyr | Gly | Ile | Ile | Arg | Leu | Ser | Phe |
| | | | 1075 | | | | | 1080 | | | | | 1085 | | |

| Ser | Gly | Glu | Glu | Lys | Met | Tyr | Gly | Leu | Arg | Leu | Leu | Tyr | Lys | Glu | Gly |
| | | 1090 | | | | | 1095 | | | | | 1100 | | | |

| Pro | Glu | Val | Asn | Ala | Leu | Leu | Gln | Met | Arg | Glu | Asn | Ser | Asn | Glu | Pro |
| 1105 | | | | | 1110 | | | | 1115 | | | | | | 1120 |

| Thr | Glu | His | Ser | Thr | Gly | Ile | Arg | Arg | Thr | Gln | Tyr | Asn | Asn | Arg | Thr |
| | | | | 1125 | | | | | 1130 | | | | | 1135 | |

| Ser | Phe | Tyr | Glu | Leu | Ile | Asn | Gly |
| | | | | 1140 | | | |

( 2 ) INFORMATION FOR SEQ ID NO:5:

( i ) SEQUENCE CHARACTERISTICS:
        ( A ) LENGTH: 3830 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Nicotiana glutinosa
        ( F ) TISSUE TYPE: leaf ( i x ) FEATURE:
        ( A ) NAME/KEY: CDS
        ( B ) LOCATION: 60..2018

( x i ) SEQUENCE DESCRIPTION: SEQ ID NO:5:

| GGCACGAGAT | TTTTTCACAT | ACAGTTTCTT | ACTCTTTTCA | GAGAATTAAC | GTTGAGTCC | 59 |

| ATG | GCA | TCT | TCT | TCT | TCT | TCT | TCT | AGA | TGG | AGC | TAT | GAT | GTT | TTC | TTA | 107 |
| Met | Ala | Ser | Ser | Ser | Ser | Ser | Ser | Arg | Trp | Ser | Tyr | Asp | Val | Phe | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AGT | TTT | AGA | GGC | GAA | GAT | ACT | CGA | AAA | ACG | TTT | ACA | AGT | CAC | TTA | TAC | 155 |
| Ser | Phe | Arg | Gly | Glu | Asp | Thr | Arg | Lys | Thr | Phe | Thr | Ser | His | Leu | Tyr | |
| | | | 20 | | | | 25 | | | | | 30 | | | | |
| GAA | GTC | TTG | AAT | GAT | AAG | GGA | ATA | AAA | ACC | TTT | CAA | GAT | GAT | AAA | AGG | 203 |
| Glu | Val | Leu | Asn | Asp | Lys | Gly | Ile | Lys | Thr | Phe | Gln | Asp | Asp | Lys | Arg | |
| | | 35 | | | | 40 | | | | | 45 | | | | | |
| CTA | GAG | TAC | GGC | GCA | ACC | ATC | CCA | GGT | GAA | CTC | TGT | AAA | GCT | ATA | GAA | 251 |
| Leu | Glu | Tyr | Gly | Ala | Thr | Ile | Pro | Gly | Glu | Leu | Cys | Lys | Ala | Ile | Glu | |
| | 50 | | | | | 55 | | | | | 60 | | | | | |
| GAG | TCT | CAA | TTT | GCC | ATT | GTT | GTT | TTC | TCA | GAG | AAT | TAT | GCA | ACA | TCA | 299 |
| Glu | Ser | Gln | Phe | Ala | Ile | Val | Val | Phe | Ser | Glu | Asn | Tyr | Ala | Thr | Ser | |
| 65 | | | | | 70 | | | | | 75 | | | | | 80 | |
| AGG | TGG | TGT | TTG | AAT | GAA | CTA | GTG | AAG | ATC | ATG | GAA | TGC | AAA | ACT | CGA | 347 |
| Arg | Trp | Cys | Leu | Asn | Glu | Leu | Val | Lys | Ile | Met | Glu | Cys | Lys | Thr | Arg | |
| | | | | 85 | | | | | 90 | | | | | 95 | | |
| TTT | AAG | CAA | ACT | GTT | ATA | CCG | ATA | TTC | TAT | GAT | GTG | GAT | CCA | TCA | CAT | 395 |
| Phe | Lys | Gln | Thr | Val | Ile | Pro | Ile | Phe | Tyr | Asp | Val | Asp | Pro | Ser | His | |
| | | | 100 | | | | | 105 | | | | | 110 | | | |
| GTT | CGG | AAC | CAA | AAG | GAG | AGC | TTT | GCA | AAA | GCC | TTT | GAA | GAA | CAT | GAA | 443 |
| Val | Arg | Asn | Gln | Lys | Glu | Ser | Phe | Ala | Lys | Ala | Phe | Glu | Glu | His | Glu | |
| | | | 115 | | | | | 120 | | | | | 125 | | | |
| ACA | AAG | TAT | AAG | GAT | GAT | GTT | GAG | GGA | ATA | CAA | AGA | TGG | AGG | ATT | GCT | 491 |
| Thr | Lys | Tyr | Lys | Asp | Asp | Val | Glu | Gly | Ile | Gln | Arg | Trp | Arg | Ile | Ala | |
| | 130 | | | | | 135 | | | | | 140 | | | | | |
| TTA | AAT | GAA | GCG | GCC | AAT | CTC | AAA | GGC | TCA | TGT | GAT | AAT | CGT | GAC | AAG | 539 |
| Leu | Asn | Glu | Ala | Ala | Asn | Leu | Lys | Gly | Ser | Cys | Asp | Asn | Arg | Asp | Lys | |
| 145 | | | | | 150 | | | | | 155 | | | | | 160 | |
| ACT | GAT | GCA | GAC | TGT | ATT | CGA | CAG | ATT | GTT | GAC | CAA | ATC | TCA | TCC | AAA | 587 |
| Thr | Asp | Ala | Asp | Cys | Ile | Arg | Gln | Ile | Val | Asp | Gln | Ile | Ser | Ser | Lys | |
| | | | | 165 | | | | | 170 | | | | | 175 | | |
| TTA | TGC | AAG | ATT | TCT | TTA | TCT | TAT | TTG | CAA | AAC | ATT | GTT | GGA | ATA | GAT | 635 |
| Leu | Cys | Lys | Ile | Ser | Leu | Ser | Tyr | Leu | Gln | Asn | Ile | Val | Gly | Ile | Asp | |
| | | | 180 | | | | | 185 | | | | | 190 | | | |
| ACT | CAT | TTA | GAG | AAA | ATA | GAA | TCC | TTA | CTA | GAG | ATA | GGA | ATC | AAT | GGT | 683 |
| Thr | His | Leu | Glu | Lys | Ile | Glu | Ser | Leu | Leu | Glu | Ile | Gly | Ile | Asn | Gly | |
| | | 195 | | | | | 200 | | | | | 205 | | | | |
| GTT | CGG | ATT | ATG | GGG | ATC | TGG | GGA | ATG | GGG | GGA | GTC | GGT | AAA | ACA | ACA | 731 |
| Val | Arg | Ile | Met | Gly | Ile | Trp | Gly | Met | Gly | Gly | Val | Gly | Lys | Thr | Thr | |
| | 210 | | | | | 215 | | | | | 220 | | | | | |
| ATA | GCA | AGA | GCT | ATA | TTT | GAT | ACT | CTT | TTA | GGA | AGA | ATG | GAT | AGT | TCC | 779 |
| Ile | Ala | Arg | Ala | Ile | Phe | Asp | Thr | Leu | Leu | Gly | Arg | Met | Asp | Ser | Ser | |
| 225 | | | | | 230 | | | | | 235 | | | | | 240 | |
| TAT | CAA | TTT | GAT | GGT | GCT | TGT | TTC | CTT | AAG | GAT | ATT | AAA | GAA | AAC | AAA | 827 |
| Tyr | Gln | Phe | Asp | Gly | Ala | Cys | Phe | Leu | Lys | Asp | Ile | Lys | Glu | Asn | Lys | |
| | | | | 245 | | | | | 250 | | | | | 255 | | |
| CGT | GGA | ATG | CAT | TCT | TTG | CAA | AAT | GCC | CTT | CTC | TCT | GAA | CTT | TTA | AGG | 875 |
| Arg | Gly | Met | His | Ser | Leu | Gln | Asn | Ala | Leu | Leu | Ser | Glu | Leu | Leu | Arg | |
| | | | 260 | | | | | 265 | | | | | 270 | | | |
| GAA | AAA | GCT | AAT | TAC | AAT | AAT | GAG | GAG | GAT | GGA | AAG | CAC | CAA | ATG | GCT | 923 |
| Glu | Lys | Ala | Asn | Tyr | Asn | Asn | Glu | Glu | Asp | Gly | Lys | His | Gln | Met | Ala | |
| | | 275 | | | | | 280 | | | | | 285 | | | | |
| AGT | AGA | CTT | CGT | TCG | AAG | AAG | GTC | CTA | ATT | GTG | CTT | GAT | GAT | ATA | GAT | 971 |
| Ser | Arg | Leu | Arg | Ser | Lys | Lys | Val | Leu | Ile | Val | Leu | Asp | Asp | Ile | Asp | |
| | 290 | | | | | 295 | | | | | 300 | | | | | |
| AAT | AAA | GAT | CAT | TAT | TTG | GAG | TAT | TTA | GCA | GGT | GAT | CTT | GAT | TGG | TTT | 1019 |
| Asn | Lys | Asp | His | Tyr | Leu | Glu | Tyr | Leu | Ala | Gly | Asp | Leu | Asp | Trp | Phe | |
| 305 | | | | | 310 | | | | | 315 | | | | | 320 | |
| GGT | AAT | GGT | AGT | AGA | ATT | ATT | ATA | ACA | ACT | AGA | GAC | AAG | CAT | TTG | ATA | 1067 |
| Gly | Asn | Gly | Ser | Arg | Ile | Ile | Ile | Thr | Thr | Arg | Asp | Lys | His | Leu | Ile | |
| | | | | 325 | | | | | 330 | | | | | 335 | | |

| | | | | | | | | | | | | | | | | |
|---|---|---|---|---|---|---|---|---|---|---|---|---|---|---|---|---|
| GAG | AAG | AAT | GAT | ATA | ATA | TAT | GAG | GTG | ACT | GCA | CTA | CCC | GAT | CAT | GAA | 1115 |
| Glu | Lys | Asn | Asp<br>340 | Ile | Ile | Tyr | Glu | Val<br>345 | Thr | Ala | Leu | Pro | Asp<br>350 | His | Glu | |
| TCC | ATT | CAA | TTG | TTC | AAA | CAA | CAT | GCT | TTC | GGA | AAA | GAA | GTT | CCA | AAT | 1163 |
| Ser | Ile<br>355 | Gln | Leu | Phe | Lys | Gln<br>360 | His | Ala | Phe | Gly | Lys<br>365 | Glu | Val | Pro | Asn | |
| GAG | AAT | TTT | GAG | AAG | CTT | TCA | TTA | GAG | GTA | GTA | AAT | TAT | GCT | AAA | GGC | 1211 |
| Glu | Asn<br>370 | Phe | Glu | Lys | Leu | Ser<br>375 | Leu | Glu | Val | Val | Asn<br>380 | Tyr | Ala | Lys | Gly | |
| CTT | CCT | TTA | GCC | CTC | AAA | GTG | TGG | GGT | TCT | TTG | CTG | CAT | AAC | CTA | CGA | 1259 |
| Leu<br>385 | Pro | Leu | Ala | Leu | Lys<br>390 | Val | Trp | Gly | Ser | Leu<br>395 | Leu | His | Asn | Leu | Arg<br>400 | |
| TTA | ACT | GAA | TGG | AAA | AGT | GCT | ATA | GAG | CAC | ATG | AAA | AAT | AAC | TCT | TAT | 1307 |
| Leu | Thr | Glu | Trp | Lys<br>405 | Ser | Ala | Ile | Glu | His<br>410 | Met | Lys | Asn | Asn | Ser<br>415 | Tyr | |
| TCT | GGA | ATT | ATT | GAT | AAG | CTC | AAA | ATA | AGT | TAT | GAT | GGA | TTA | GAG | CCC | 1355 |
| Ser | Gly | Ile | Ile<br>420 | Asp | Lys | Leu | Lys | Ile<br>425 | Ser | Tyr | Asp | Gly | Leu<br>430 | Glu | Pro | |
| AAA | CAA | CAA | GAG | ATG | TTT | TTA | GAT | ATA | GCA | TGC | TTC | TTG | CGA | GGG | GAA | 1403 |
| Lys | Gln | Gln<br>435 | Glu | Met | Phe | Leu | Asp<br>440 | Ile | Ala | Cys | Phe | Leu<br>445 | Arg | Gly | Glu | |
| GAA | AAA | GAT | TAC | ATC | CTA | CAA | ATC | CTT | GAG | AGT | TGT | CAT | ATT | GGA | GCT | 1451 |
| Glu | Lys<br>450 | Asp | Tyr | Ile | Leu | Gln<br>455 | Ile | Leu | Glu | Ser | Cys<br>460 | His | Ile | Gly | Ala | |
| GAA | TAC | GGG | TTA | CGT | ATT | TTA | ATT | GAC | AAA | TCT | CTT | GTG | TTC | ATC | TCT | 1499 |
| Glu<br>465 | Tyr | Gly | Leu | Arg | Ile<br>470 | Leu | Ile | Asp | Lys | Ser<br>475 | Leu | Val | Phe | Ile | Ser<br>480 | |
| GAA | TAT | AAT | CAG | GTT | CAA | ATG | CAT | GAC | TTA | ATA | CAG | GAT | ATG | GGT | AAA | 1547 |
| Glu | Tyr | Asn | Gln | Val<br>485 | Gln | Met | His | Asp | Leu<br>490 | Ile | Gln | Asp | Met | Gly<br>495 | Lys | |
| TAT | ATA | GTG | AAT | TTT | CAA | AAA | GAT | CCC | GGA | GAA | CGT | AGC | AGA | TTA | TGG | 1595 |
| Tyr | Ile | Val | Asn<br>500 | Phe | Gln | Lys | Asp | Pro<br>505 | Gly | Glu | Arg | Ser | Arg<br>510 | Leu | Trp | |
| CTC | GCC | AAG | GAA | GTC | GAA | GAA | GTG | ATG | AGC | AAC | AAC | ACA | GGG | ACC | ATG | 1643 |
| Leu | Ala | Lys<br>515 | Glu | Val | Glu | Glu | Val<br>520 | Met | Ser | Asn | Asn | Thr<br>525 | Gly | Thr | Met | |
| GCA | ATG | GAA | GCA | ATT | TGG | GTT | TCT | TCT | TAT | TCT | AGT | ACT | CTA | CGC | TTT | 1691 |
| Ala | Met<br>530 | Glu | Ala | Ile | Trp | Val<br>535 | Ser | Ser | Tyr | Ser | Ser<br>540 | Thr | Leu | Arg | Phe | |
| AGC | AAT | CAG | GCC | GTG | AAA | AAT | ATG | AAA | AGG | CTT | AGG | GTA | TTT | AAC | ATG | 1739 |
| Ser<br>545 | Asn | Gln | Ala | Val | Lys<br>550 | Asn | Met | Lys | Arg | Leu<br>555 | Arg | Val | Phe | Asn | Met<br>560 | |
| GGG | AGG | TCG | TCG | ACA | CAT | TAT | GCC | ATC | GAT | TAT | CTG | CCC | AAC | AAC | TTG | 1787 |
| Gly | Arg | Ser | Ser | Thr<br>565 | His | Tyr | Ala | Ile | Asp<br>570 | Tyr | Leu | Pro | Asn | Asn<br>575 | Leu | |
| CGT | TGT | TTT | GTT | TGC | ACT | AAC | TAT | CCT | TGG | GAG | TCA | TTT | CCA | TCT | ACA | 1835 |
| Arg | Cys | Phe | Val<br>580 | Cys | Thr | Asn | Tyr | Pro<br>585 | Trp | Glu | Ser | Phe | Pro<br>590 | Ser | Thr | |
| TTT | GAA | CTC | AAA | ATG | CTT | GTT | CAC | CTC | CAA | CTC | CGA | CAC | AAT | TCT | CTG | 1883 |
| Phe | Glu | Leu<br>595 | Lys | Met | Leu | Val | His<br>600 | Leu | Gln | Leu | Arg | His<br>605 | Asn | Ser | Leu | |
| CGT | CAT | TTA | TGG | ACA | GAA | ACA | AAG | AAG | AAG | AAC | AAT | ATT | GCA | GAG | AAA | 1931 |
| Arg | His<br>610 | Leu | Trp | Thr | Glu | Thr<br>615 | Lys | Lys | Lys | Asn | Asn<br>620 | Ile | Ala | Glu | Lys | |
| GAG | GGA | GAT | GGA | ATT | CTT | ATT | GAA | TTT | TGG | GGC | GAT | TTA | CAA | TGG | GCA | 1979 |
| Glu<br>625 | Gly | Asp | Gly | Ile | Leu<br>630 | Ile | Glu | Phe | Trp | Gly<br>635 | Asp | Leu | Gln | Trp | Ala<br>640 | |
| TTT | GCC | GTC | TCT | ACG | GAG | GAT | AGA | TCT | CAG | CTG | GTC | TAAAAGATTG | | | | 2025 |
| Phe | Ala | Val | Ser | Thr<br>645 | Glu | Asp | Arg | Ser | Gln<br>650 | Leu | Val | | | | | |

| | | | | | |
|---|---|---|---|---|---|
| ACGCGAACAC | CAGATTTCAC | GGGGATGCCA | AATTTGGAGT | ATGTGAATTT | GTATCAATGT | 2085 |
| AGTAATCTTG | AAGAAGTTCA | CCATTCCCTG | GGATGTTGCA | GCAAAGTCAT | TGGTTTATAT | 2145 |
| TTGAATGATT | GTAAAAGCCT | AAGAGGTTT | CCATGTGTTA | ACGTGGAATC | TCTTGAATAT | 2205 |
| CTGGGTCTAA | GAAGTTGCGA | TAGTTTAGAG | AAATTGCCAG | AAATCTACGG | GAGAATGAAG | 2265 |
| CCGGAGATAC | AGATTCACAT | GCAAGGCTCT | GGGATAAGGG | AACTACCATC | ATCTATTTTT | 2325 |
| CAGTACAAAA | CTCATGTTAC | CAAGCTATTG | TTGTGGAATA | TGAAAAACCT | TGTAGCTCTT | 2385 |
| CCAAGCAGCA | TATGTAGGTT | GAAAAGTTTG | GTTAGTCTGA | GTGTGTCGGG | TTGCTCAAAA | 2445 |
| CTTGAAAGCT | TGCCAGAAGA | GATAGGGGAT | TTAGACAACT | TACGGGTGTT | TGATGCCAGT | 2505 |
| GATACTCTAA | TTTTACGACC | TCCGTCTTCC | ATCATACGCT | TGAACAAACT | TATAATCTTG | 2565 |
| ATGTTTCGAG | GCTTCAAAGA | TGGAGTGCAC | TTTGAGTTCC | CTCCTGTGGC | TGAAGGATTA | 2625 |
| CACTCATTGG | AATATCTGAA | TCTCAGTTAC | TGCAATCTAA | TAGATGGAGG | ACTTCCGGAA | 2685 |
| GAGATTGGAT | CCTTATCCTC | TTTGAAAAAG | TTGGATCTCA | GTAGAAATAA | TTTTGAGCAT | 2745 |
| TTGCCTTCAA | GTATAGCCCA | ACTTGGTGCT | CTTCAATCCT | TAGACTTAAA | AGATTGCCAG | 2805 |
| AGGCTTACAC | AGCTACCAGA | ACTTCCCCCA | GAATTAAATG | AATTGCATGT | AGATTGTCAT | 2865 |
| ATGGCTCTGA | AATTTATCCA | TTATTTAGTA | ACAAAGAGAA | AGAAACTACA | TAGAGTGAAA | 2925 |
| CTTGATGATG | CACACAATGA | TACTATGTAC | AATTTGTTTG | CATATACCAT | GTTTCAGAAT | 2985 |
| ATCTCTTCCA | TGAGGCATGA | CATCTCTGCT | TCAGATTCCT | TGTCACTAAC | AGTATTTACC | 3045 |
| GGTCAACCGT | ATCCTGAAAA | GATCCCGAGT | TGGTTCCACC | ATCAGGGTTG | GATAGTAGT | 3105 |
| GTATCAGTCA | ATTTGCCTGA | AAATTGGTAT | ATACCTGATA | AATTCTTGGG | ATTTGCTGTA | 3165 |
| TGTTACTCTC | GTAGCTTAAT | TGACACAACA | GCTCACTTGA | TTCCCGTATG | TGATGACAAG | 3225 |
| ATGTCGCGCA | TGACCCAGAA | ACTTGCCTTA | TCAGAATGTG | ATACAGAATC | ATCCAACTAT | 3285 |
| TCAGAATGGG | ATATACATTT | TTTCTTTGTA | CCTTTTGCTG | GCTTATGGGA | TACATCTAAG | 3345 |
| GCAAATGGAA | AAACACCAAA | TGATTATGGG | ATTATTAGGC | TATCTTTTTC | TGGAGAAGAG | 3405 |
| AAGATGTATG | GACTTCGTTT | GTTGTATAAA | GAAGGACCAG | AGGTTAATGC | CTTGTTACAA | 3465 |
| ATGAGGGAAA | ATAGCAATGA | ACCAACAGAA | CATTCCACTG | GGATAAGGAG | GACTCAATAT | 3525 |
| AACAACAGAA | CTTCCTTTTA | TGAGCTCATC | AATGGGTGAT | GTACATATCA | ACAACGAGTT | 3585 |
| TTAAAGGATT | CCAACAAGTA | TAACTTTTTA | TGCTCAAATC | AGCTCCTTGT | ATTGTGGAGA | 3645 |
| AAGCTGAGTA | CGAGATGAAG | TTGACGTCCG | TTATCCTTTA | TGATCTCTCT | GTTCTTTGTG | 3705 |
| TTAACTTGCC | TACTTCATCA | GATGAATAAC | AGAAGCCCGT | TCCTCTCATT | CTCAACACTG | 3765 |
| TTTGCACGTC | TGTTGTTACT | TGTTAAAATG | GATCTTGATA | AAGTAATAAC | ATCTCTATAT | 3825 |
| TACTT | | | | | | 3830 |

( 2 ) INFORMATION FOR SEQ ID NO:6:

( i ) SEQUENCE CHARACTERISTICS:
        ( A ) LENGTH: 652 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Ala Ser Ser Ser Ser Ser Ser Arg Trp Ser Tyr Asp Val Phe Leu
 1               5                  10                  15

Ser Phe Arg Gly Glu Asp Thr Arg Lys Thr Phe Thr Ser His Leu Tyr
            20                  25                  30

```
Glu Val Leu Asn Asp Lys Gly Ile Lys Thr Phe Gln Asp Asp Lys Arg
        35              40              45
Leu Glu Tyr Gly Ala Thr Ile Pro Gly Glu Leu Cys Lys Ala Ile Glu
    50              55              60
Glu Ser Gln Phe Ala Ile Val Val Phe Ser Glu Asn Tyr Ala Thr Ser
65              70              75              80
Arg Trp Cys Leu Asn Glu Leu Val Lys Ile Met Glu Cys Lys Thr Arg
            85              90              95
Phe Lys Gln Thr Val Ile Pro Ile Phe Tyr Asp Val Asp Pro Ser His
            100             105             110
Val Arg Asn Gln Lys Glu Ser Phe Ala Lys Ala Phe Glu Glu His Glu
        115             120             125
Thr Lys Tyr Lys Asp Asp Val Glu Gly Ile Gln Arg Trp Arg Ile Ala
    130             135             140
Leu Asn Glu Ala Ala Asn Leu Lys Gly Ser Cys Asp Asn Arg Asp Lys
145             150             155             160
Thr Asp Ala Asp Cys Ile Arg Gln Ile Val Asp Gln Ile Ser Ser Lys
            165             170             175
Leu Cys Lys Ile Ser Leu Ser Tyr Leu Gln Asn Ile Val Gly Ile Asp
            180             185             190
Thr His Leu Glu Lys Ile Glu Ser Leu Leu Glu Ile Gly Ile Asn Gly
        195             200             205
Val Arg Ile Met Gly Ile Trp Gly Met Gly Gly Val Gly Lys Thr Thr
    210             215             220
Ile Ala Arg Ala Ile Phe Asp Thr Leu Leu Gly Arg Met Asp Ser Ser
225             230             235             240
Tyr Gln Phe Asp Gly Ala Cys Phe Leu Lys Asp Ile Lys Glu Asn Lys
            245             250             255
Arg Gly Met His Ser Leu Gln Asn Ala Leu Leu Ser Glu Leu Leu Arg
            260             265             270
Glu Lys Ala Asn Tyr Asn Asn Glu Glu Asp Gly Lys His Gln Met Ala
        275             280             285
Ser Arg Leu Arg Ser Lys Lys Val Leu Ile Val Leu Asp Asp Ile Asp
    290             295             300
Asn Lys Asp His Tyr Leu Glu Tyr Leu Ala Gly Asp Leu Asp Trp Phe
305             310             315             320
Gly Asn Gly Ser Arg Ile Ile Ile Thr Thr Arg Asp Lys His Leu Ile
            325             330             335
Glu Lys Asn Asp Ile Ile Tyr Glu Val Thr Ala Leu Pro Asp His Glu
            340             345             350
Ser Ile Gln Leu Phe Lys Gln His Ala Phe Gly Lys Glu Val Pro Asn
        355             360             365
Glu Asn Phe Glu Lys Leu Ser Leu Glu Val Val Asn Tyr Ala Lys Gly
    370             375             380
Leu Pro Leu Ala Leu Lys Val Trp Gly Ser Leu Leu His Asn Leu Arg
385             390             395             400
Leu Thr Glu Trp Lys Ser Ala Ile Glu His Met Lys Asn Asn Ser Tyr
            405             410             415
Ser Gly Ile Ile Asp Lys Leu Lys Ile Ser Tyr Asp Gly Leu Glu Pro
            420             425             430
Lys Gln Gln Glu Met Phe Leu Asp Ile Ala Cys Phe Leu Arg Gly Glu
        435             440             445
Glu Lys Asp Tyr Ile Leu Gln Ile Leu Glu Ser Cys His Ile Gly Ala
```

-continued

|  |  |  |  | 450 |  |  |  |  | 455 |  |  |  | 460 |  |
|---|---|---|---|---|---|---|---|---|---|---|---|---|---|---|
| Glu<br>465 | Tyr | Gly | Leu | Arg | Ile<br>470 | Leu | Ile | Asp | Lys | Ser<br>475 | Leu | Val | Phe | Ile | Ser<br>480 |
| Glu | Tyr | Asn | Gln | Val<br>485 | Gln | Met | His | Asp | Leu<br>490 | Ile | Gln | Asp | Met | Gly<br>495 | Lys |
| Tyr | Ile | Val | Asn<br>500 | Phe | Gln | Lys | Asp | Pro<br>505 | Gly | Glu | Arg | Ser | Arg<br>510 | Leu | Trp |
| Leu | Ala | Lys<br>515 | Glu | Val | Glu | Glu | Val<br>520 | Met | Ser | Asn | Asn | Thr<br>525 | Gly | Thr | Met |
| Ala | Met<br>530 | Glu | Ala | Ile | Trp | Val<br>535 | Ser | Ser | Tyr | Ser | Ser<br>540 | Thr | Leu | Arg | Phe |
| Ser<br>545 | Asn | Gln | Ala | Val | Lys<br>550 | Asn | Met | Lys | Arg | Leu<br>555 | Arg | Val | Phe | Asn | Met<br>560 |
| Gly | Arg | Ser | Ser | Thr<br>565 | His | Tyr | Ala | Ile | Asp<br>570 | Tyr | Leu | Pro | Asn | Asn<br>575 | Leu |
| Arg | Cys | Phe | Val<br>580 | Cys | Thr | Asn | Tyr | Pro<br>585 | Trp | Glu | Ser | Phe | Pro<br>590 | Ser | Thr |
| Phe | Glu | Leu<br>595 | Lys | Met | Leu | Val | His<br>600 | Leu | Gln | Leu | Arg | His<br>605 | Asn | Ser | Leu |
| Arg | His<br>610 | Leu | Trp | Thr | Glu | Thr<br>615 | Lys | Lys | Lys | Asn | Asn<br>620 | Ile | Ala | Glu | Lys |
| Glu<br>625 | Gly | Asp | Gly | Ile | Leu<br>630 | Ile | Glu | Phe | Trp | Gly<br>635 | Asp | Leu | Gln | Trp | Ala<br>640 |
| Phe | Ala | Val | Ser | Thr<br>645 | Glu | Asp | Arg | Ser | Gln<br>650 | Leu | Val |  |  |  |  |

What is claimed is:

1. An isolated and purified nucleic acid molecule comprising a nucleotide sequence encoding an N gene protein selected from the group consisting of:
   (a) a nucleotide sequence encoding an N gene protein as given in SEQ ID NO:3 from nucleotide 60 to nucleotide 3494;
   (b) a nucleotide sequence encoding an N gene protein with an amino acid sequence as given in SEQ ID NO:4;
   (c) a DNA sequence from a plant of the family Solanacae with 70% nucleotide sequence identity with SEQ ID NO:3 from about nucleotide 60 through nucleotide 3494, and wherein said encoded N gene protein has the function of mediating resistance to tobacco mosaic virus in a plant synthesizing said N gene protein;
   (d) a nucleotide sequence encoding N gene protein as given in SEQ ID NO: 1 from nucleotide 1 to nucleotide 7400; and
   (e) a DNA sequence from a plant of the family Solanacae with 70% nucleotide sequence identity with SEQ ID NO: 1 from about nucleotide 1 through nucleotide 7400, and wherein said encoded N gene protein has the function of mediating resistance to tobacco mosaic virus in a plant synthesizing said N gene protein.

2. The nucleic acid molecule of claim 1 wherein said nucleotide sequence encodes an N gene protein with an amino acid sequence as given in SEQ ID NO:4.

3. The nucleic acid molecule of claim 2 wherein said nucleotide sequence encoding an N gene protein is as given in SEQ ID NO:3 from nucleotide 60 to nucleotide 3494.

4. A non-naturally occurring nucleic acid molecule comprising a nucleic acid portion which encodes an N gene protein, said N gene being derived from a plant of the family Solanaceae and said portion encoding an N gene protein and said portion having at least about 70% nucleotide sequence identity with SEQ ID NO:3 from about nucleotide 60 through nucleotide 3494 and wherein said N gene protein has the function of mediating resistance to tobacco mosaic virus in a plant synthesizing said N gene protein.

5. The non-naturally occurring nucleic acid molecule of claim 4 wherein said N gene encoding portion is derived from a plant of the genus Nicotiana.

6. The non-naturally occurring nucleic acid molecule of claim 5 wherein said N gene encoding portion is derived from a plant of the species *Nicotiana glutinosa*.

7. The non-naturally occurring nucleic acid molecule of claim 6 wherein said portion encodes an N gene protein having an amino acid sequence as given in SEQ ID NO:4.

8. The non-naturally occurring nucleic acid molecule of claim 4 wherein said portion encoding an N gene protein has a nucleotide sequence as given in SEQ ID NO:3 from nucleotide 60 to nucleotide 3494, and wherein said N gene protein has the function of mediating resistance to tobacco mosaic virus in a plant synthesizing said N gene protein.

9. A non-naturally occurring nucleic acid molecule comprising a nucleic acid portion which encodes an N gene protein, said N gene being derived from a plant of the family Solanaceae and said portion encoding an N gene protein and said portion having at least about 70% nucleotide sequence identity with SEQ ID NO: 1 from about nucleotide 1 through nucleotide 7400 and wherein said N gene protein has the function of mediating resistance to tobacco mosaic virus in a plant synthesizing said N gene protein.

10. A transgenic plant of the family Solanaceae, which plant has been genetically engineered to contain and express a nucleic acid construction comprising a nucleotide sequence encoding an N gene protein, said N gene protein-encoding nucleotide sequence being derived from a plant of the family Solanaceae, and said N gene-encoding nucleotide sequence having at least about 70% nucleotide sequence identity with SEQ ID NO:3 from about nucleotide 60 through nucleotide 3494 whereby said plant is rendered resistant to tobacco mosaic virus via the expression of said nucleotide sequence encoding said N gene protein.

11. The transgenic plant of claim 10 where said N gene encoding portion is derived from a plant of the genus Nicotiana.

12. The transgenic plant of claim 11 wherein said N gene encoding portion is derived from a plant of the species *Nicotiana glutinosa.*

13. The transgenic plant of claim 10 wherein said portion encodes an N gene protein having an amino acid sequence as given in SEQ ID NO:4.

14. The transgenic plant of claim 10 wherein said portion encoding an N gene protein has a nucleotide sequence as given in SEQ ID NO:3 from nucleotide 60 to nucleotide 3494.

15. The transgenic plant of claim 10 wherein said plant is a member of the genus Capsicum.

16. The transgenic plant of claim 10 wherein said plant is of the genus Lysopersicon.

17. The transgenic plant of claim 16 wherein said plant is of the species *Lysopersicon esculentum.*

18. The transgenic plant of claim 10 wherein said plant is of the genus Nicotiana.

19. The transgenic plant of claim 10 wherein said plant is of the species *Nicotiana tabacura.*

20. The transgenic plant of claim 10 wherein said plant is of the species *Nicotiana glutinosa.*

21. A transgenic plant of the family Solanaceae, which plant has been genetically engineered to contain and express an N gene, said N gene having a nucleotide sequence as given in SEQ ID NO: 1.

22. A transgenic plant of the family Solanaceae, which plant has been genetically engineered to contain and express an N protein coding sequence as given in SEQ ID NO:3, wherein said transgenic plant has been further genetically engineered to contain and express an N derived sequence as given in SEQ ID NO:5.

23. A method of using a nucleic molecule comprising a nucleic acid portion which encodes an N gene protein, said N gene protein-encoding portion being derived from a plant of the family Solanaceae and said N gene protein-encoding portion having at least about 70% nucleotide sequence identity with SEQ ID NO:3 from about nucleotide 60 through nucleotide 3494 and wherein said N gene protein has the function of mediating resistance to tobacco mosaic virus in a plant synthesizing said N gene protein to render a transgenic plant containing and expressing said N gene protein resistant to tobacco mosaic virus, said method comprising the steps of:

(a) genetically engineering plant tissue to contain and express said N gene protein coding sequence; and (b) regenerating the genetically engineered plant tissue of step (a) to form plants, whereby a plant containing and expressing said sequence is rendered resistant to tobacco mosaic virus.

24. The method of claim 23 wherein said N gene encoding portion is derived from a plant of the genus Nicotiana.

25. The method of claim 24 wherein said N gene encoding portion is derived from a plant of the species *Nicotiana glutinosa.*

26. The method of claim 25 wherein said portion encodes an N gene protein having an amino acid sequence as given in SEQ ID NO:4.

27. The method of claim 26 wherein said portion encoding an N gene protein has a nucleotide sequence as given in SEQ ID NO:3 from nucleotide 60 to nucleotide 3494.

28. The method of claim 25 wherein said portion encodes an N gene protein having an amino acid sequence as given in SEQ ID NO:6.

29. The method of claim 28 wherein said portion encoding an N gene protein has a nucleotide sequence as given in SEQ ID NO:5 from nucleotide 60 to nucleotide 2018.

30. A method of using a nucleic acid molecule comprising a nucleic acid portion which encodes an N gene protein, wherein said portion is as given in SEQ ID NO: 1 and has the function of mediating resistance to tobacco mosaic virus in a plant synthesizing said N gene protein to render a transgenic plant containing and expressing said N gene protein resistant to tobacco mosaic virus, said method comprising the steps of:

(a) genetically engineering plant tissue to contain and express said N gene protein coding sequence; and (b) regenerating the genetically engineered plant tissue of step (a) to form plants, whereby a plant containing and expressing said sequence is rendered resistant to tobacco mosaic virus.

31. A method of using a nucleic acid molecule comprising a first nucleic acid portion which encodes an N gene protein, said N gene protein-encoding portion having a nucleotide sequence as given in SEQ ID NO:3 from nucleotide 60 to nucleotide 3494 and a second nucleic acid portion having a nucleotide sequence as given in SEQ ID NO:5, wherein said first and second nucleic acid portions are expressed in plant tissue, said method comprising the step of:

(a) genetically engineering plant tissue to contain and express said first and second nucleic acid portions; and (b) regenerating said plant tissue to form plants, whereby said plants containing and expressing said first and second nucleic acid portions are rendered resistant to tobacco mosaic virus.

32. An isolated and purified nucleic acid molecule comprising a nucleotide sequence encoding an N gene protein having an amino acid sequence as given in SEQ ID NO: 4.

* * * * *